(12) United States Patent
Johnson et al.

(10) Patent No.: US 11,806,099 B2
(45) Date of Patent: Nov. 7, 2023

(54) ARTICULABLE WRISTS FOR SURGICAL TOOL END EFFECTORS

(71) Applicant: Cilag GmbH International, Zug (CH)

(72) Inventors: Eric N. Johnson, Maineville, OH (US); Benjamin D. Dickerson, Cincinnati, OH (US); Jason Alan Hill, Loveland, OH (US); Spencer James Witte, San Francisco, CA (US)

(73) Assignee: Cilag GmbH International, Zug (CH)

( * ) Notice: Subject to any disclaimer, the term of this patent is extended or adjusted under 35 U.S.C. 154(b) by 330 days.

(21) Appl. No.: 17/154,338

(22) Filed: Jan. 21, 2021

(65) Prior Publication Data

US 2022/0226052 A1 Jul. 21, 2022

(51) Int. Cl.
*A61B 34/30* (2016.01)
*A61B 17/29* (2006.01)

(52) U.S. Cl.
CPC ...... *A61B 34/30* (2016.02); *A61B 2017/2936* (2013.01); *A61B 2034/301* (2016.02); *A61B 2034/305* (2016.02)

(58) Field of Classification Search
CPC .............. A61B 34/30; A61B 2034/301; A61B 2034/305; A61B 2017/2926; A61B 17/29; A61B 17/28; A61B 17/30; A61B 17/32
See application file for complete search history.

(56) References Cited

U.S. PATENT DOCUMENTS

| 2012/0158014 A1* | 6/2012 | Stefanchik ............. A61B 34/35 606/130 |
| 2018/0098780 A1* | 4/2018 | Robert ............... A61B 18/1445 |
| 2018/0132925 A1* | 5/2018 | Allen, IV ........... A61B 18/1445 |
| 2018/0303567 A1* | 10/2018 | Simi ...................... A61B 10/04 |
| 2021/0015572 A1 | 1/2021 | Gomez et al. |
| 2021/0022815 A1 | 1/2021 | Abbott |

* cited by examiner

*Primary Examiner* — Timothy J Neal
*Assistant Examiner* — James R McGinnity
(74) *Attorney, Agent, or Firm* — Vorys, Sater, Seymour and Pease LLP

(57) ABSTRACT

A robotic surgical tool includes an elongate shaft, an end effector arranged at a distal end of the shaft and including opposing first and second jaws, and an articulable wrist that interposes the end effector and the distal end, the wrist including a linkage providing one or more lateral arms receivable within a corresponding one or more grooves defined in the first and second jaws, wherein mounting the linkage to the first and second jaws at the corresponding one or more groove generates a jaw pivot where the first and second jaws pivot between open and closed positions.

20 Claims, 30 Drawing Sheets

ARTICULABLE WRISTS FOR SURGICAL TOOL END EFFECTORS

TECHNICAL FIELD

The systems and methods disclosed herein are directed to robotic surgical tools and, more particularly to, articulable wrists for surgical tool end effectors that drive end effector closure and yaw.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving drive cables, rods, and/or other mechanical mechanisms causes the end effector to articulate to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes an elongate shaft, an end effector arranged at a distal end of the shaft and including opposing first and second jaws, and an articulable wrist that interposes the end effector and the distal end, the wrist including a linkage providing one or more lateral arms receivable within a corresponding one or more grooves defined in the first and second jaws, wherein mounting the linkage to the first and second jaws at the corresponding one or more groove generates a jaw pivot where the first and second jaws pivot between open and closed positions. In a further embodiment, the one or more lateral arms slidably engage the corresponding one or more grooves as the first and second jaws pivot between the open and closed positions. In another further embodiment, the linkage comprises first and second linkage portions matable at one or more linkage interfaces, and wherein each distal clevis portion provides a lateral arm of the one or more lateral arms. In another further embodiment, the first and second linkage portions are joined via at least one of welding, soldering, brazing, an adhesive, an interference fit, one or more mechanical fasteners, and any combination thereof. In another further embodiment, the robotic surgical further includes a distal wedge positioned within a central portion of the wrist, the distal wedge defining one or more arcuate surfaces engageable with one or more corresponding curved portions of the first and second jaws. In another further embodiment, the end effector is selected from the group consisting of a surgical stapler, a tissue grasper, surgical scissors, an advanced energy vessel sealer, a clip applier, a needle driver, a babcock including a pair of opposed grasping jaws, bipolar jaws, and any combination thereof.

Embodiments disclosed herein also include a method of assembling an end effector including arranging a linkage about opposing first and second jaws of the end effector, the linkage including first and second linkage portions and each linkage portion providing a lateral arm, receiving the lateral arm of the first linkage portion in a first groove defined in the first jaw, and receiving the lateral arm of the second linkage portion in a second groove defined in the second jaw, pivoting the first and second jaws toward a closed position, adjusting the first and second linkage portions until a desired jaw gap is provided between opposing inner surfaces of the first and second jaws, and joining the first and second linkage portions at one or more linkage interfaces, and thereby setting the desired jaw gap for operation. In a further embodiment, pivoting the first and second jaws toward the closed position comprises moving the first and second jaws toward the closed position until a distal end of the first and second jaws engage each other. In another further embodiment, adjusting the first and second linkage portions comprises adjusting a position of the lateral arms in the first and second grooves. In another further embodiment, adjusting the first and second linkage portions comprises pushing the first and second linkage portions together, and adjusting the first and second linkage portions up or down until the desired jaw gap is achieved. In another further embodiment, joining the first and second linkage portions at the one or more linkage interfaces comprises joining the first and second linkage portions using an attachment means selected from the group of welding, soldering, brazing, an adhesive, an interference fit, one or more mechanical fasteners, and any combination thereof. In another further embodiment, the method further includes adjusting the first and second linkage portions until the opposing inner surfaces of the first and second jaws are parallel. In another further embodiment, the method further includes adjusting the first and second linkage portions until the opposing inner surfaces of the first and second jaws are non-parallel. In another further embodiment, arranging the linkage about the opposing first and second jaws is preceded by positioning a distal wedge between the first and second jaws, the distal wedge defining one or more arcuate surfaces, and receiving one or more corresponding curved portions of the first and second jaws within the one or more arcuate surfaces. In another further embodiment, the first and second grooves each provide distal and proximal sides, the method further comprising increasing a mechanical advantage of the first and second jaws for closure by joining the first and second linkage portions with the lateral arms engageable against the distal side of the first and second grooves. In another further embodiment, the first and second grooves each provide distal and proximal sides, the method further comprising increasing a mechanical advantage of the first and second jaws for opening by joining the first and second linkage portions with the lateral arms engageable against the proximal side of the first and second grooves.

Embodiments disclosed herein also include an end effector for a robotic surgical tool including a first jaw providing a first groove, a second jaw providing a second groove, and a linkage mountable to the first and second jaws and including a first linkage portion having a first lateral arm receivable within the first groove and a second linkage portion having a second lateral arm receivable within the second groove, wherein joining the first and second linkage portions at one or more joint interfaces sets a jaw gap for the first and second jaws. In a further embodiment, the first and second linkage portions are joined via at least one of welding, soldering, brazing, an adhesive, an interference fit, one or more mechanical fasteners, and any combination thereof. In another further embodiment, the one or more lateral arms slidably engage the corresponding one or more grooves as the first and second jaws pivot between open and closed positions. In another further embodiment, the first and second jaws provide first and second jaw extensions, and wherein the end effector further comprises a distal wedge positioned between the first and second jaw extensions and defining one or more arcuate surfaces engageable with one or more corresponding curved portions of the first and second jaws.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
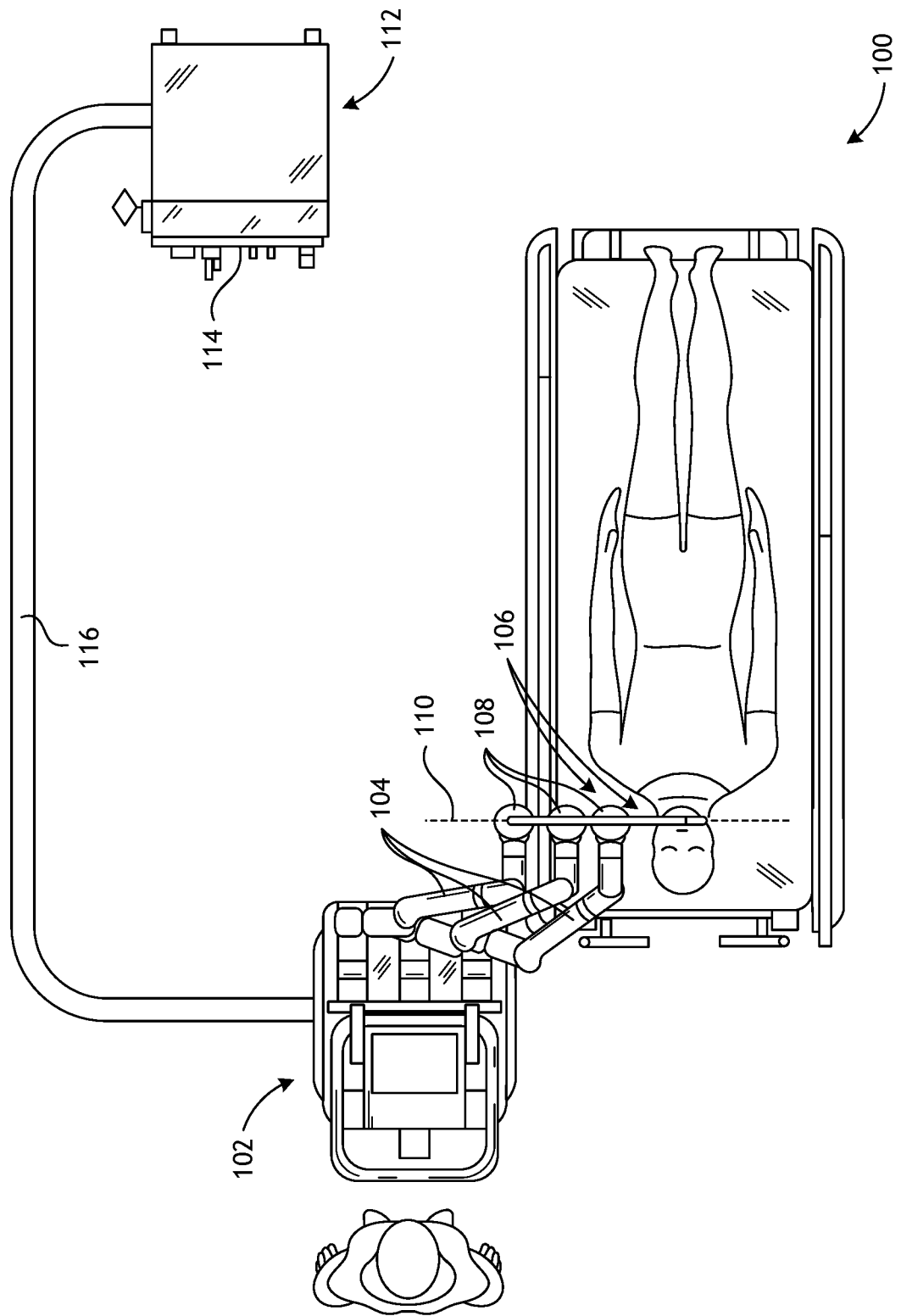
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
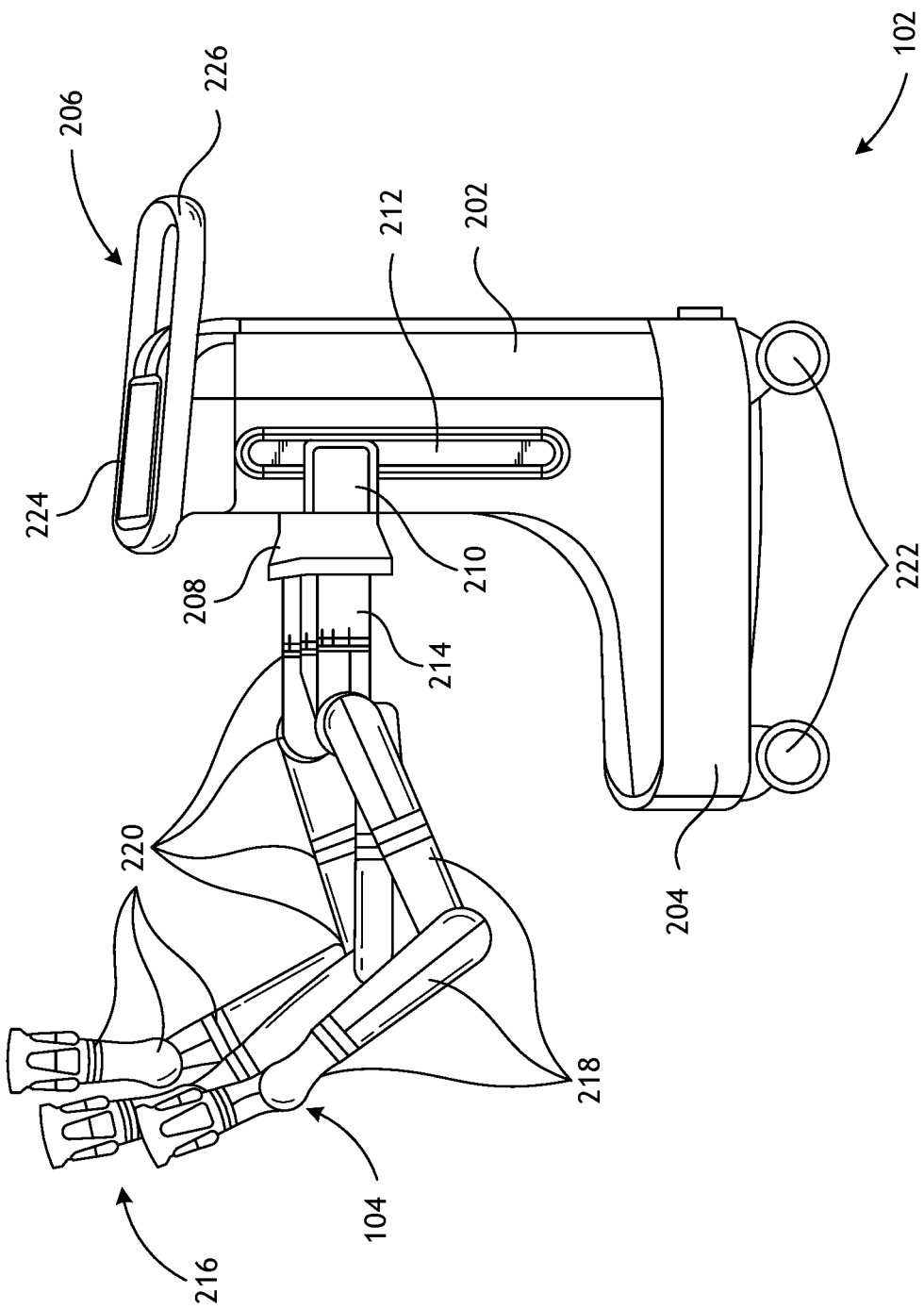
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
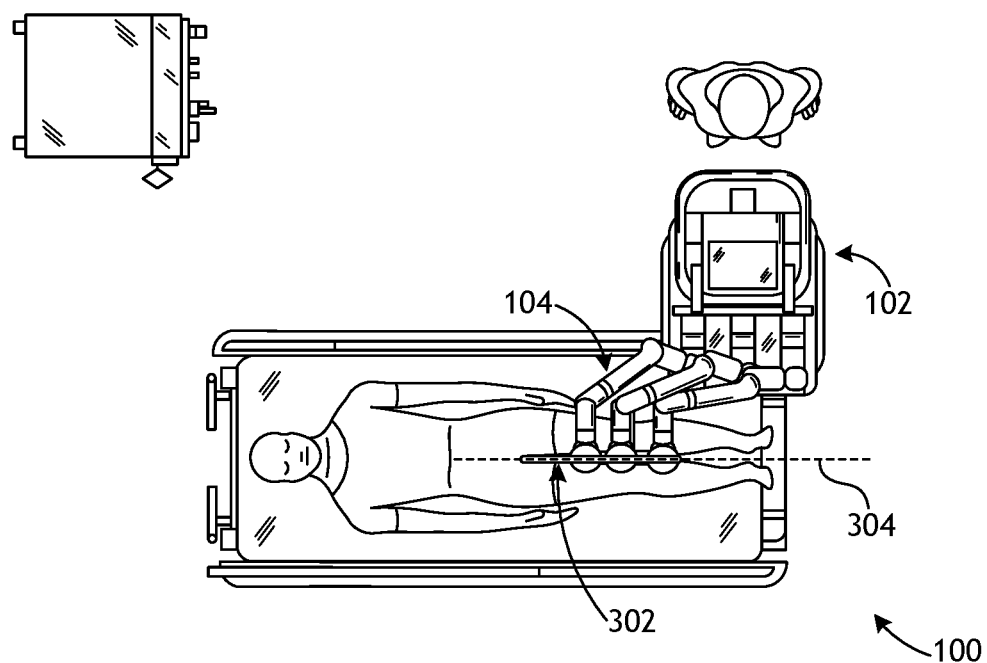
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
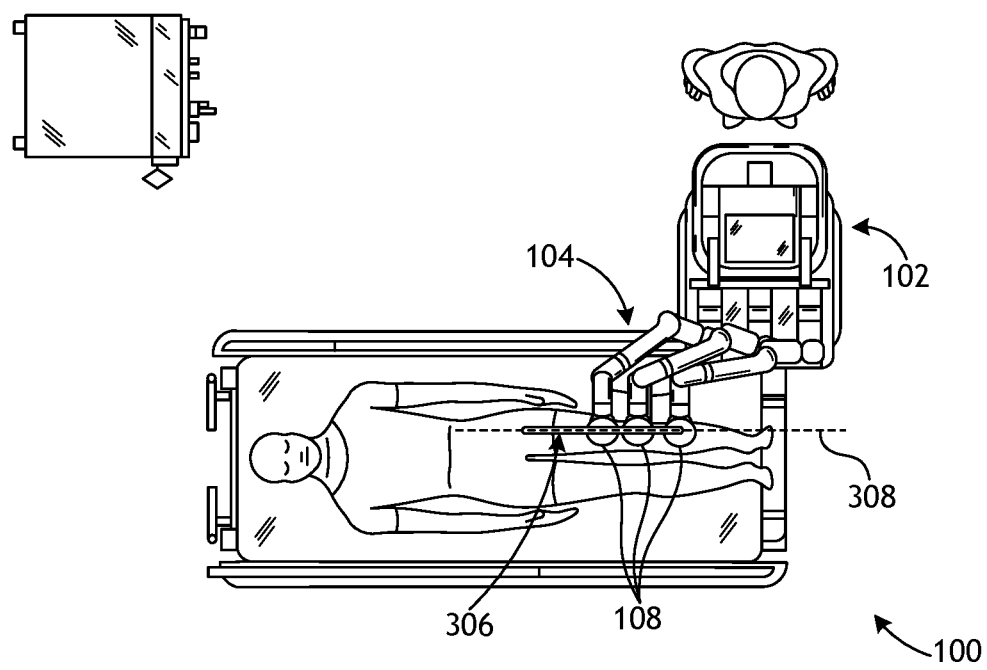
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
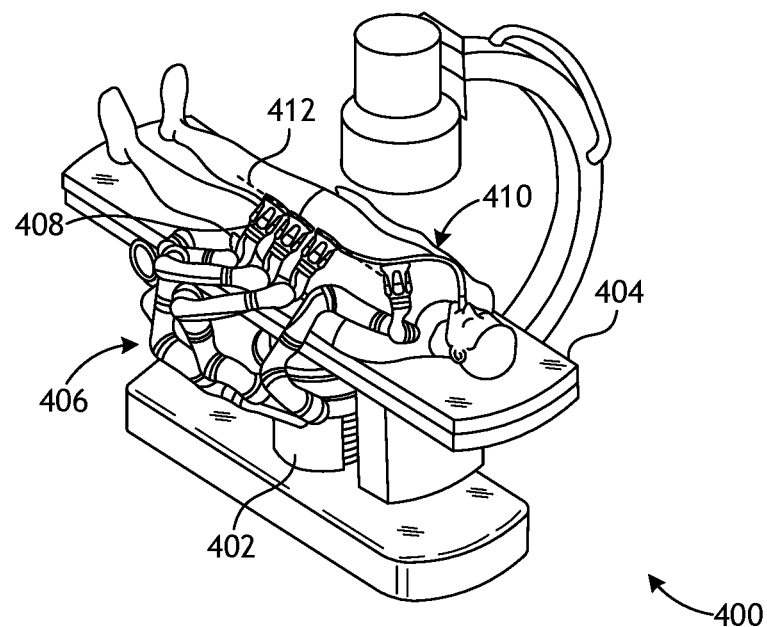
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
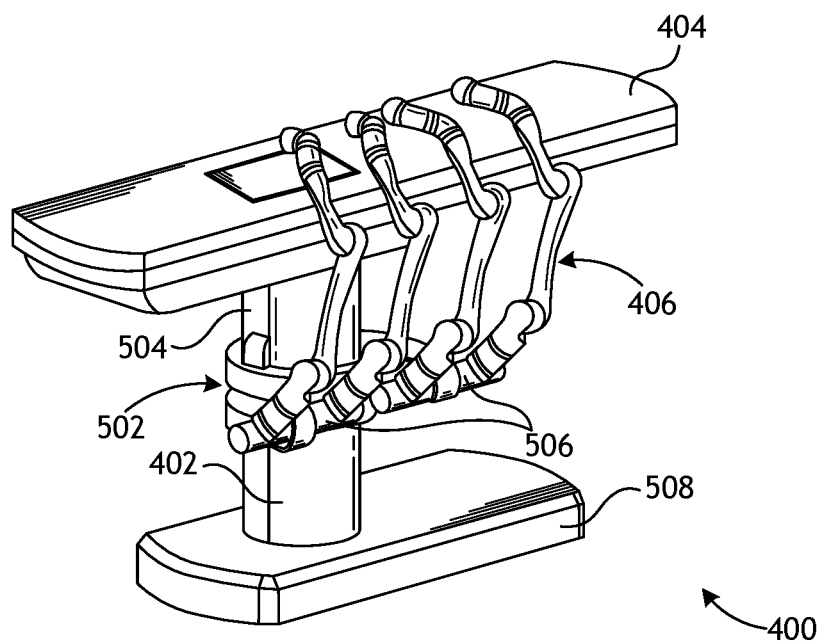
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
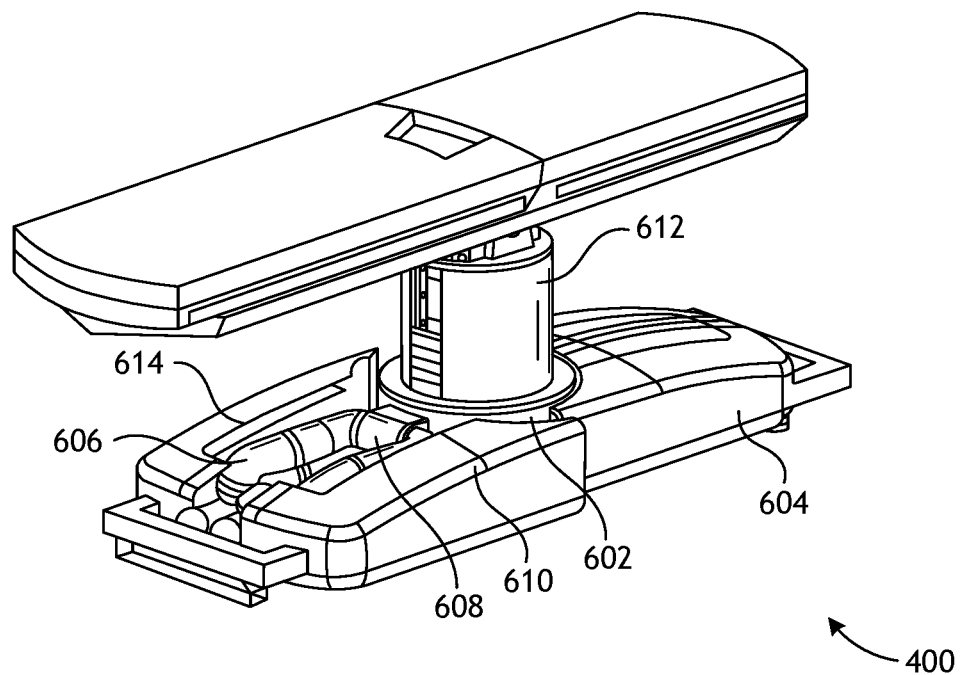
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
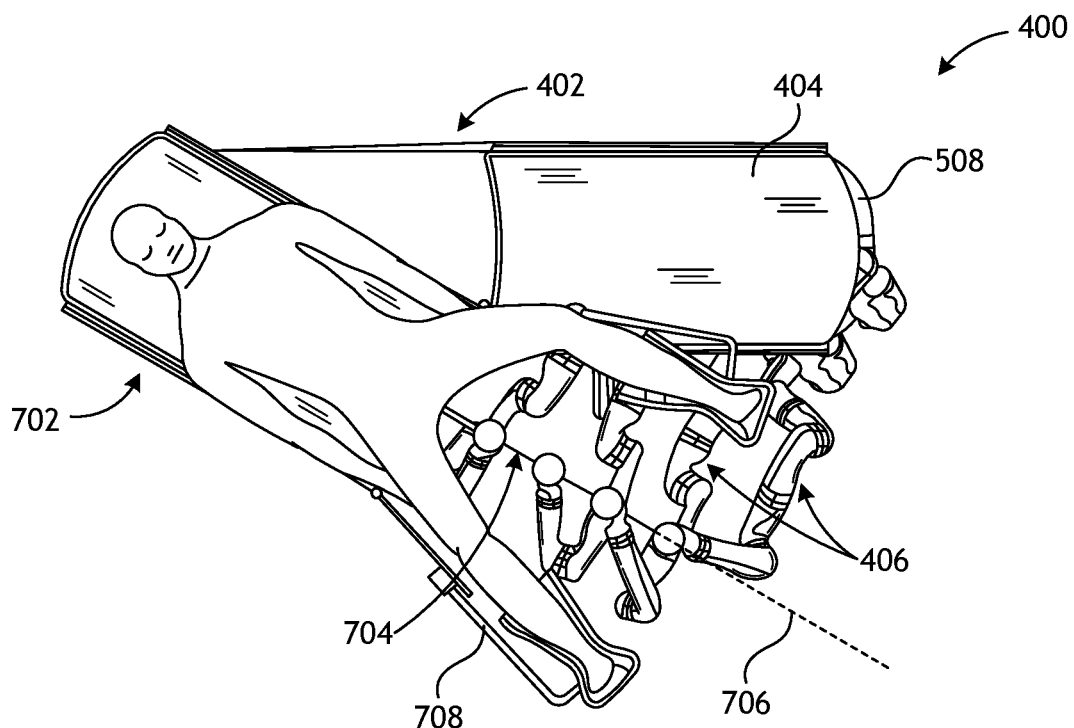
FIG. 7A illustrates an embodiment of a table-based robotic system configured for a ureteroscopy procedure.
Figure 7B:
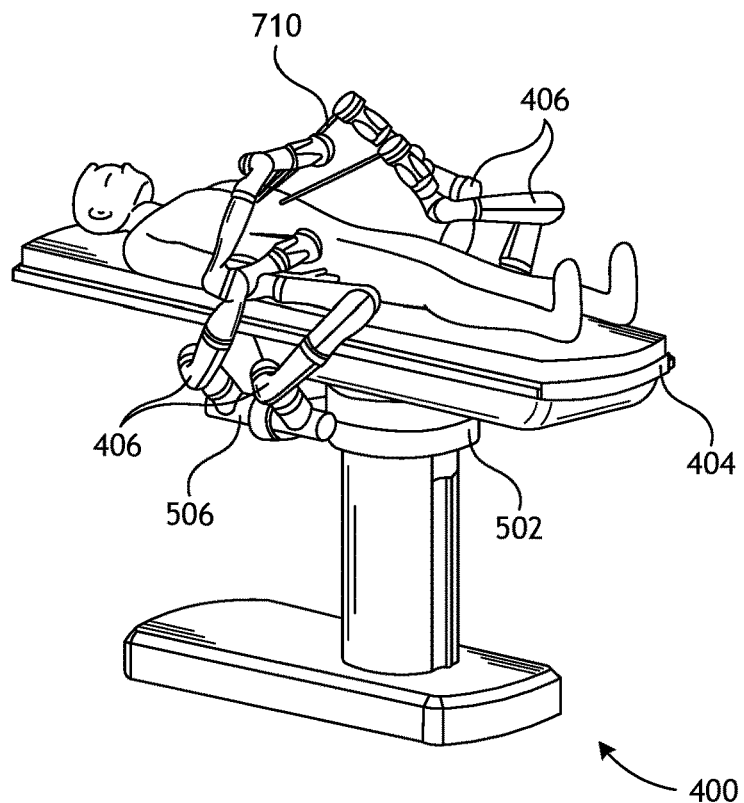
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
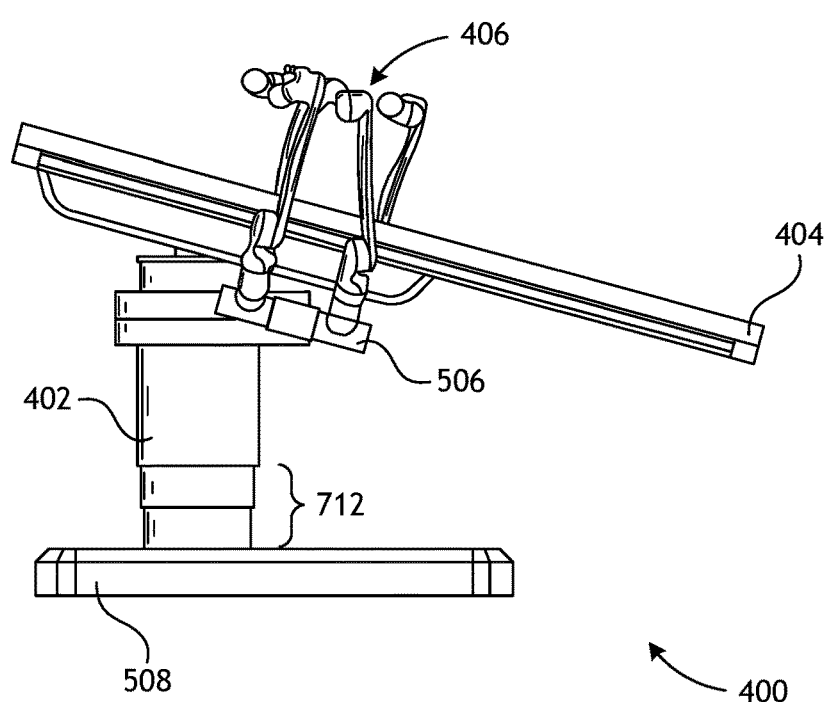
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
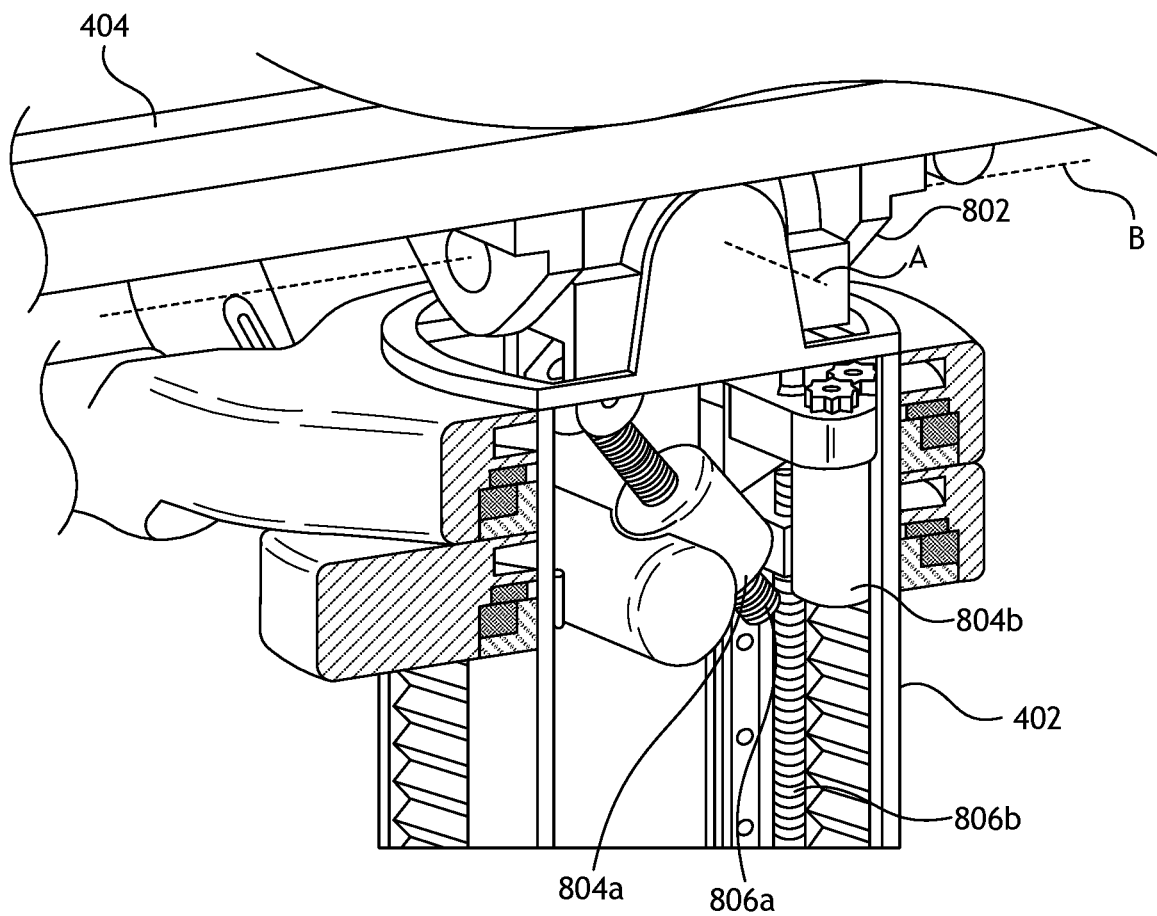
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
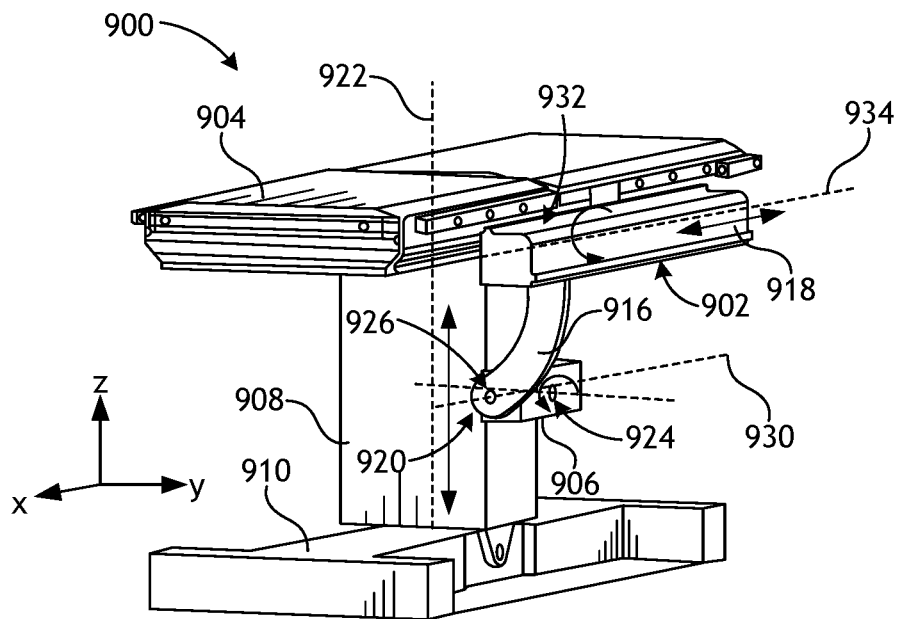
FIG. 9A illustrates an alternative embodiment of a table-based robotic system.
Figure 9B:
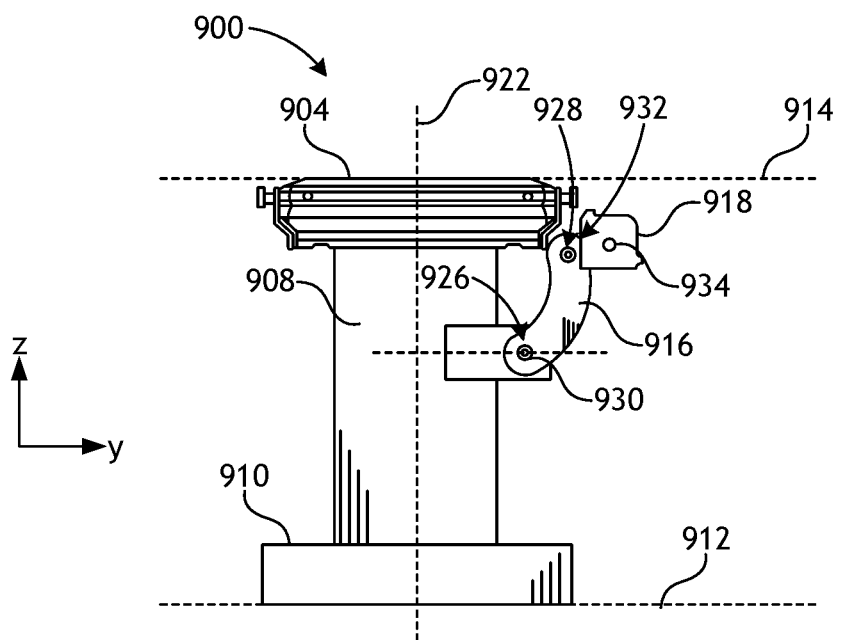
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
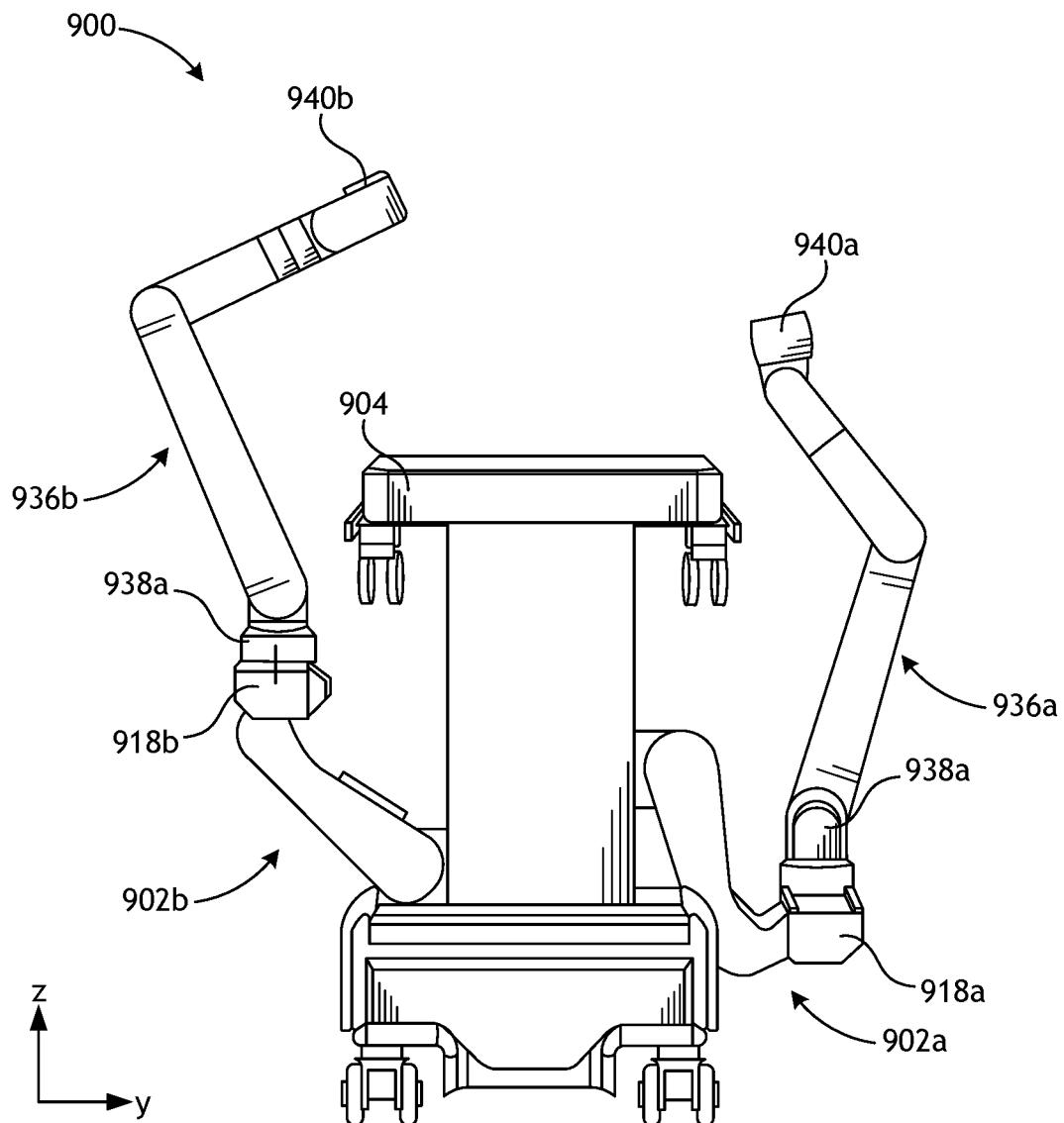
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electromechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
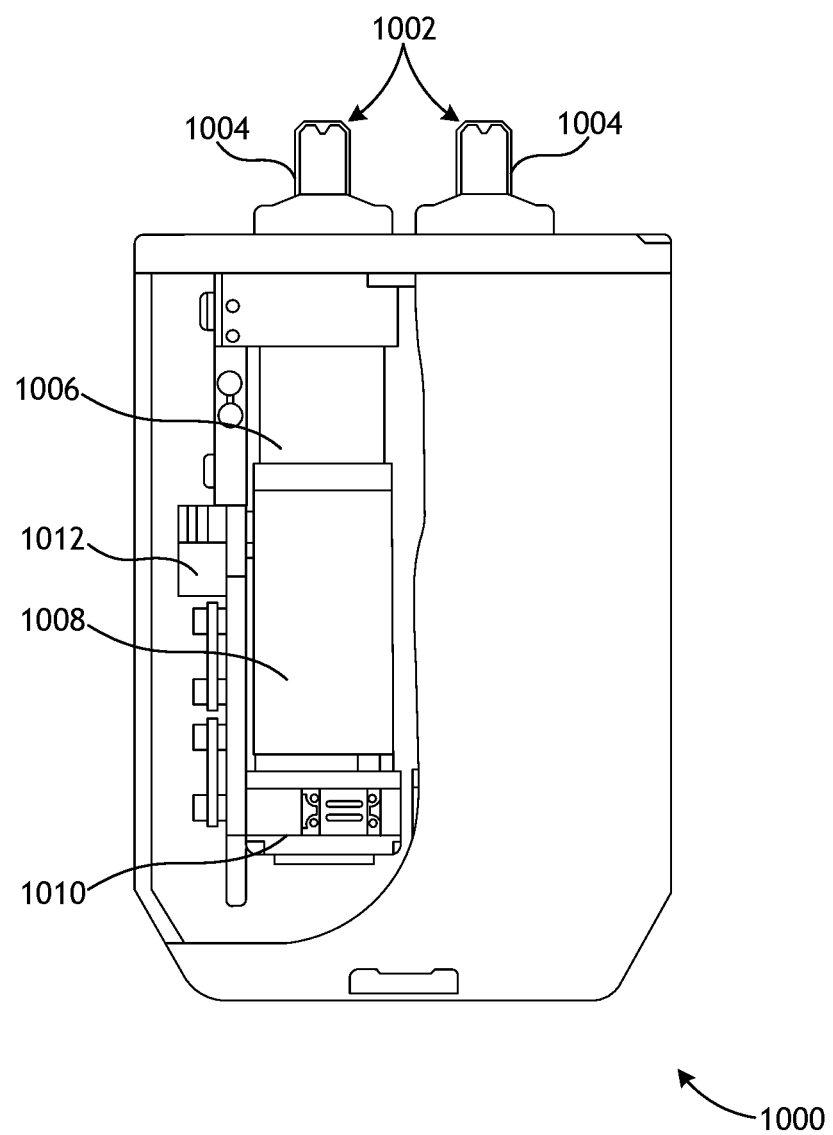
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
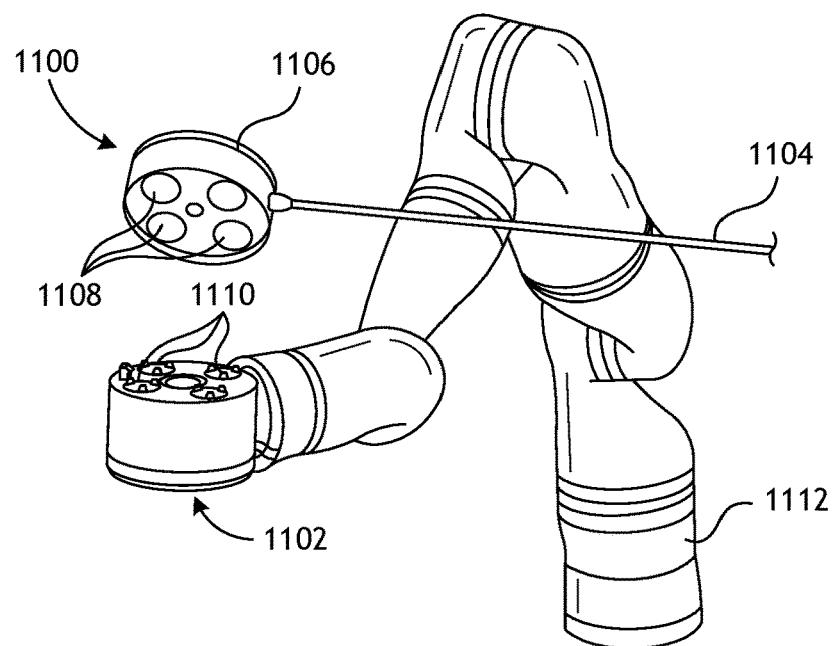
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
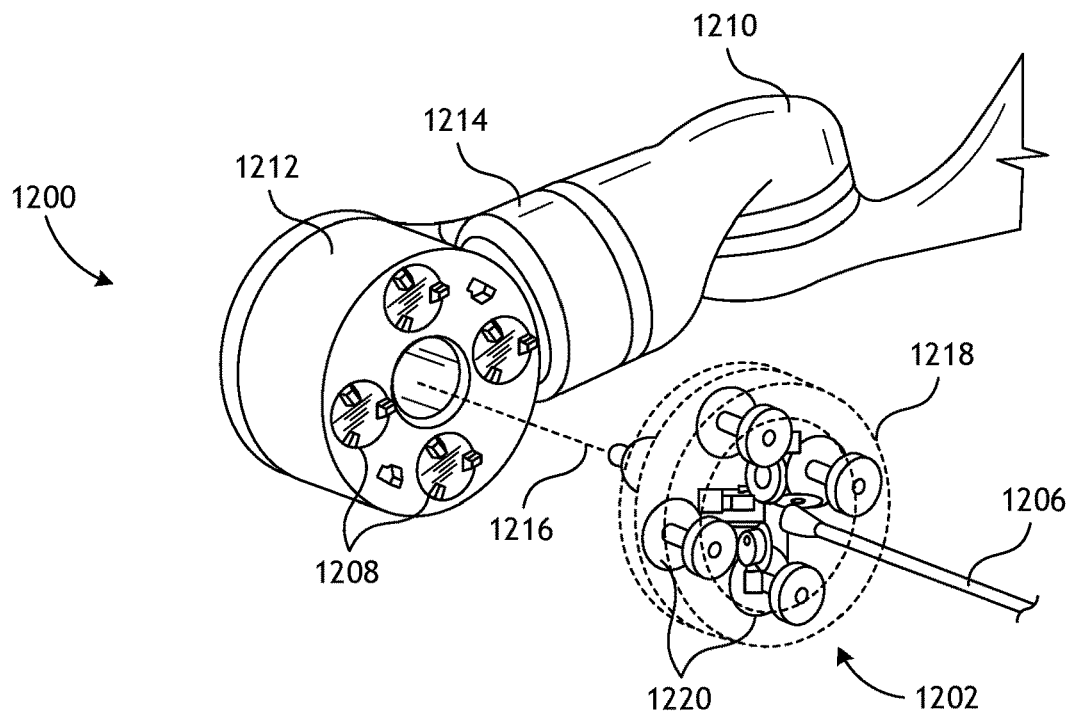
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
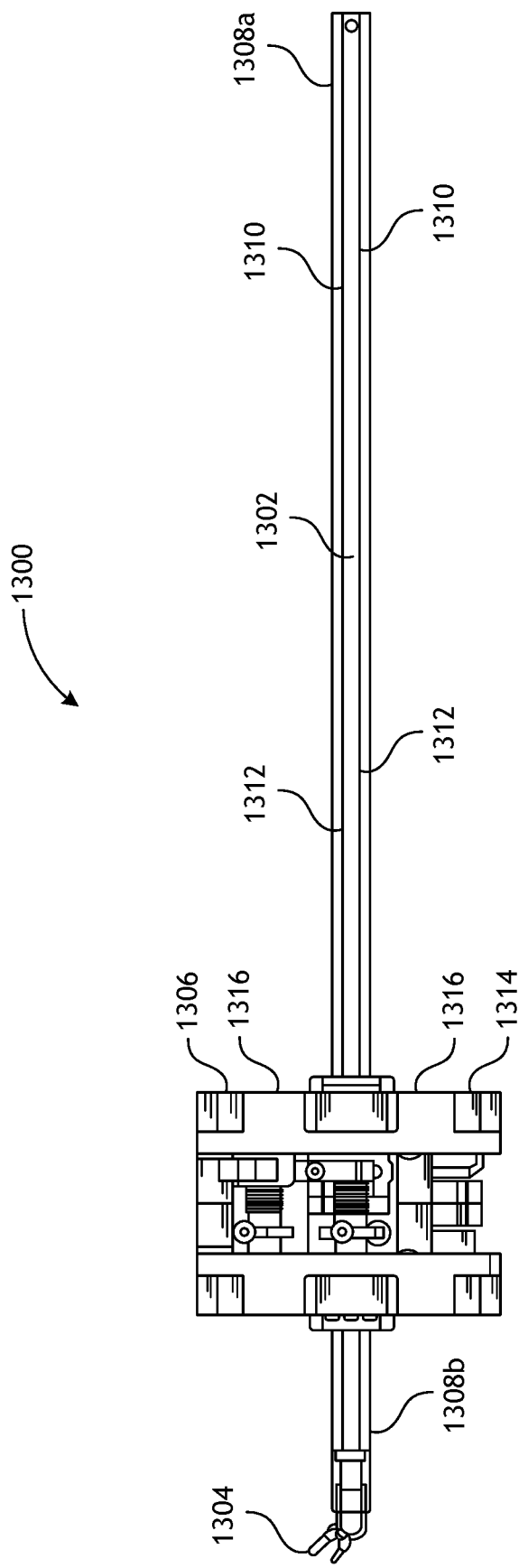
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
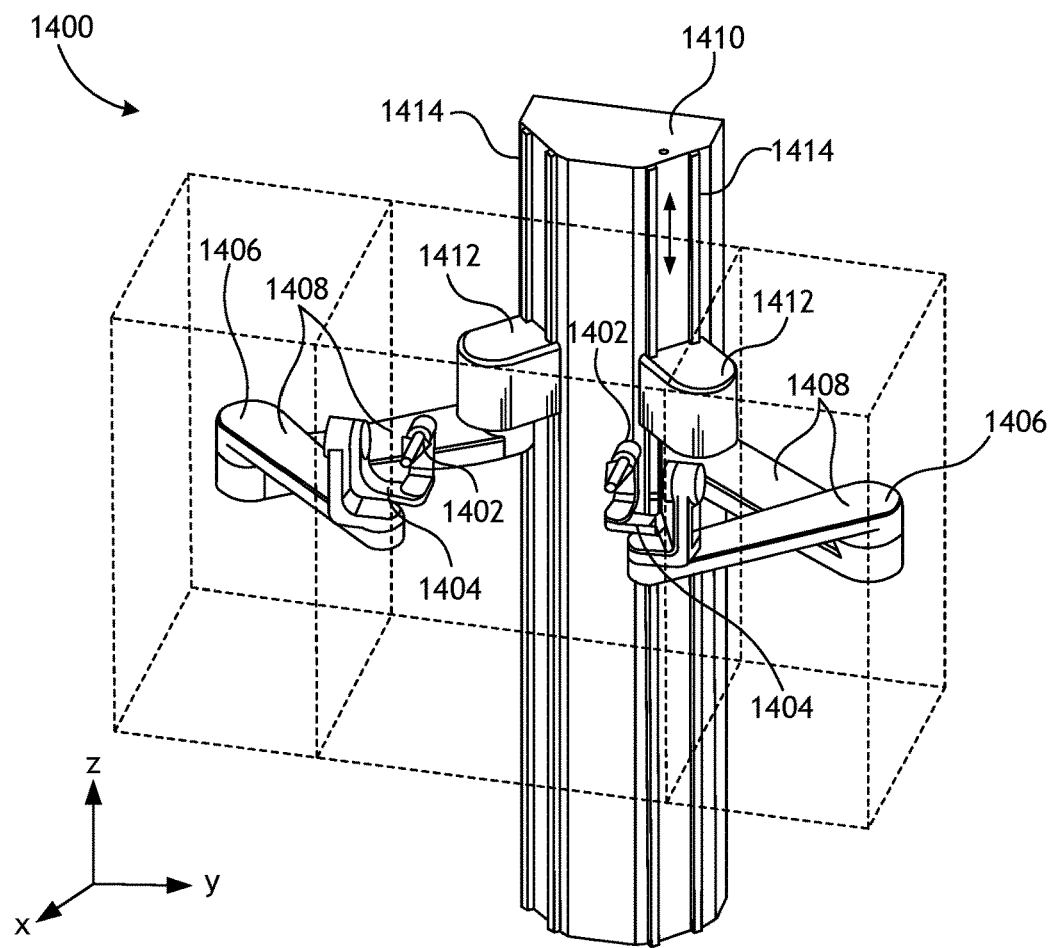
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
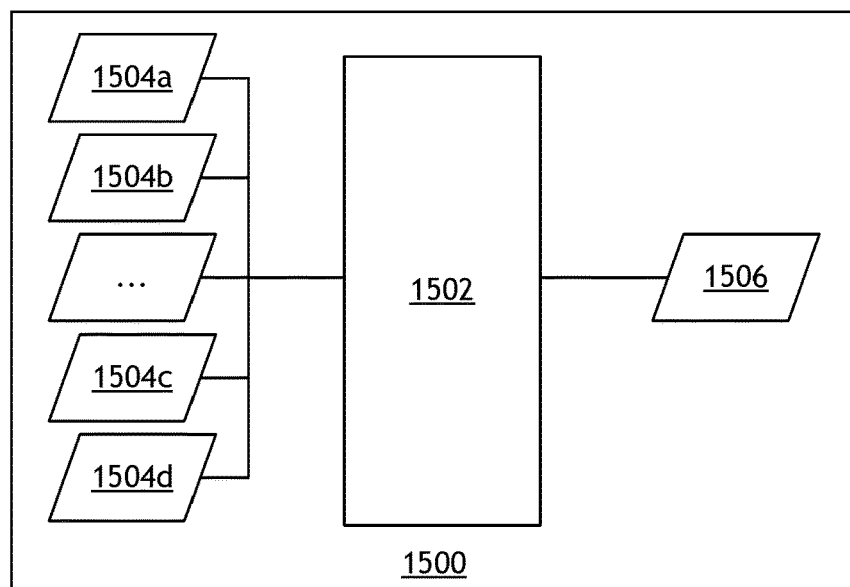
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description.

Figure 16:
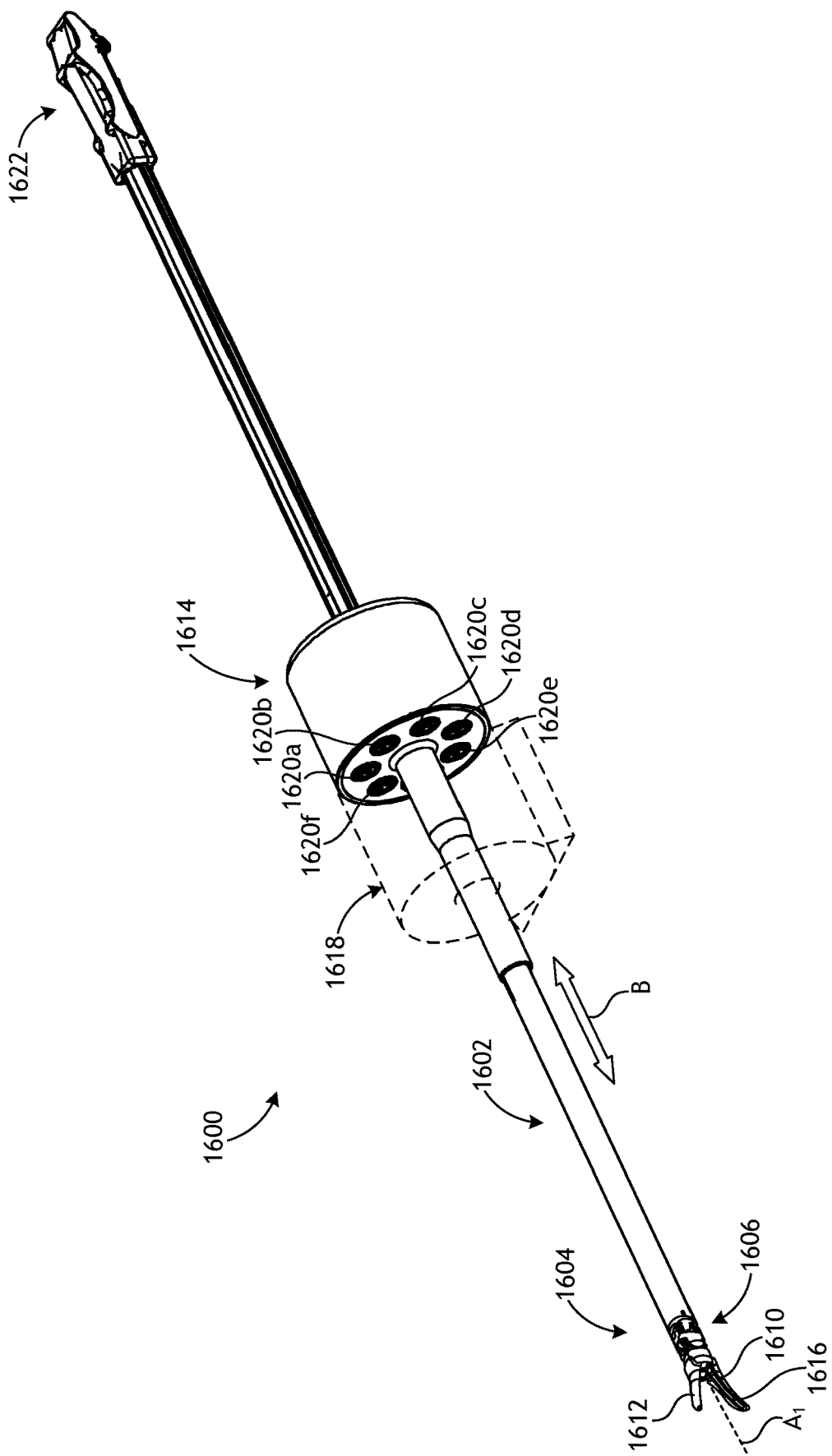
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments with opposing jaws such as, but not limited to, other types of surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods, such as a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 may be rotatable (pivotable) relative to the first jaw 1610 to actuate the end effector 1604 between an open, unclamped position and a closed, clamped position. In other embodiments, however, the first jaw 1610 may move (rotate) relative to the second jaw 1612 to move the jaws 1610, 1612 between open and closed positions. In yet other embodiments, as discussed in more detail below, both jaws 1610, 1612 may simultaneously move (e.g., bifurcating jaws) to move the jaws 1610, 1612 between open and closed positions.

In the illustrated example, the first jaw 1610 is referred to as a "cartridge" or "channel" jaw, and the second jaw 1612 is referred to as an "anvil" jaw. The first jaw 1610 includes a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing or "handle" 1614, and the shaft 1602 extends longitudinally through the handle 1614. The handle 1614 houses an actuation system designed to move the shaft 1602 relative to the handle 1614, and further designed to facilitate articulation of the wrist 1606 and actuation (operation) of the end effector 1604 (e.g., clamping, firing, rotation, articulation, energy delivery, etc.). More specifically, the systems and mechanisms housed within the handle 1614 are actuatable to move (translate) a plurality of drive members (mostly obscured in FIG. 16) that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

Selective actuation of one or more of the drive members, for example, may cause the shaft 1602 to translate relative to the handle 1614, as indicated by the arrows B, and thereby advance or retract the end effector 1602. Selective actuation of one or more other drive members may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" 1616 defined in the first jaw 1610. As it moves distally, the knife transects any tissue grasped between the opposing jaws 1610, 1612. Moreover, as the knife advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As will be appreciated, however, the end effector 1604 may be replaced with any of the other types of end effectors mentioned herein, and in those cases actuating the end effector 1604 may entail a variety of other actions or movements, without departing from the scope of the disclosure. For example, in some embodiments, the end effector 1604 may be replaced with a vessel sealer and actuating such an end effector 1604 may further entail triggering energy delivery (e.g., RF energy) to cauterize and/or seal tissue or vessels.

The handle 1614 provides or otherwise includes various coupling features that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the systems and mechanisms housed within the handle 1614 and thereby operate the surgical tool 1600. In the illustrated embodiment, the handle 1614 includes a first drive input 1620a, a second drive input 1620b, a third drive input 1620c, a fourth drive input 1620d, a fifth drive input 1620e, and a sixth drive input 1620f. While six drive inputs 1620a-f are depicted, more or less than six may be included in the handle 1614 depending on the application, and without departing from the scope of the disclosure.

Each drive input 1620a-f may be matable with a corresponding drive output (not shown) of the instrument driver 1618 such that movement (rotation) of a given drive output correspondingly moves (rotates) the associated drive input 1620a-f and thereby causes various operations of the surgical tool 1600.

In some embodiments, actuation of the first drive input 1620a may cause the knife to fire at the end effector 1604, thus advancing or retracting the knife, depending on the rotational direction of the first drive input 1620a. Actuation of the third drive input 1620c may cause the shaft 1602 to move (translate) relative to the handle 1614 along the longitudinal axis Al, depending on the rotational direction of the third drive input 1620c. In some embodiments, actuation of the second drive input 1620b may shift operation or activation within the handle 1614 between the first and third drive inputs 1620a,c. Consequently, actuation of the second drive input 1620b will dictate whether the knife is fired or whether the shaft 1602 is moved (translated). Actuation of the fourth drive input 1620d may lock and unlock z-axis translation of the shaft 1602, and actuation of the fifth drive input 1620e may cause articulation of the end effector 1604 at the wrist 1606. Lastly, actuation of the sixth drive input 1620f may cause the jaws 1610, 1612 to open or close, depending on the rotational direction of the sixth drive input 1620f. In some embodiments, actuation of the sixth drive input 1620f may operate a toggle mechanism 1622 arranged at the proximal end of the shaft 1602, and actuation of the toggle mechanism 1622 may cause the jaws 1610, 1612 to open and close.

Figure 17:
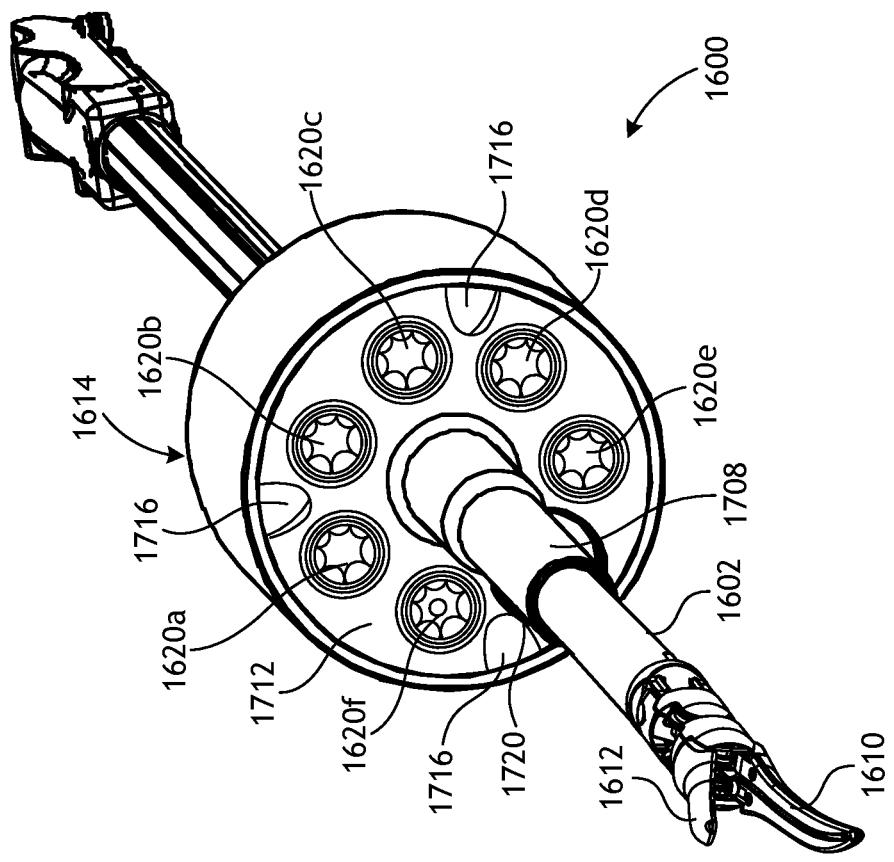
FIG. 17 depicts separated isometric end views of the instrument driver and the surgical tool of FIG. 16.
Figure 17:
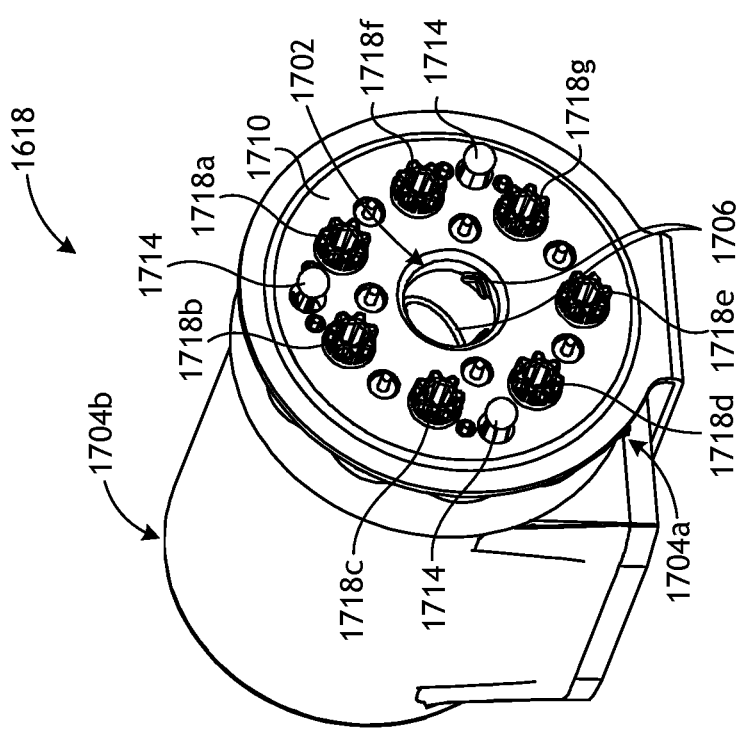

FIG. 17 depicts separated isometric end views of the instrument driver 1618 and the surgical tool 1600 of FIG. 16. With the jaws 1610, 1612 closed, the shaft 1602 and the end effector 1604 can penetrate the instrument driver 1618 by extending through a central aperture 1702 defined longitudinally through the instrument driver 1618 between first and second ends 1704a,b. In some embodiments, to align the surgical tool 1600 with the instrument driver 1618 in a proper angular orientation, one or more alignment guides 1706 may be provided or otherwise defined within the central aperture 1702 and configured to engage one or more corresponding alignment features (not shown) provided on the surgical tool 1600. The alignment feature(s) may comprise, for example, a protrusion or projection (not shown) defined on or otherwise provided by an alignment nozzle 1708 extending distally from the handle 1614. In one or more embodiments, the alignment guide(s) 1706 may comprise a curved or arcuate shoulder or lip configured to receive and guide the alignment feature as the alignment nozzle 1708 enters the central aperture 1702. As a result, the surgical tool 1600 is oriented to a proper angular alignment with the instrument driver 1618 as the alignment nozzle 1708 is advanced distally through the central aperture 1702. In other embodiments, the alignment nozzle 1708 may be omitted and the alignment feature 1712 may alternatively be provided on the shaft 1602, without departing from the scope of the disclosure.

A drive interface 1710 is provided at the first end 1704a of the instrument driver 1618 and is matable with a driven interface 1712 provided on the distal end of the handle 1614. The drive and driven interfaces 1710, 1712 may be configured to mechanically, magnetically, and/or electrically couple the handle 1614 to the instrument driver 1618. To accomplish this, in some embodiments, the drive and driven interfaces 1710, 1712 may provide one or more matable locating features configured to secure the handle 1614 to the instrument driver 1618. In the illustrated embodiment, for example, the drive interface 1710 provides one or more interlocking features 1714 (three shown) configured to locate and mate with one or more complementary-shaped pockets 1716 (two shown, one occluded) provided on the driven interface 1712. In some embodiments, the features 1714 may be configured to align and mate with the pockets 1716 via an interference or snap fit engagement, for example.

The instrument driver 1618 also includes one or more drive outputs that extend through the drive interface 1710 to mate with corresponding drive inputs 1620a-f provided at the distal end of the handle 1614. More specifically, the instrument driver 1618 includes a first drive output 1718a matable with the first drive input 1620a, a second drive output 1718b matable with the second drive input 1620b, a third drive output 1718b matable with the third drive input 1620c, a fourth drive output 1718d matable with the fourth drive input 1620d, a fifth drive output 1718e matable with the fifth drive input 1620e, and a sixth drive output 1718f matable with the sixth drive input 1620f. In some embodiments, as illustrated, the drive outputs 1718a-f may define splines or features designed to mate with corresponding splined receptacles of the drive inputs 1620a-f Once properly mated, the drive inputs 1620a-f will share axes of rotation with the corresponding drive outputs 1718a-f to allow the transfer of rotational torque from the drive outputs 1718a-f to the corresponding drive inputs 1620a-f. In some embodiments, each drive output 1718a-f may be spring loaded and otherwise biased to spring outwards away from the drive interface 1710. Each drive output 1718a-f may be capable of partially or fully retracting into the drive interface 1710.

In some embodiments, the instrument driver 1618 may include additional drive outputs, depicted in FIG. 17B as a seventh drive output 1718g. The seventh drive output 1718g may be configured to mate with additional drive inputs (not shown) of the handle 1614 to help undertake one or more additional functions of the surgical tool 1600. In the illustrated embodiment, however, the handle 1614 does not include additional drive inputs matable with the seventh drive output 1718g. Instead, the driven interface 1712 defines a corresponding recess 1720 (partially occluded) configured to receive the seventh drive output 1718g. In other applications, however, a seventh drive input (not shown) could be included in the handle 1614 to mate with the seventh drive output 1718g, or the surgical tool 1600 might be replaced with another surgical tool having a seventh drive input, which would be driven by the seventh drive output 1718g.

While not shown, in some embodiments, an instrument sterile adapter (ISA) may be placed at the interface between the instrument driver 1618 and the handle 1614. In such applications, the interlocking features 1714 may operate as alignment features and possible latches for the ISA to be placed, stabilized, and secured. Stability of the ISA may be accomplished by a nose cone feature provided by the ISA and extending into the central aperture 1702 of the instrument driver 1618. Latching can occur either with the interlocking features 1714 or at other locations at the interface. In some cases, the ISA will provide the means to help align and facilitate the latching of the surgical tool 1600 to the ISA and simultaneously to the instrument driver 1618.

Figure 18:
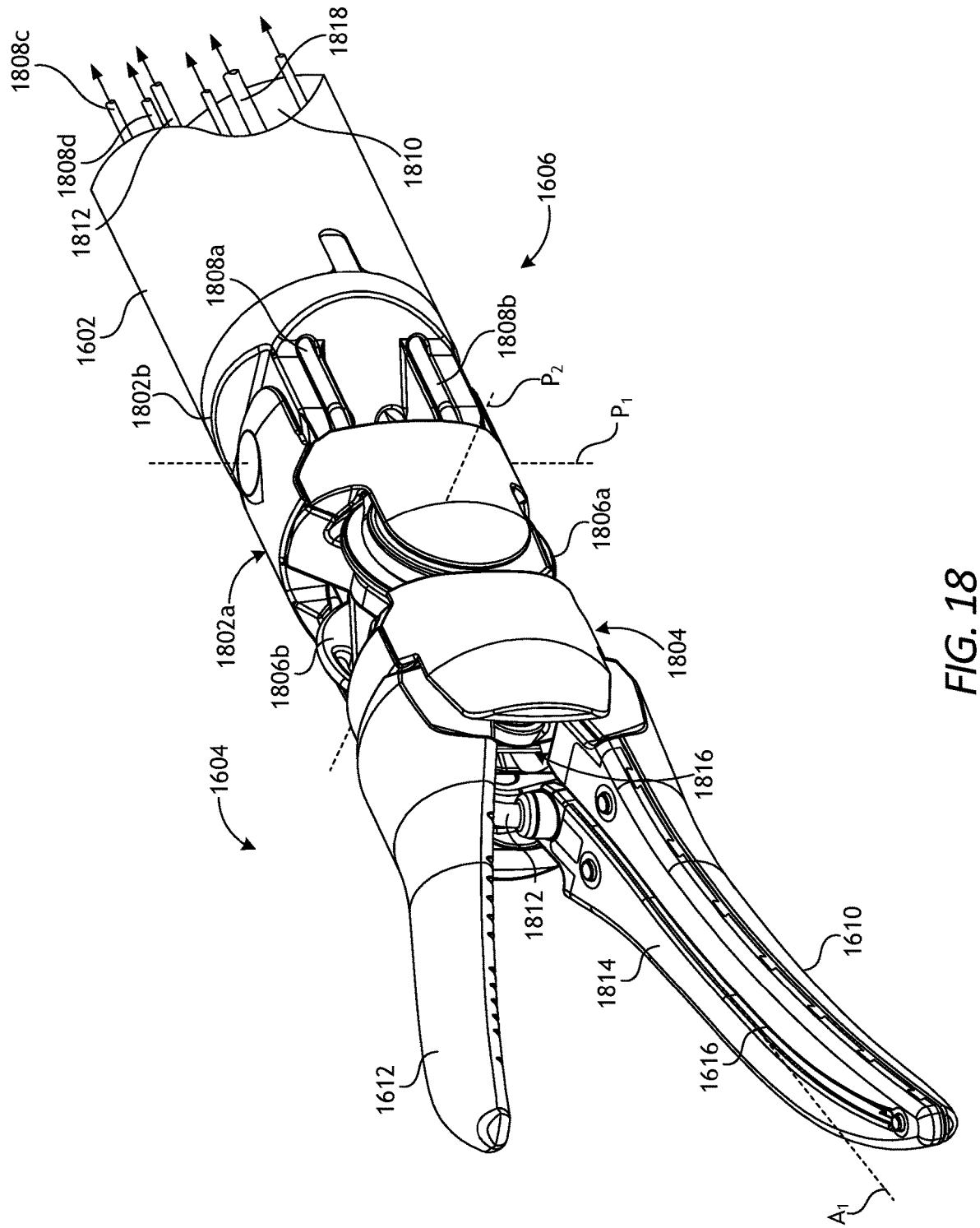
FIG. 18 is an enlarged isometric view of the distal end of the surgical tool of FIGS. 16 and 17, according to one or more embodiments.

Multi-Function Closing/Opening and Dissection/Sealing Enabled by Clevis Jaw Constraint of Jaws FIG. 18 is an enlarged isometric view of the distal end of the surgical tool 1600 of FIGS. 16 and 17. FIG. 18, however, depicts an enlarged view of an alternative embodiment of the end effector 1604 and the wrist 1606. In contrast to the end effector 1604 of FIGS. 16 and 17, which depicts a surgical stapler with the second jaw 1612 pivotable relative to the first jaw 1610 to open and close the jaws 1610, 1612, the end effector 1604 depicted in FIG. 18 is a vessel sealer where both jaws 1610, 1612 simultaneously move to actuate the jaws 1610, 1612 between open and closed positions, e.g., bifurcating jaws.

The wrist 1606 interposes the shaft 1602 and the end effector 1604 and thereby operatively couples the end effector 1604 to the shaft 1602. In some embodiments, however, a shaft adapter may be directly coupled to the wrist 1606 and otherwise interpose the shaft 1602 and the wrist 1606. Accordingly, the wrist 1606 may be operatively coupled to the shaft 1602 either through a direct coupling engagement where the wrist 1606 is directly coupled to the distal end of the shaft 1602, or an indirect coupling engagement where a shaft adapter interposes the wrist 1606 and the distal end of the shaft 1602. As used herein, the term "operatively couple" refers to a direct or indirect coupling engagement between two components.

To operatively couple the end effector 1604 to the shaft 1602, the wrist 1606 includes a first or "distal" clevis 1802a and a second or "proximal" clevis 1802b. The devises 1802*a,b* may alternatively be referred to herein as "articulation joints" of the wrist 1606 and extend from the shaft 1602, or alternatively a shaft adapter. As described herein, the devises 1802*a,b* are operatively coupled to facilitate articulation of the wrist 1606 relative to the shaft 1602. The wrist 1606 may also include a linkage 1804 arranged distal to the distal clevis 1802*a* and operatively mounted to the jaws 1610, 1612.

As illustrated, the proximal end of the distal clevis 1802*a* may be rotatably mounted to the proximal clevis 1802*b*. In some embodiments, for example, the proximal end of the distal clevis 1802*a* may be pivotably coupled to the proximal clevis 1802*b* at a first pivot axis $P_1$ of the wrist 1602. In other embodiments, however, the proximal end of the distal clevis 1802*a* may alternatively be rotatably coupled to the proximal clevis 1802*b*, such as in the "snake wrist" rotatable coupling between adjacent articulation joints (links) disclosed in U.S. Patent Pub. 2020/0093554, the contents of which are hereby incorporated by reference in their entirety. As will be appreciated, any of the wrists described or disclosed herein may alternatively, comprise a type of "snake wrist," without departing from the scope of the disclosure.

First and second pulleys 1806*a* and 1806*b* may be rotatably mounted to the distal end of the distal clevis 1802*a* at a second pivot axis $P_2$ of the wrist 1602. The linkage 1804 may be arranged distal to the second pivot axis $P_2$ and operatively mounted to the jaws 1610, 1612. The first pivot axis $P_1$ is substantially perpendicular (orthogonal) to the longitudinal axis $A_1$ of the shaft 1602, and the second pivot axis $P_2$ is substantially perpendicular (orthogonal) to both the longitudinal axis $A_1$ and the first pivot axis $P_1$. Movement of the end effector 1604 about the first pivot axis $P_1$ provides "yaw" articulation of the wrist 1606, and movement about the second pivot axis $P_2$ provides "pitch" articulation of the wrist 1606.

A plurality of drive members, shown as drive members 1808*a*, 1808*b*, 1808*c*, and 1808*d*, extend longitudinally within a lumen 1810 defined by the shaft 1602 (or a shaft adaptor) and extend at least partially through the wrist 1606. The drive members 1808*a-d* may form part of the actuation systems housed within the handle 1614 (FIGS. 16 and 17), and may comprise cables, bands, lines, cords, wires, woven wires, ropes, strings, twisted strings, elongate members, belts, shafts, flexible shafts, drive rods, or any combination thereof. The drive members 1808*a-d* can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof. While four drive members 1808*a-d* are depicted in FIG. 18, more or less than four may be employed, without departing from the scope of the disclosure.

The drive members 1808*a-d* extend proximally from the end effector 1604 and the wrist 1606 toward the handle 1614 (FIGS. 16 and 17) where they are operatively coupled to various actuation mechanisms or devices that facilitate longitudinal movement (translation) of the drive members 1808*a-d* within the lumen 1810. Selective actuation of the drive members 1808*a-d* applies tension (i.e., pull force) to the given drive member 1808*a-d* in the proximal direction, which urges the given drive member 1808*a-d* to translate longitudinally within the lumen 1810.

In the illustrated embodiment, the drive members 1808*a-d* each extend longitudinally through the proximal clevis 1802*b*. The distal end of each drive member 1808*a-d* terminates at the first or second pulleys 1806*a,b*, thus operatively coupling each drive member 1808*a-d* to the end effector 1604. In some embodiments, the distal ends of the first and second drive members 1808*a,b* may be coupled to each other and terminate at the first pulley 1806*a*, and the distal ends of the third and fourth drive members 1808*c,d* may be coupled to each other and terminate at the second pulley 1806*b*. In at least one embodiment, the distal ends of the first and second drive members 1808*a,b* and the distal ends of the third and fourth drive members 1808*c,d* may each be coupled together at a corresponding ball crimp (not shown) mounted to the first or second pulley 1806*a,b*, respectively.

In the illustrated embodiment, the drive members 1808*a-d* operate "antagonistically". More specifically, when the first drive member 1808*a* is actuated (moved), the second drive member 1808*b* naturally follows as coupled to the first drive member 1808*a*, and when the third drive member 1808*c* is actuated, the fourth drive member 1808*d* naturally follows as coupled to the third drive member 1808*c*, and vice versa. Antagonistic operation of the drive members 1808*a-d* can open or close the jaws 1610, 1612 and can further cause the end effector 1604 to articulate at the wrist 1606. More specifically, selective actuation of the drive members 1808*a-d* in known configurations or coordination can cause the end effector 1604 to articulate about one or both of the pivot axes $P_1$, $P_2$, thus facilitating articulation of the end effector 1604 in both pitch and yaw directions. Moreover, selective actuation of the drive members 1808*a-d* in other known configurations or coordination will cause the jaws 1610, 1612 to open or close. Antagonistic operation of the drive members 1808*a-d* advantageously reduces the number of cables required to provide full wrist 1606 motion, and also helps eliminate slack in the drive members 1808*a-d*, which results in more precise motion of the end effector 1604.

In the illustrated embodiment, the end effector 1604 is able to articulate (move) in pitch about the second or "pitch" pivot axis $P_2$, which is located near the distal end of the wrist 1606. Thus, the jaws 1610, 1612 open and close in the direction of pitch. Moving both articulation axes $P_1$, $P_2$ closer to the therapeutic jaw surface enables minimization of the distance between the remote center of motion, therapeutic surface and articulation axis. Having the pitch pivot axis $P_2$ as far distal as possible may be advantageous in providing a geometric advantage that helps an operator more easily get under vessels and facilitate touch and spread dissection. This may also reduce the overall length of the end effector 1604 and thereby improve surgeon access to patient anatomy during surgery by allowing articulate motion in smaller surgical spaces. This may improve the robotic control of the instrument making user applied motions seem more natural. This may also result in providing better reach to anatomy during dissection, such as for lymph node removal or other tissue mobilization. In other embodiments, however, the wrist 1606 may alternatively be configured such that the second pivot axis $P_2$ facilitates yaw articulation of the jaws 1610, 1612, without departing from the scope of the disclosure.

In some embodiments, an electrical conductor 1812 may also extend longitudinally within the lumen 1810, through the wrist 1606, and terminate at an electrode 1814 to supply electrical energy to the end effector 1604. In some embodiments, the electrical conductor 1812 may comprise a wire, but may alternatively comprise a rigid or semi-rigid shaft, rod, or strip (ribbon) made of a conductive material. The electrical conductor 1812 may be partially covered with an insulative covering (overmold) made of a non-conductive material. Using the electrical conductor 1812 and the electrode 1814, the end effector 1604 may be configured for monopolar or bipolar RF operation.

In the illustrated embodiment, the end effector 1604 comprises a combination tissue grasper and vessel sealer that includes a knife 1816 (mostly occluded), alternately referred to as a "cutting element" or "blade." The knife 1816 is aligned with and configured to traverse the guide track 1616 defined longitudinally in one or both of the upper and lower jaws 1610, 1612. The knife 1816 may be operatively coupled to the distal end of a drive rod 1818 that extends longitudinally within the lumen 1810 and passes through the wrist 1606. Longitudinal movement (translation) of the drive rod 1818 correspondingly moves the knife 1816 within the guide track(s) 1616. Similar to the drive members 1808a-d, the drive rod 1818 may form part of the actuation systems housed within the handle 1614 (FIGS. 16 and 17). Selective actuation of a corresponding drive input will cause the drive rod 1818 to move distally or proximally within the lumen 1810, and correspondingly move the knife 1816 in the same longitudinal direction.

Figure 19A:
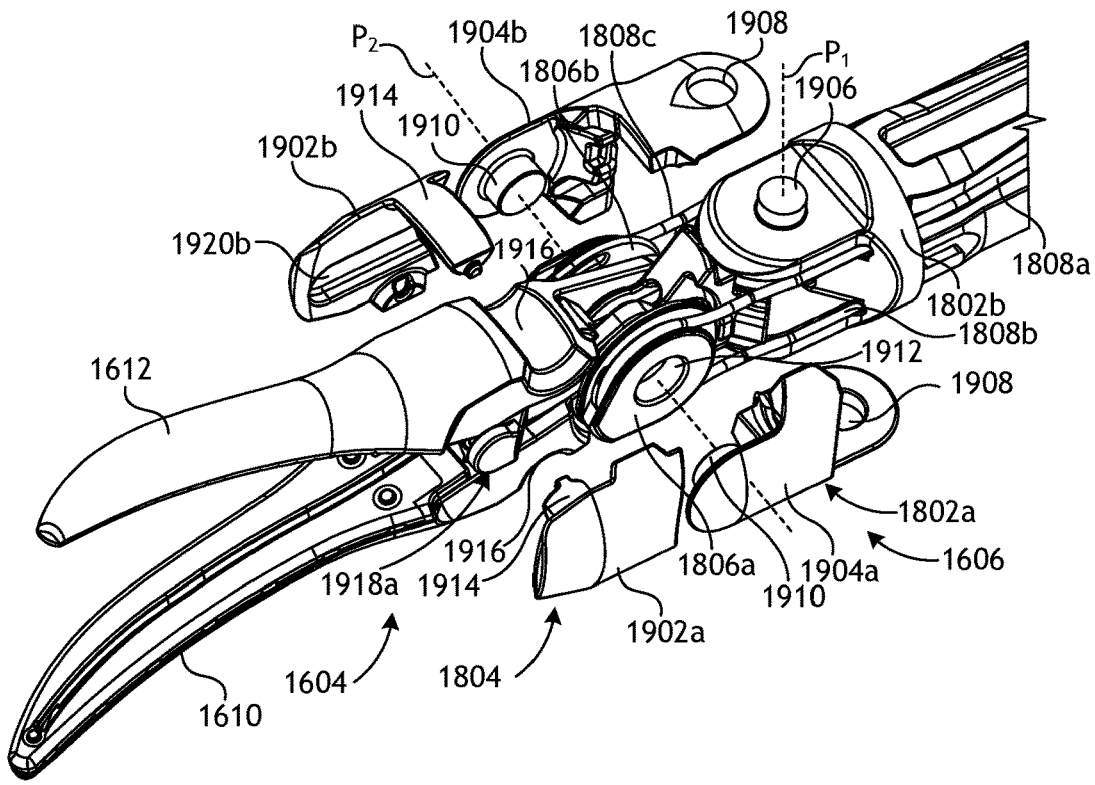
FIGS. 19A and 19B are isometric, partially exploded views of the end effector of FIG. 18 from right and left vantage points, according to one or more embodiments.
Figure 19B:
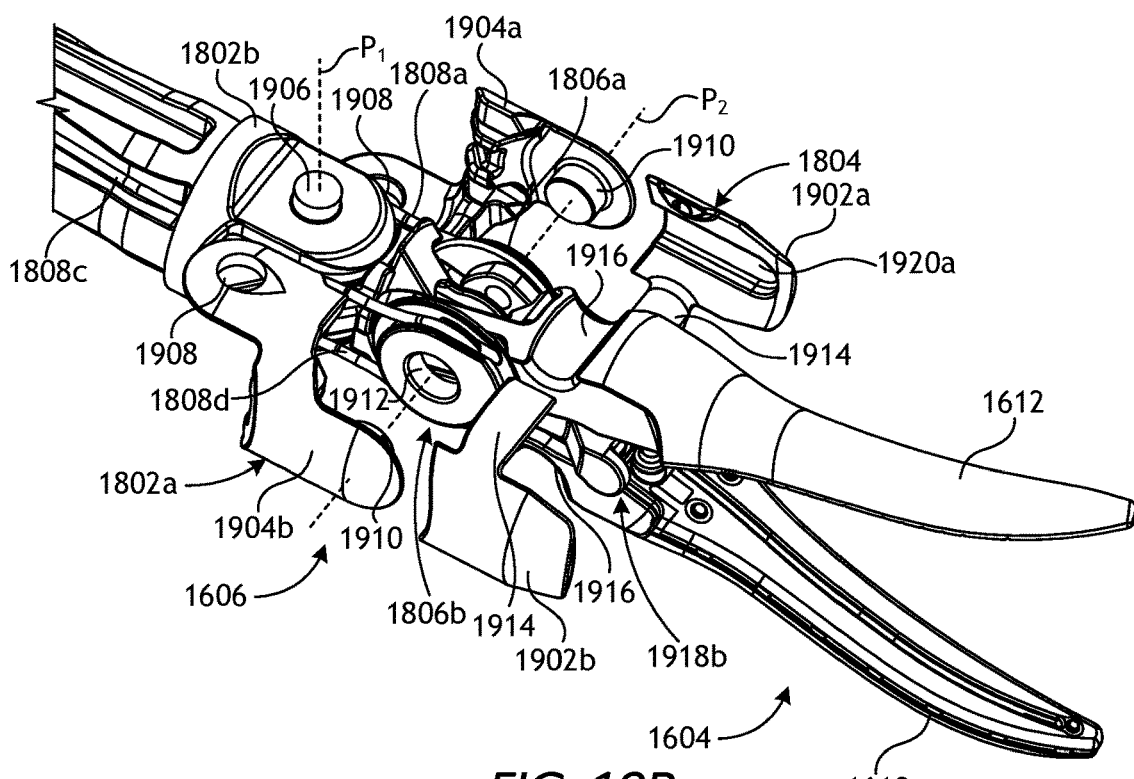

FIGS. 19A and 19B are isometric, partially exploded views of the end effector 1604 of FIG. 18, as taken from right and left vantage points. FIGS. 19A-19B depict the distal clevis 1802a and the linkage 1804 exploded laterally from the remaining portions of the end effector 1604 and the wrist 1606, thus exposing the distal ends of drive members 1808a-d terminating at the pulleys 1806a,b.

In some embodiments, one or both of the distal clevis 1802a and the linkage 1804 may comprise two or more component parts that are joined to help form the wrist 1606 and rotatably secure the jaws 1610, 1612 to the wrist 1606. In the illustrated embodiment, for example, the linkage 1804 comprises opposing first and second linkage portions 1902a, b, and the distal clevis 1802a comprises opposing first and second distal clevis portions 1904a,b. In building the wrist 1606, joining the linkage portions 1902a,b and joining the distal clevis portions 1904a,b may help rotatably secure the jaws 1610, 1612 to the wrist 1606 and may further secure the pulleys 1806a,b and other component parts within the wrist 1606. The linkage portions 1902a,b and the distal clevis portions 1904a,b may be joined, respectively, by welding, soldering, brazing, an adhesive, an interference fit, or by using one or more mechanical fasteners, such as pins, rivets, bolts, or any combination of the foregoing. In other embodiments, however, it is contemplated herein that one or both of the devises 1802a,b may alternatively comprise a monolithic, one-piece structure, without departing from the scope of the disclosure.

As indicated above, the proximal end of the distal clevis 1802a may be rotatably mounted to the proximal clevis 1802b at the first pivot axis $P_1$ of the wrist 1602. As illustrated, the proximal clevis 1802b may provide or otherwise define one or more pins 1906 (one shown) and the distal clevis 1802a may provide or define one or more corresponding apertures 1908 matable with the pins 1906. Mating the aperture(s) 1908 with the pin(s) 1906 may allow the wrist 1606 to articulate in "yaw" about the first pivot axis $P_1$. In alternative embodiments, however, the pin(s) 1906 may be provided by the distal clevis 1802a, and the aperture (s) 1908 may be provided by the proximal clevis 1802b, without departing from the scope of the disclosure. Moreover, in some embodiments, the aperture(s) 1908 need not be through-holes, as depicted, but could alternatively comprise recesses defined in the distal clevis 1802a (or the proximal clevis 1802b) and sized and otherwise configured to receive the pin(s) 1906.

As also indicated above, the first and second pulleys 1806a and 1806b may be rotatably mounted to the distal end of the distal clevis 1802a at the second pivot axis $P_2$ of the wrist 1602. As illustrated, the distal clevis 1802a may provide or otherwise define opposing pins 1910 and the pulleys 1806a,b may each define an aperture 1912 sized to receive or mate with the corresponding pin 1910. In alternative embodiments, however, the pins 1910 may be provided by the pulleys 1806a,b, and the apertures 1912 may be provided by the distal clevis 1802a, without departing from the scope of the disclosure. Moreover, in some embodiments, the apertures 1912 need not be through-holes, as depicted, but could alternatively comprise recesses defined in the pulleys 1806a,b (or the distal clevis 1802a) and sized and otherwise configured to receive the pins 1910.

As further indicated above, the linkage 1804 may be mounted or otherwise operatively coupled to the jaws 1610, 1612. As illustrated, the linkage 1804 may provide or define one or more lateral arms 1914 and the jaws 1610, 1612 may define a corresponding one or more grooves 1916 configured to receive the lateral arms 1914 and provide corresponding jaw pivot surfaces for the jaws 1610, 1612. In the illustrated embodiment, one lateral arm 1914 is received within a groove 1916 defined by the first jaw 1610, and the other lateral arm 1914 is received within a groove 1916 defined by the second jaw 1612. Receiving the lateral arms 1914 in the grooves 1916 creates a jaw pivot point where the jaws 1610, 1612 are able to pivot between the open and closed positions. The lateral arms 1914 interact with the corresponding grooves 1916 and help prevent the jaws 1610, 1612 from separating from each other. In some embodiments, the lateral arms 1914 slidably engage the grooves 1916 as the jaws 1610, 1612 open and close about the jaw pivot point, thus the grooves 1916 may operate as corresponding cam surfaces. The jaw pivot points created by interaction between the lateral arms 1914 and the grooves 1916 may be substantially parallel to the second pivot axis $P_2$.

The wrist 1606 may further provide a jaw constraint that prevents the jaws 1610, 1612 from rotating out of alignment with each other as the jaws 1610, 1612 open and close. In the illustrated embodiment, the jaw constraint includes one or more alignment arms, shown as a first alignment arm 1918a (FIG. 19A) and a second alignment arm 1918b (FIG. 19B). As described in more detail below, the proximal end of the first alignment arm 1918a may be coupled (e.g., pinned) to the first pulley 1806a, and the proximal end of the second alignment arm 1918b may be coupled (e.g., pinned) to the second pulley 1806b, such that movement (rotation) of the pulleys 1806a,b correspondingly moves the alignment arms 1918a,b, respectively. In contrast, the distal end of the first alignment arm 1918a may be received within a first slot 1920a (FIG. 19B) defined in the first linkage portion 1902a of the linkage 1804, and the distal end of the second alignment arm 1918b may be received within a second slot 1920b (FIG. 19A) defined in the second linkage portion 1902b of the linkage 1804.

As the pulleys 1806a,b rotate to move the jaws 1610, 1612 between the open and closed positions, as described below, the distal ends of the alignment arms 1918a,b will correspondingly be urged to rotatably slide within the corresponding slots 1920a,b, respectively. Without the jaw constraint provided by the alignment arms 1918a,b and the corresponding slots 1920a,b, the jaws 1610, 1612 would tend to rotate out of alignment during opening and closing, thus preventing accurate positioning during opening and closing. This jaw condition is sometimes referred to as extreme backlash or slop.

Figure 20A:
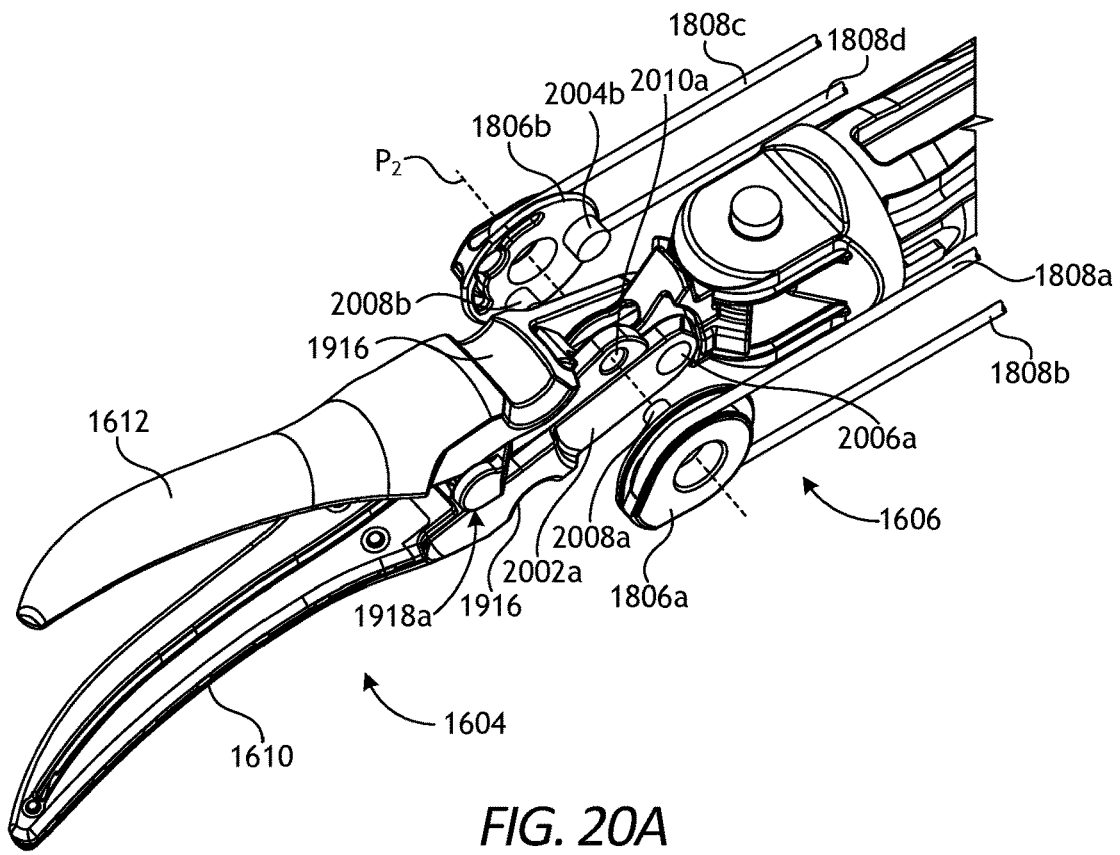
FIGS. 20A and 20B are additional isometric, partially exploded views of the end effector of FIG. 18 from the right and left vantage points.
Figure 20B:
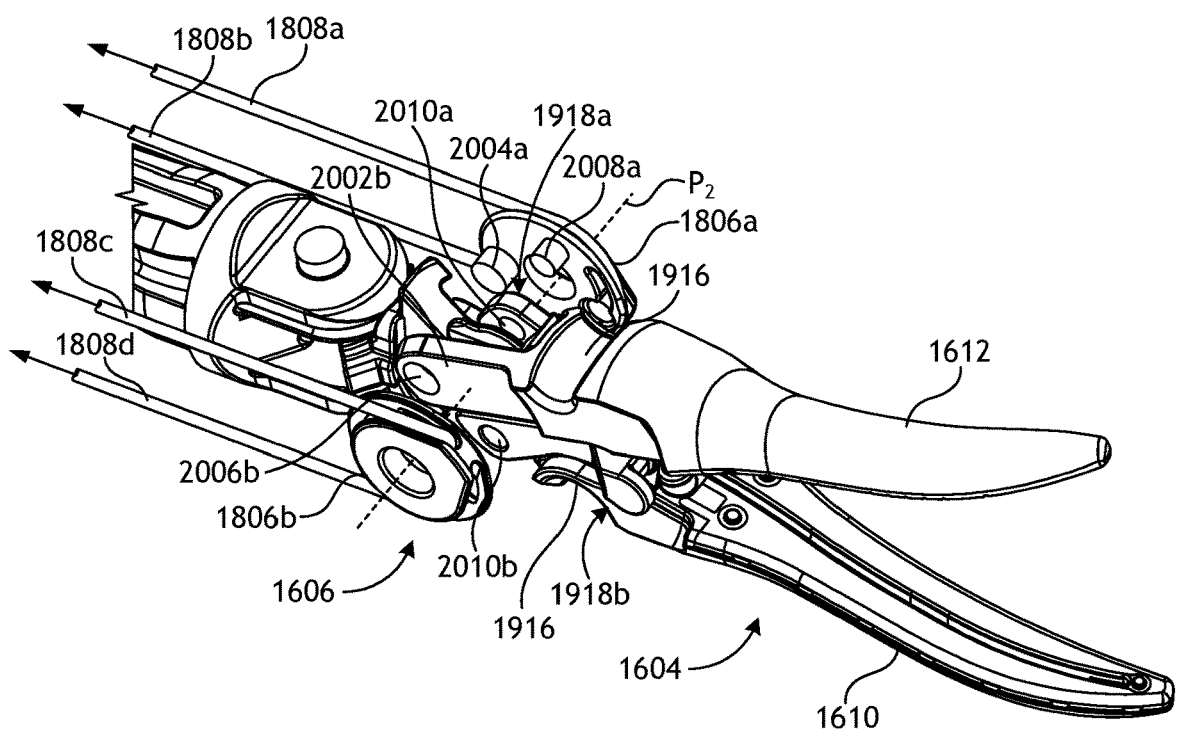

FIGS. 20A and 20B are additional isometric, partially exploded views of the end effector 1604 of FIG. 18 from the right and left vantage points. In FIGS. 20A-20B, the distal and proximal devises 1802a,b (FIGS. 19A-19B) are removed (omitted) for simplicity, and the first and second pulleys 1806a,b and the drive members 1808a-d are shown exploded laterally from the remaining portions of the end effector 1604 and the wrist 1606.

As illustrated, the first jaw 1610 provides a first jaw extension 2002a (FIG. 20A) and the second jaw 1612 provides a second jaw extension 2002b (FIG. 20B), and each jaw extension 2002a,b extends proximally from the corresponding jaws 1610, 1612. The first jaw extension 2002a may be rotatably coupled (e.g., pinned) to the first pulley 1806a such that movement (rotation) of the first pulley 1806a correspondingly moves the first jaw 1610 to pivot about the jaw pivot point, and the second jaw extension 2002b may be rotatably coupled (e.g. pinned) to the second pulley 1806b such that movement (rotation) of the second pulley 1806b correspondingly moves the second jaw 1612 to pivot about the jaw pivot point.

In the illustrated embodiment, the first pulley 1806a may provide or define a first jaw pin 2004a (FIG. 20B) configured to mate with a first jaw aperture 2006a (FIG. 20A) defined on the first jaw extension 2002a, and the second pulley 1806b may provide or define a second jaw pin 2004b (FIG. 20A) configured to mate with a second jaw aperture 2006b (FIG. 20B) defined on the second jaw extension 2002b. The first and second jaw pins 2004a,b are eccentric to the second pivot axis $P_2$. Consequently, mating the first and second jaw pins 2004a,b with the first and second jaw apertures 2006a,b, respectively, allows the pulleys 1806a,b to rotate about the second pivot axis $P_2$ to pivot the jaws 1610, 1612 about the jaw pivot points and between the open and closed positions, as constrained by the lateral arms 1914 (FIGS. 19A-19B).

In an alternative embodiment, the first and second jaw pins 2004a,b may be provided on the first and second jaw extensions 2002a,b, respectively, and the first and second jaw apertures 2006a,b may be provided on the pulleys 1806a,b, respectively, or any combination thereof. Moreover, the jaw apertures 2006a,b need not be through-holes, as depicted, but could alternatively comprise recesses defined in the jaw extensions 2002a,b (or the pulleys 1806a,b) and sized and otherwise configured to receive the jaw pins 2004a,b.

As mentioned above, the first and second alignment arms 1918a,b may also be rotatably coupled (e.g., pinned) to the first and second pulleys 1806a,b, respectively, such that movement (rotation) of the pulleys 1806a,b correspondingly moves the alignment arms 1918a,b. In the illustrated embodiment, for example, the first pulley 1806a may provide or define a first arm pin 2008a configured to mate with a first arm aperture 2010a defined by the first alignment arm 1918a, and the second pulley 1806b may provide or define a second arm pin 2008b (FIG. 20A) configured to mate with a second arm aperture 2010b (FIG. 20B) defined by the second alignment arm 1918b (FIG. 20B). Similar to the first and second jaw pins 2004a,b, the first and second arm pins 2008a,b are eccentric to the second pivot axis $P_2$, and the arm pins 2008a,b are also angularly offset from the first and second jaw pins 2004a,b. Consequently, as the pulleys 1806a,b rotate about the second pivot axis $P_2$, the alignment arms 1918a,b are moved and the distal ends of the alignment arms 1918a,b are urged to slide within (traverse) the corresponding slots 1920a,b (FIGS. 19A-19B), respectively. This helps maintain the jaws 1610, 1612 moving distally and/or proximally in a straight line during closing and opening (i.e., axial constraint), instead of rotating about the jaw pins 2004a,b.

In an alternative embodiment, the first and second arm pins 2008a,b may be provided on the alignment arms 1918a,b, respectively, and the first and second arm apertures 2010a,b may be provided on the pulleys 1806a,b, respectively, or any combination thereof, without departing from the scope of the disclosure. Moreover, the arm apertures 2010a,b need not be through-holes, as depicted, but could alternatively comprise recesses defined in the alignment arms 1918a,b (or the pulleys 1806a,b) and sized and otherwise configured to receive the arm pins 2008a,b.

As indicated above, selective actuation and antagonistic operation of the drive members 1808a-d can open or close the jaws 1610, 1612. Because the jaws 1610, 1612 are pinned to the pulleys 1806a,b and pivotally constrained at the jaw pivot point by the lateral arms 1914 (FIGS. 19A-19B) at the grooves 1916, as generally described above, selectively actuating the drive members 1808a-d such that the pulleys 1806a,b rotate in opposite angular directions may result in the jaws 1610, 1612 opening or closing. Simultaneously pulling proximally on the first and fourth drive members 1808a,d, for example, while allowing the second and third drive members 1808b,c to pay out slack, will cause the pulleys 1806a,b to rotate in first opposing directions and thereby cause the jaws 1610, 1612 to move (pivot) toward the closed position. In contrast, simultaneously pulling proximally on the second and third drive members 1808b,c while allowing the first and fourth drive members 1808a,d to pay out slack, will cause the pulleys 1806a,b to rotate in second opposing directions opposite the first opposing directions and thereby cause the jaws 1610, 1612 to move (pivot) toward the open position.

As also indicated above, selective actuation and antagonistic operation of the drive members 1808a-d may also cause the end effector 1604 to articulate at the wrist 1606 in both pitch and yaw directions. Again, because the jaws 1610, 1612 are pinned to the pulleys 1806a,b and pivotally constrained at the jaw pivot point by the lateral arms 1914 (FIGS. 19A-19B) at the grooves 1916, selectively actuating the drive members 1808a-d such that the pulleys 1806a,b rotate in the same angular direction may result in the jaws 1610, 1612 pivoting about the second pivot axis $P_2$ and thereby moving the end effector 1604 up or down in pitch. More specifically, simultaneously pulling on the first and third drive members 1808a,c while allowing the second and fourth drive members 1808b,d to pay out slack may cause the pulleys 1808a,b to rotate in a first angular direction and thereby pivot the end effector 1604 about the second pivot axis $P_2$ in upward pitch. In contrast, simultaneously pulling on the second and fourth drive members 1808b,d while allowing the first and third drive members 1808a,c to pay out will cause the pulleys 1808a,b to rotate in a second angular direction opposite the first angular direction and thereby pivot the end effector 1604 about the second pivot axis $P_2$ in downward pitch.

Furthermore, selective actuation of a first connected pair of drive members 1808a-d while relaxing a second pair of connected drive members 1808a-d may cause the end effector 1604 to pivot about the first pivot axis $P_1$ and thereby move in yaw. More specifically, pulling on the first and second drive members 1808a,b while simultaneously slackening the third and fourth drive members 1808c,d (e.g., allowing the third and fourth drive members 1808*c,d* to pay out) will pivot the end effector 1604 in yaw in a first direction. In contrast, pulling on the third and fourth drive members 1808*c,d* while simultaneously slackening the first and second drive members 1808*a,b* (e.g., allowing the first and second drive members 1808*a,b* to pay out) will pivot the end effector 1604 in yaw in a second direction opposite the first direction.

Figure 21A:
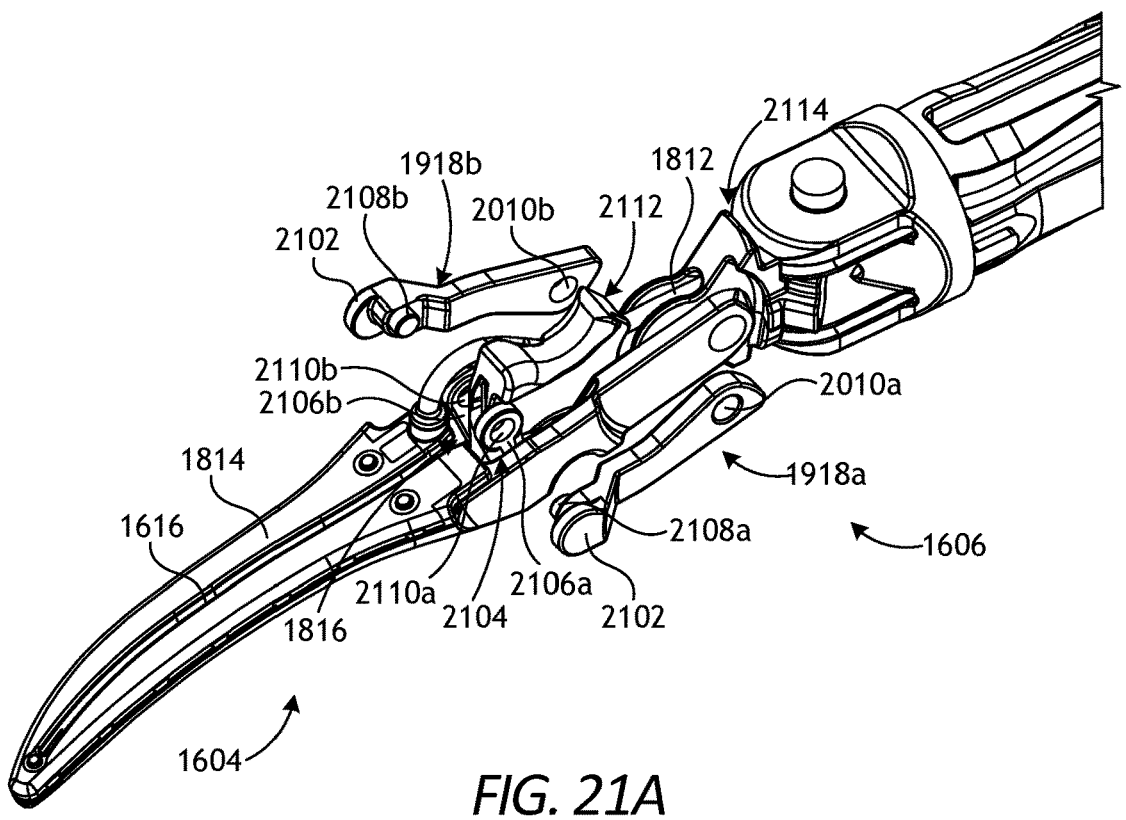
FIGS. 21A and 21B are additional isometric, partially exploded views of the end effector of FIG. 18 from the right and left vantage points.
Figure 21B:
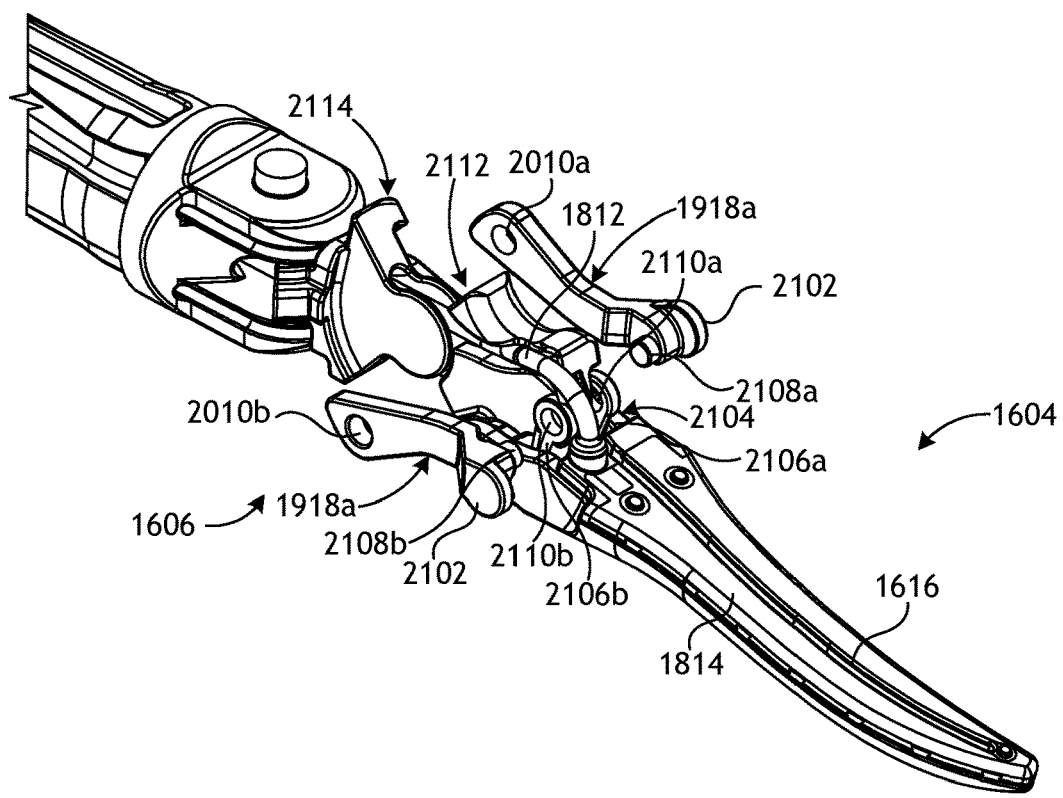

FIGS. 21A and 21B are additional isometric, partially exploded views of the end effector 1604 of FIG. 18 from the right and left vantage points. In FIGS. 21A-21B, the distal clevis 1802*a*, the linkage 1804 (FIGS. 19A-19B), the drive members 1808*a-d* (FIGS. 20A-20B), the pulleys 1806*a,b* (FIGS. 20A-20B), and the first or "upper" jaw 1612 are all removed (omitted) for simplicity. The first and second alignment arms 1918*a,b* are shown in FIGS. 21A-21B exploded laterally from the remaining portions of the end effector 1604 and the wrist 1606.

In some embodiments, as illustrated, each alignment arm 1918*a,b* may provide or otherwise define a head 2102 configured or otherwise sized to be received within the corresponding slot 1920*a,b* (FIGS. 19A-19B) defined in the linkage 1804 (FIGS. 19A-19B). The head 2102 may be provided at or near the distal end of each alignment arm 1918*a,b*, but may alternatively be arranged at any location along the alignment arm 1918*a,b* and distal to the arm apertures 2010*a,b*.

The wrist 1606 may further include an alignment link 2104 that forms part of the jaw constraint mentioned above. The alignment link 2104 may comprise a generally U-shaped (e.g., horseshoe shaped) member having opposing first and second link extensions 2106*a,b* configured to rotatably couple to the first and second alignment arms 1918*a,b*, respectively, and thereby help maintain the axial position of each alignment arm 1918*a,b* with respect to the opposing alignment arm 1918*a,b*. More specifically, the first alignment arm 1918*a* may provide or define a first link pin 2108*a* configured to be received within a corresponding first link aperture 2110*a* defined in the first link extension 2106*a*, and the second alignment arm 1918*b* may provide or define a second link pin 2108*b* configured to be received within a corresponding second link aperture 2110*b* defined in the second link extension 2106*b*. Mating the first and second link pins 2108*a,b* with the first and second link apertures 2110*a,b* effectively couples the first alignment arm 1918*a* to the second alignment arm 1918*b* for mutual movement as the alignment arms 1918*a,b* translate within the corresponding slots 1920*a,b* (FIGS. 19A-19B), respectively, as the pulleys 1806*a,b* (FIGS. 20A-20B) rotate.

In an alternative embodiment, the first and second link pins 2108*a,b* may be provided on the alignment links 2104 and the first and second link apertures 2110*a,b* may be provided on the alignment arms 1918*a,b*, or any combination thereof. Moreover, the link apertures 2110*a,b* need not be through-holes, as depicted, but could alternatively comprise recesses defined in the link extensions 2106*a,b* (or the alignment arms 1918*a,b*) and sized and otherwise configured to receive the link pins 2108*a,b*.

Accordingly, the jaw constraint may help prevent the jaws 1610, 1612 from rotating out of alignment with each other as the jaws 1610, 1612 open and close. More specifically, because the jaws 1610, 1612 are eccentrically pinned to the pulleys 1806*a,b*, as generally described above, rotating the pulleys 1806*a,b* about the second pivot axis $P_2$ will cause the jaws 1610, 1612 to move (translate) distally or proximally, depending on the rotational direction of the pulleys 1806*a,b*. The jaw constraint helps prevent the jaws 1610, 1612 from rotating about the jaw pins 2004*a,b* as the jaws axially translate. During example operation, as the pulleys 1806*a,b* rotate to open or close the jaws 1610, 1612, the heads 2102 of the alignment arms 1918*a,b* translate within the slots 1920*a,b* (FIGS. 19A-19B), and during this motion, any rotational torque that may be imparted to the jaws 1610, 1612 by rotation about the jaw pins 2004*a,b* will be assumed by the linkage 1804 (FIGS. 19A-19B) at the slots 1920*a,b*, and thus helping to prevent the jaws 1610, 1612 from rotating about the jaw pins 2004*a,b* as the jaws axially translate and open or close.

The alignment link 2104 may be fixed or free as arranged within the wrist 1606. The general U-shape of the alignment link 2104 may prove advantageous in allowing the wrist 1606 to be generally open through its central portions (e.g., middle). As a result, the wrist 1606 may be capable of accommodating the knife 1816 (occluded in FIG. 21B) and the drive rod 1818 (FIG. 18) through the middle of the wrist 1606 such that the knife 1816 can be received within the guide track 1616 upon firing the end effector 1604. In some embodiments, the open central portions of the wrist 1606 may also accommodate the electrical conductor 1812, which terminates at the electrode 1814.

In the illustrated embodiment, the wrist 1606 may further include a distal wedge 2112 and a mid-articulation insert 2114 arranged in series and positioned in the central portion or middle of the wrist 1606. The distal wedge 2112 may be arranged between the electrode 1814 and the distal clevis 1802*a* (FIGS. 19A-19B) and generally arranged within the linkage 1804 (FIGS. 18 and 19A-19B), and the mid-articulation insert 2114 may be generally arranged within the distal clevis 1802*a* (FIGS. 18 and 19A-19B). The distal wedge 2112 and the mid-articulation insert 2114 may be positioned between (interpose) the first and second jaw extensions 2102*a,b* of the jaws 1610, 1612. The distal wedge 2112 and mid-articulation insert 2114 may act to guide the jaw extensions 2102*a,b* in planar rotation as the jaws 1610, 1612 open, close, and articulate in pitch. The distal wedge 2112 further acts between the jaws 1610, 1612 during spread dissection, where the jaws 1610, 1612 are placed between tissue planes or through an aperture in tissue, and then opened to separate tissue. In some embodiments, the distal wedge 2112 and the mid-articulation insert 2114 may receive and help guide one or both of the knife 1816 and the electrical conductor 1812 to the jaws 1610, 1612. In at least one embodiment, as illustrated, the distal wedge 2112 may also extend partially through the alignment link 2104 and between the first and second link extensions 2106*a,b*.

Figure 22:
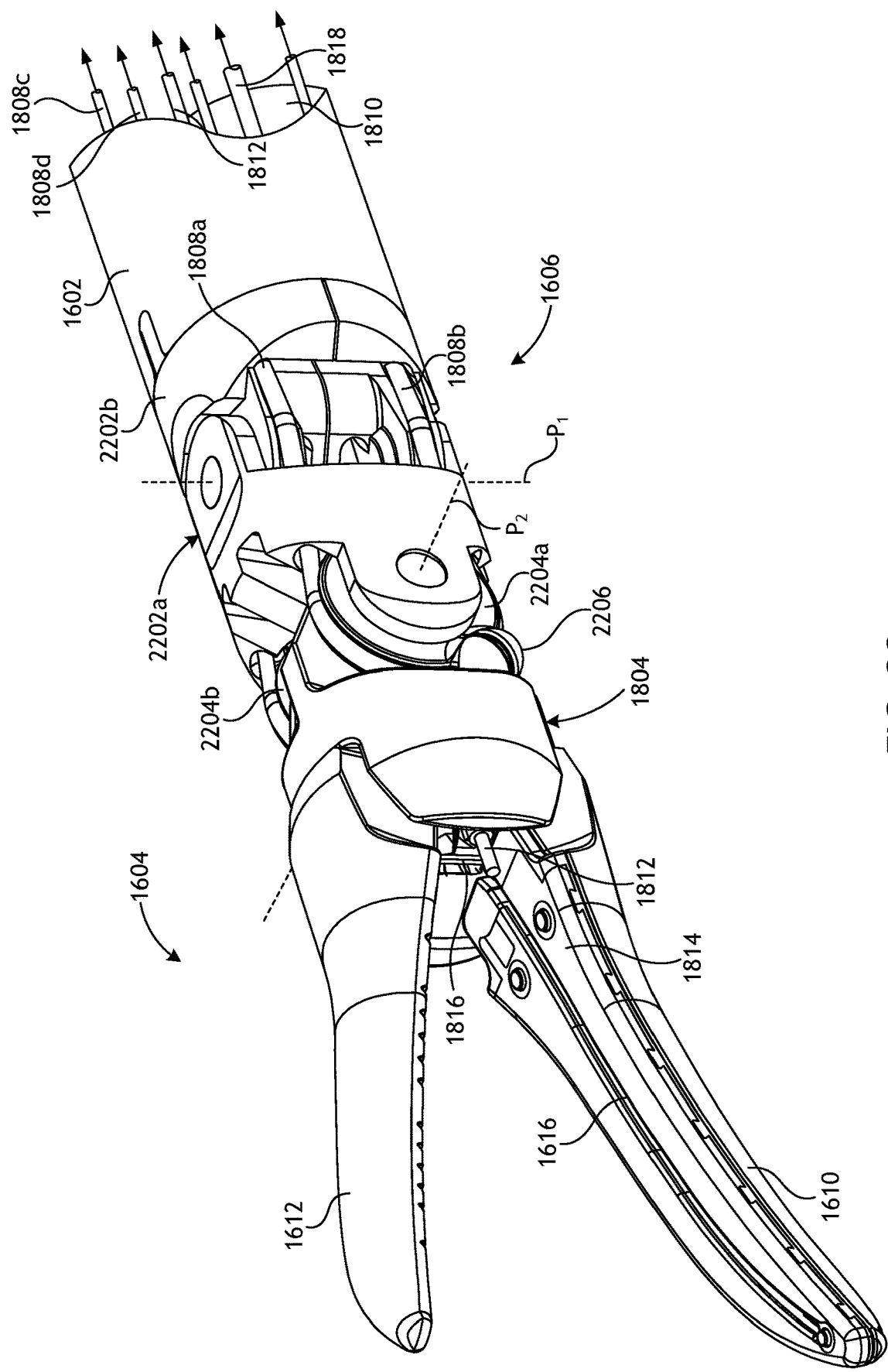
FIG. 22 is an enlarged isometric view of the distal end of the surgical tool of FIGS. 16 and 17, according to one or more additional embodiments.

FIG. 22 is another enlarged isometric view of the distal end of the surgical tool 1600 of FIGS. 16 and 17. More specifically, FIG. 22 depicts an enlarged view of an alternative embodiment of the end effector 1604 and the wrist 1606. The end effector 1604 may be similar in some respects to the end effector 1604 depicted in FIGS. 18, 19A-19B, 20A-20B, and 21A-21B and, therefore, may be best understood with reference thereto, where like numerals indicated similar components not described again in detail. Similar to the end effector of FIG. 18, for example, the end effector 1604 depicted in FIG. 22 is a vessel sealer where both jaws 1610, 1612 simultaneously move to actuate the jaws 1610, 1612 between open and closed positions, e.g., bifurcating jaws.

Moreover, the wrist 1606 includes a first or "distal" clevis 2202*a*, a second or "proximal" clevis 2202*b*, and the linkage 1804. The devises 2202*a,b* may be alternatively referred to herein as "articulation joints" of the wrist 1606 and extend in series. The devises 1802*a,b* are operatively coupled to facilitate articulation of the wrist 1606 relative to the shaft 1602. As illustrated, the proximal end of the distal clevis 2202a may be rotatably mounted to the proximal clevis 2202b at the first pivot axis $P_1$, and first and second pulleys 2204a and 2204b may be rotatably mounted to the distal end of the distal clevis 2202a at the second pivot axis $P_2$. The linkage 1804 may be arranged near the distal end of distal clevis 2202a and operatively coupled or mounted to the jaws 1610, 1612.

The drive members 1808a-d extend longitudinally within the lumen 1810 and extend at least partially through the wrist 1606. In the illustrated embodiment, the drive members 1808a-d each extend longitudinally through the proximal clevis 2202b. The distal end of each drive member 1808a-d terminates at the first or second pulleys 2204a,b, thus operatively coupling each drive member 1808a-d to the end effector 1604. In some embodiments, distal ends of the first and second drive members 1808a,b may be coupled to each other and terminate at the first pulley 2204a, and distal ends of the third and fourth drive members 1808c,d may be coupled to each other and terminate at the second pulley 2204b. In at least one embodiment, the distal ends of the first and second drive members 1808a,b and the distal ends of the third and fourth drive members 1808c,d may each be coupled together at a corresponding ball crimp 2206 (only one shown) mounted to the first or second pulley 2204a,b, respectively. As discussed above, the drive members 1808a-d may be configured to operate "antagonistically" to open or close the jaws 1610, 1612 and/or cause the end effector 1604 to articulate at the wrist 1606 in pitch or yaw directions.

The electrical conductor 1812 may also extend longitudinally within the lumen 1810, through the wrist 1606, and terminate at the electrode 1814 to supply electrical energy to the end effector 1604. The electrical conductor 1812 is depicted as exposed at the jaws 1610, 1612, but would otherwise be coupled to the electrode 1814 for proper operation. Moreover, the end effector 1604 further includes the knife 1816 (partially occluded), which is aligned with and configured to traverse the guide track 1616 as moved by the drive rod 1818.

Figure 23:
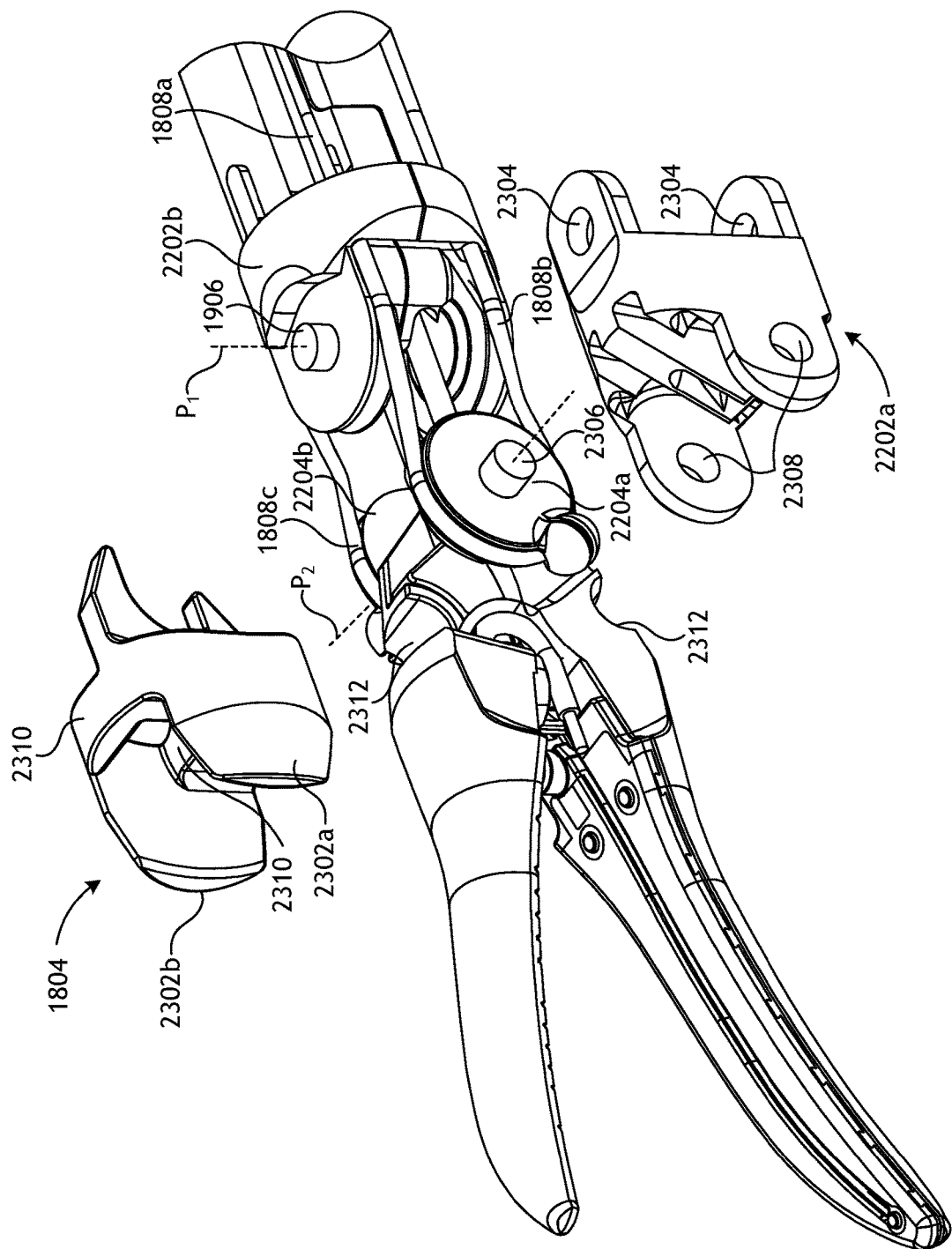
FIG. 23 is an isometric, partially exploded view of the end effector of FIG. 22, as taken from a right vantage point.

FIG. 23 is an isometric, partially exploded view of the end effector 1604 of FIG. 22, as taken from a right vantage point. In FIG. 23, the distal clevis 2202a and the linkage 1804 are shown exploded vertically from the remaining portions of the end effector 1604 and the wrist 1606, thus exposing the internal parts of the wrist 1606. In some embodiments, one or both of the distal clevis 2202a and the linkage 1804 may comprise two or more component parts that are joined to secure the wrist 1606 and rotatably secure the jaws 1610, 1612 to the wrist 1606. In the illustrated embodiment, for example, the linkage 1804 comprises opposing first and second linkage portions 2302a,b, that may be joined by welding, soldering, brazing, an adhesive, an interference fit, or by using one or more mechanical fasteners, such as pins, rivets, bolts, or any combination of the foregoing. The distal clevis 2202a, however, is depicted as a monolithic, one-piece structure, but could alternatively be made of two or more component parts, without departing from the scope of the disclosure.

In the illustrated embodiment, the proximal end of the distal clevis 2202a may be rotatably mounted to the proximal clevis 2202b by mating apertures 2304 defined on the distal clevis 2202a with the pins 1906 (one shown) defined on the proximal clevis 2202b. Mating the aperture(s) 2304 with the pin(s) 1906 may allow the wrist 1606 to articulate in "yaw" about the first pivot axis $P_1$. In alternative embodiments, however, the pin(s) 1906 may be provided by the distal clevis 2202a, and the aperture(s) 2304 may be provided by the proximal clevis 2202b. Moreover, in some embodiments, the aperture(s) 2304 need not be through-holes, as depicted, but could alternatively comprise recesses defined in the distal clevis 2202a (or the proximal clevis 2202b) and sized and otherwise configured to receive the pin(s) 1906.

In the illustrated embodiment, the pulleys 2204a,b may be rotatably mounted to the distal end of the distal clevis 2202a at the second pivot axis $P_2$ of the wrist 1602. In some embodiments, for example, each pulley 2204a,b may provide or otherwise define a pin 2306 (only one shown) and the distal clevis 2202a may define opposing apertures 2308 sized to receive or mate with the corresponding pin 2306. In alternative embodiments, however, the pins 2306 may be provided by the distal clevis 2202a, and the apertures 2308 may be provided by the pulleys 2204a,b. Moreover, in some embodiments, the apertures 2308 need not be through-holes, as depicted, but could alternatively comprise recesses defined in the distal clevis 2202a (or the pulleys 2204a,b) and sized and otherwise configured to receive the pins 2306.

In the illustrated embodiment, the linkage 1804 may provide or define one or more lateral arms 2310, and the jaws 1610, 1612 may define a corresponding one or more grooves 2312 configured to receive the lateral arms 2310 and provide corresponding jaw pivot surfaces for the jaws 1610, 1612. In the illustrated embodiment, one lateral arm 2310 is received within a groove 2312 defined by the first jaw 1610, and the other lateral arm 2310 is received within a groove 2312 defined by the second jaw 1612. As the jaws 1610, 1612 move between the open and closed positions, the lateral arms 2310 interact with the corresponding grooves 2312 and thereby provide a jaw pivot point that helps prevent the jaws 1610, 1612 from separating from each other. In some embodiments, the lateral arms 2310 slidably engage the grooves 2312 as the jaws 1610, 1612 open and close, thus the grooves 2312 may operate as corresponding cam surfaces.

Figure 24A:
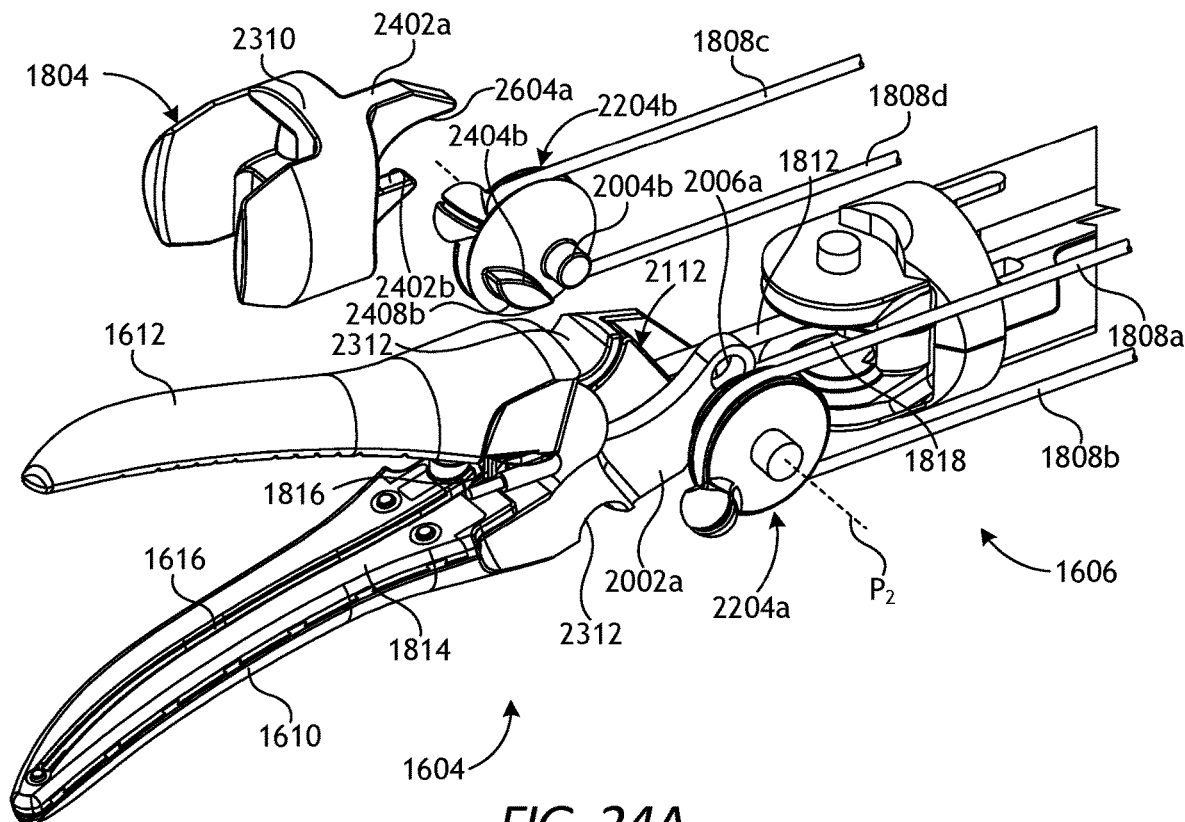
FIGS. 24A and 24B are additional isometric, partially exploded views of the end effector of FIG. 22 from right and left vantage points.
Figure 24B:
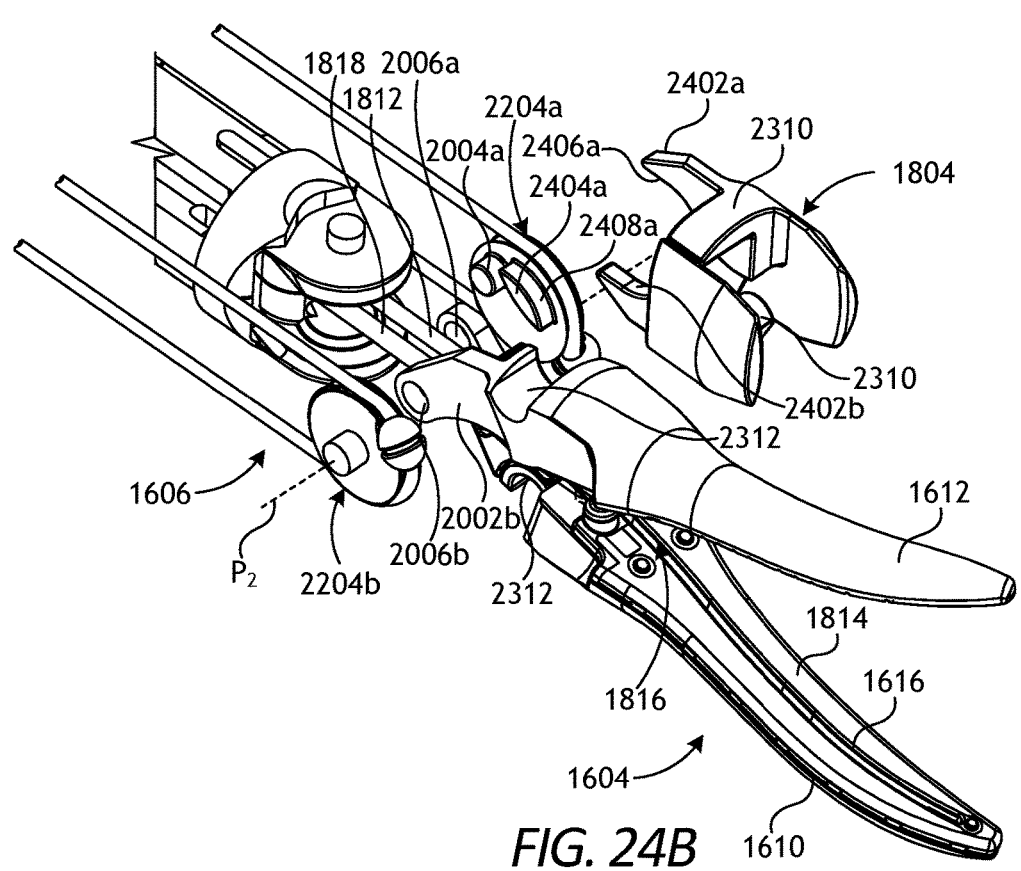

FIGS. 24A and 24B are additional isometric, partially exploded views of the end effector 1604 of FIG. 22 from right and left vantage points. In FIGS. 24A-24B, the distal clevis 2202a (FIG. 23) is removed (omitted) for simplicity, and the first and second pulleys 2204a,b and the drive members 1808a-d are shown exploded laterally from the remaining portions of the end effector 1604 and the wrist 1606.

The first jaw 1610 provides the first jaw extension 2002a (FIG. 24A) defining the first jaw aperture 2006a, and the second jaw 1612 provides the second jaw extension 2002b (FIG. 24B) defining the second jaw aperture 2006b (FIG. 24B). The first jaw extension 2002a may be rotatably coupled (e.g., pinned) to the first pulley 2204a at the first jaw pin 2004a (FIG. 24B) such that movement (rotation) of the first pulley 2204a correspondingly moves the first jaw 1610, and the second jaw extension 2002b may be rotatably coupled (e.g. pinned) to the second pulley 2204b at the second jaw pin 2004b (FIG. 24A) such that movement (rotation) of the second pulley 2204b correspondingly moves the second jaw 1612. The first and second jaw pins 2004a,b are eccentric to the second pivot axis $P_2$, and thus mating the first and second jaw pins 2004a,b with the first and second jaw apertures 2006a,b, respectively, allows rotation of the pulleys 2204a,b about the second pivot axis $P_2$ to move the jaws 1610, 1612 and thereby pivot the jaws 1610, 1612 about the jaw pivot between the open and closed positions as constrained by the lateral arms 2310.

Selective actuation and antagonistic operation of the drive members 1808a-d can open or close the jaws 1610, 1612. Because the jaws 1610, 1612 are pinned to the pulleys 2204a,b and pivotally constrained by the lateral arms 2310 at the grooves 2312, as generally described above, selectively actuating the drive members 1808a-d such that the pulleys 2204a,b rotate in opposite angular directions may result in the jaws 1610, 1612 opening or closing. Selective actuation and antagonistic operation of the drive members 1808a-d may also cause the end effector 1604 to articulate at the wrist 1606 in both pitch and yaw directions. More particularly, selectively actuating the drive members 1808a-d such that the pulleys 2204a,b rotate in the same angular direction may result in the jaws 1610, 1612 pivoting about the second pivot axis $P_2$ and thereby moving the end effector 1604 up or down in pitch. Moreover, selective actuation of a first connected pair of drive members 1808a-d while relaxing a second pair of connected drive members 1808a-d may cause the end effector 1604 to pivot about the first pivot axis $P_1$ and thereby move in yaw.

The wrist 1606 may further provide a jaw constraint that helps prevent the jaws 1610, 1612 from rotating out of alignment with each other as the jaws 1610, 1612 open and close. More specifically, because the jaws 1610, 1612 are pinned to the pulleys 2204a,b, as generally described above, rotating the pulleys 2204a,b about the second pivot axis $P_2$ will cause the jaws 1610, 1612 to move (translate) distally or proximally, depending on the rotational direction of the pulleys 2204a,b. The jaw constraint helps prevent the jaws 1610, 1612 from rotating about the jaw pins 2004a,b as the jaws axially translate.

In the illustrated embodiment, the jaw constraint includes first and second alignment arms 2402a,b provided by or defined on the linkage 1804. The alignment arms 2402a,b extend proximally from the linkage 1804 and are engageable with first and second cams 2404a,b, respectively, provided on the pulleys 2204a,b. More specifically, an inner arcuate surface 2406a of the first alignment arm 2402a may be arranged in the wrist 1606 to slidably engage an outer arcuate surface 2408a of the first cam 2404a, and an inner arcuate surface 2406b of the second alignment arm 2402b may be arranged in the wrist 1606 to slidably engage an outer arcuate surface 2408b of the second cam 2404b. During example operation, as the pulleys 2204a,b rotate to open or close the jaws 1610, 1612, the outer arcuate surfaces 2408a,b of the cams 2404a,b will slide against the opposing inner arcuate surfaces 2406a,b of the alignment arms 2402a, b, respectively. During this motion, any rotational torque that may be imparted to the jaws 1610, 1612 by rotation about the jaw pins 2004a,b will be assumed by the linkage 1804 at the alignment arms 2402, and thus helping to prevent the jaws 1610, 1612 from rotating about the jaw pins 2004a,b as the jaws axially translate and open or close.

The jaw constraint may also prove advantageous in allowing the wrist 1606 to be generally open through its central portions (e.g., middle). As a result, the wrist 1606 may be capable of accommodating the knife 1816 (mostly occluded) and the drive rod 1818 through the middle of the wrist 1606 such that the knife 1816 can be received within the guide track 1616 upon firing the end effector 1604. The open central portions of the wrist 1606 may also be able to accommodate the electrical conductor 1812, which terminates at the electrode 1814. In at least one embodiment, the distal wedge 2112 (FIG. 24A) may be positioned in the central portion or middle of the wrist 1606 and may receive and help guide one or both of the knife 1816 and the electrical conductor 1812 to the jaws 1610, 1612.

Tool with Bifurcation Wire Routing

Figure 25:
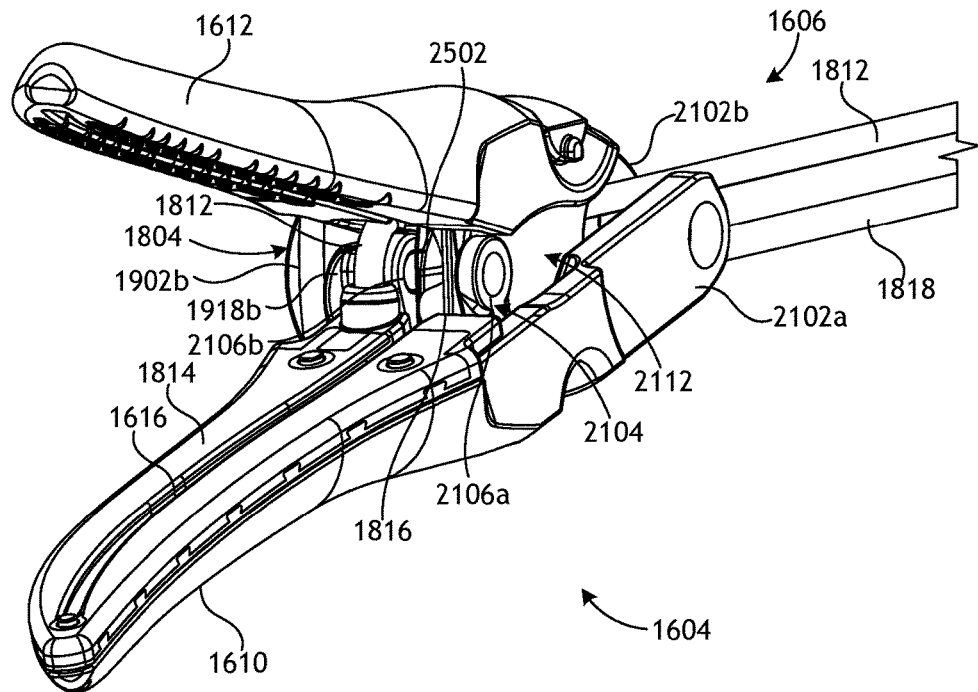
FIG. 25 is a perspective end view of the end effector of FIG. 18, according to one or more embodiments.

FIG. 25 is a perspective end view of the end effector 1604 of FIG. 18. More specifically, FIG. 25 shows the opposing jaws 1610, 1612 and portions of the wrist 1606, including the second linkage portion 1902b of the linkage 1804, the second alignment arm 1918b, and the alignment link 2104 rotatably coupled to the second alignment arm 1918b, as generally described above. Various remaining portions of the wrist 1606 are omitted for simplicity and for discussion purposes.

FIG. 25 also depicts the distal wedge 2112 arranged within a central portion or middle of the wrist 1606 and distal to the distal articulation joint 1802a (FIGS. 19A-19B), according to one or more embodiments. As illustrated, the distal wedge 2112 is generally arranged within the linkage 1804 and positioned between the first and second jaw extensions 2102a,b of the jaws 1610, 1612. The distal wedge 2112 may also extend at least partially through the alignment link 2104 between the first and second link extensions 2106a,b, as discussed above. In some embodiments, the lateral sides of the distal wedge 2112 may slidingly engage opposing inner surfaces of some or all of the alignment arms 1918a,b, the jaw extensions 2102a,b, and the link extensions 2106a,b.

In some embodiments, the distal wedge 2112 is not coupled (fixed) to any portion of the end effector 1604 or the wrist 1606 and, therefore, may be detached from any portion thereof. Instead, in such embodiments, the distal wedge 2112 is secured between portions of the linkage 1804, the alignment arms 1918a,b, the jaw extensions 2102a,b, and the link extensions 2106a,b as the wrist 1606 is assembled.

In some embodiments, the distal wedge 2112 may receive and help guide the knife 1816 to the jaws 1610, 1612. In the illustrated embodiment, the distal wedge 2112 defines a knife cavity or housing 2502 through which the knife 1816 and the drive rod 1818 are able to extend to move the knife 1816 into and along the guide track 1616. More specifically, upon firing the end effector 1604, the drive rod 1818 is moved (urged) distally, which correspondingly moves the knife 1816 out of the knife housing 2502 and into the guide track 1616. After firing is complete, the drive rod 1818 is retracted proximally, which pulls the knife 1816 proximally and back into the knife housing 2502 until it is desired to fire the end effector 1604 again. In at least one embodiment, the knife housing 2502 may be provided or otherwise defined by one or both of the jaws 1610, 1612, or alternatively an electrode component (not shown), made of a non-conductive plastic, may provide the knife housing 2502, without departing from the scope of the disclosure.

In some embodiments, as illustrated, the distal wedge 2112 may also receive and help guide the electrical conductor 1812 to the jaws 1610, 1612 and, more particularly, to the electrode 1814 to provide an electrical current generated by at least one electrosurgical generator in electrical communication with the handle 1614 (FIGS. 16 and 17). The electrical conductor 1812 may pass through, around, above, below, or on one or both sides of the distal wedge 2112, or any combination thereof.

The distal wedge 2112 may also be configured to protect the electrical conductor 1812 from damage and manage slack in the electrical conductor 1812 while the end effector 1604 and the wrist 1606 to operate. More specifically, the distal wedge 2112 may be designed to guide the electrical conductor 1812 to ensure that it is isolated from moving parts and/or mechanisms of the end effector 1604 or the wrist 1606, which may inadvertently abrade or damage the electrical conductor 1812 and thereby potentially result in arcing or shorting. Example moving parts and/or mechanisms of the end effector 1604 or the wrist 1606 include the knife rod 1818, the devises 1802a,b, the articulation arms 1918a,b, and the articulation link 2104, all of which could inadvertently contact and damage the electrical conductor 1812 during operation if not properly protected by the distal wedge 2112.

Figure 26A:
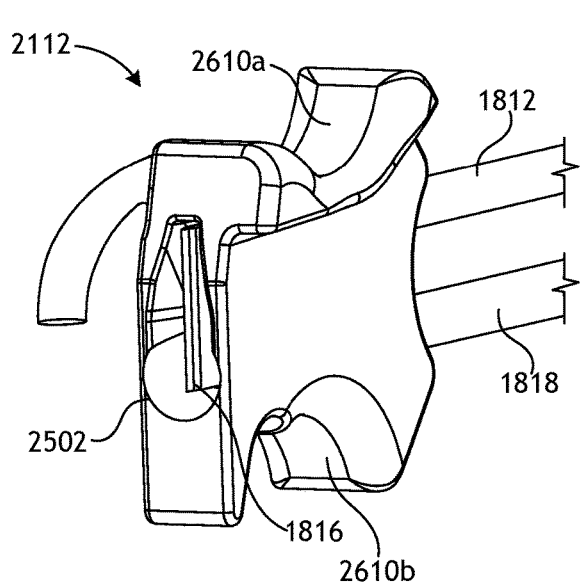
FIGS. 26A and 26B are right and left isometric views, respectively, of the distal wedge of FIG. 25, according to one or more embodiments.
Figure 26B:
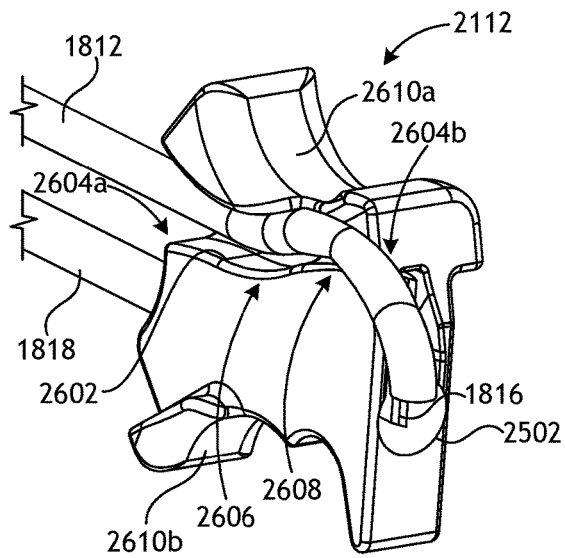

FIGS. 26A and 26B are right and left isometric views, respectively, of the distal wedge 2112 of FIG. 25, according to one or more embodiments. The distal wedge 2112 may be made of a variety of rigid materials including, but not limited to, a metal, a cast metal alloy, a wrought metal, a polymer composite, a ceramic, a negative-index metamaterial (NIM), a metal injection molding (MIM), a reinforced plastic or thermoplastic, (e.g., nylon, polyetherimide or Ultem®, polyether ether ketone or PEEK, etc.), or any combination thereof. In some embodiments, the reinforced plastics or thermoplastics may be carbon or glass filled.

As described above, the distal wedge 2112 defines the knife housing 2502 that receives and guides the knife 1816 as driven by the drive rod 1818. Moreover, the distal wedge 2112 may further provide or otherwise define one or more channels 2602 (one visible in FIG. 26B) configured to receive and guide the electrical conductor 1812 toward the electrode 1814 (FIG. 25). As best seen in FIG. 26B, the channel 2602 may extend from a first or "proximal" end 2604a of the distal wedge 2112 to a second or "distal" end 2604b of the distal wedge 2112, but could alternatively begin or terminate at any point between the ends 2602a,b, without departing from the scope of the disclosure.

In some embodiments, the channel 2602 may define or otherwise provide one or more vertical and/or horizontal curves, undulations, or direction changes that alter the course or pathway of the channel 2602 and thereby change the course of the electrical conductor 1812 received within the channel 2602. In the illustrated embodiment, for example, the channel 2602 includes at least one vertical direction change 2606 where the route of the channel 2602 moves vertically, and at least one horizontal direction change 2608 where the route of the channel 2602 moves laterally or horizontally. In other embodiments, however, more than one vertical and lateral direction change 2606, 2608 may be included in the channel 2602, without departing from the scope of the disclosure.

In at least one embodiment, the opening to the channel 2602 at the first end 2604a may be enlarged and otherwise flared outward. This may prove advantageous in providing strain relief for the electrical conductor 1812 while the end effector 1604 (FIG. 25) articulates in pitch, and as the bifurcating jaws 1610, 1612 (FIG. 25) open and close. Accordingly, the distal wedge 2112 can help relieve potential strain in the electrical conductor 1812, which may help avoid premature fatigue. The enlarged opening at the first end 1604a may also prove advantageous in helping to manage slack in the electrical conductor 1812 as the end effector 1604 articulates. For example, the electrical conductor 1812 may be loosely received within the channel 2602, which allows the electrical conductor 1812 to move back and forth within the channel 2602 during operation to manage slack. The channel 2602 further acts to establish the minimum bend radius of the electrical conductor 1812 by preventing too sharp a bend, often referred to as a kink, as the electrical conductor 1812 traverses the channel 2602 to reach the electrode 1814 (FIG. 25). Limiting the minimum bend radius is critical in preventing fatigue failure of conductor strands housed inside the insulative jacket of the electrical conductor 1812.

In some embodiments, as illustrated, the distal wedge 2112 may provide or otherwise define one or more arcuate surfaces, shown as a first or "upper" arcuate (concave) surface 2610a and a second or "lower" arcuate (concave) surface 2610b. The arcuate surfaces 2610a,b may receive and engage corresponding curved (convex) portions of the jaws 1610, 1612 (FIG. 25). In operation, the arcuate surfaces 2610a,b may operate as cam surfaces as the jaws 1610, 1612 open and close. In particular, the arcuate surfaces 2610a,b may prove advantageous in touch and spread dissection operations, where a user opens the jaws 1610, 1612 to move tissue. In such operations, a load is applied on the top or bottom of the jaw jaws 1610, 1612 and this load is transferred to the distal wedge 2112 at the arcuate surfaces 2610a,b. Accordingly, the arcuate surfaces 2610a,b may support the jaws 1610, 1612 and bear loading required to move the tissue.

Figure 27:
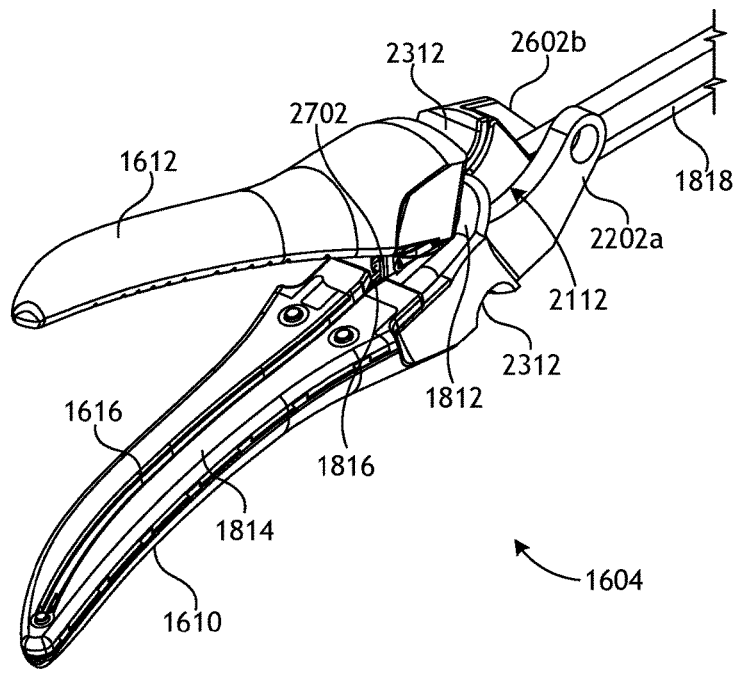
FIG. 27 is a perspective end view of the end effector of FIG. 22, according to one or more embodiments.

FIG. 27 is a perspective end view of the end effector 1604 of FIG. 22. More specifically, FIG. 27 shows the opposing jaws 1610, 1612 in the open position and an alternative example of the distal wedge 2112, according to one or more additional embodiments. Remaining portions of the wrist 1606 (FIG. 22) and the end effector 1604 are omitted for simplicity and for discussion purposes.

The distal wedge 2112 of FIG. 27 is similar in some respects to the distal wedge 2112 of FIG. 25. For instance, the distal wedge 2112 is able to be arranged within the central portions or middle of the wrist 1606 (FIG. 22) and distal to the distal articulation joint 1802a (FIGS. 19A-19B). Moreover, the distal wedge 2112 may be generally situated within the linkage 1804 (FIG. 22), which is mounted to the jaws 1610, 1612 at the grooves 2312, as generally described above. As illustrated, the distal wedge 2112 is positioned between the first and second jaw extensions 2102a,b of the jaws 1610, 1612 and, in some embodiments, the lateral sides of the distal wedge 2112 may slidingly engage opposing inner surfaces of the jaw extensions 2102a,b. The distal wedge 2112 may not be coupled (fixed) to any portion of the end effector 1604 or the wrist 1606 and, therefore, may be detached from any portion thereof. Instead, in such embodiments, the distal wedge 2112 is secured between portions of the linkage 1804 and the jaw extensions 2102a,b as the wrist 1606 is assembled.

In some embodiments, the distal wedge 2112 may receive and help guide the knife 1816 to the jaws 1610, 1612. In the illustrated embodiment, the distal wedge 2112 defines a knife housing 2702 through which the knife 1816 and the drive rod 1818 are able to extend to move the knife 1816 into and along the guide track 1616 upon firing the end effector 1604. After firing is complete, the drive rod 1818 is retracted proximally, which pulls the knife 1816 proximally and back into the knife housing 2702 until it is desired to fire the end effector 1604 again.

The distal wedge 2112 may also receive and help guide the electrical conductor 1812 to the jaws 1610, 1612 and, more particularly, to the electrode 1814 to provide an electrical current to the end effector 1604. Similar to the distal wedge 2112 of FIG. 25, the distal wedge of FIG. 27 may guide the electrical conductor 1812 through, around, above, below, or on one or both sides of the distal wedge 2112, or any combination thereof. Moreover, the distal wedge 2112 may also protect the electrical conductor 1812 from damage by guiding the electrical conductor 1812 such that it is isolated from moving parts and/or mechanisms of the end effector 1604 or the wrist 1606, which may inadvertently abrade or damage the electrical conductor 1812 and thereby potentially result in arcing or shorting. The distal wedge 2112 may also help manage slack in the electrical conductor 1812 while the end effector 1604 and the wrist 1606 to operate, as discussed below.

Figure 28A:
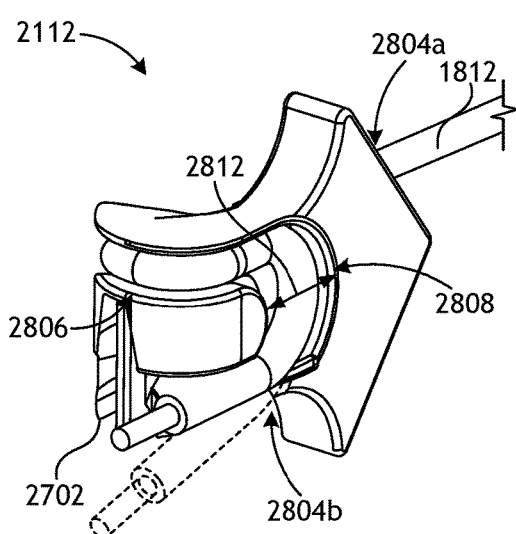
FIGS. 28A and 28B are right and left isometric views, respectively, of the distal wedge of FIG. 27, according to one or more embodiments.
Figure 28B:
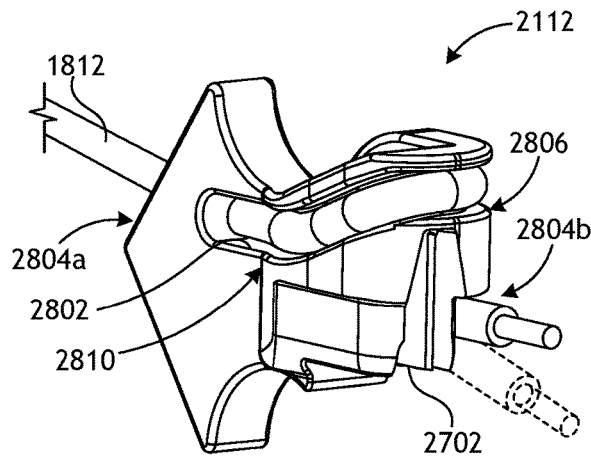

FIGS. 28A and 28B are right and left isometric views, respectively, of the distal wedge 2112 of FIG. 27, according to one or more embodiments. As described above, the distal wedge 2112 defines the knife housing 2702 that receives and guides the knife 1816 (FIG. 27) as driven by the drive rod 1818 (FIG. 27). Moreover, similar to the distal wedge 2112 of FIGS. 26A-26B, the distal wedge 2112 of FIGS. 28A-28B may provide the arcuate surfaces 2610a,b configured to receive and engage corresponding curved portions of the jaws 1610, 1612 (FIG. 27).

The distal wedge 2112 may further provide or otherwise define one or more channels 2802 configured to receive and guide the electrical conductor 1812 toward the electrode 1814 (FIG. 27). In some embodiments, the channel 2802 may extend from a first or "proximal" end 2804a of the distal wedge 2112 to a second or "distal" end 2804b of the distal wedge 2112, but could alternatively begin or terminate at any point between the ends 2802a,b, without departing from the scope of the disclosure. In the illustrated embodiment, the electrical conductor 1812 is received within the channel 2802 at the proximal end 2804a, routed through the channel 2802 until exiting at the distal end 2804b.

In some embodiments, the channel 2802 may define or otherwise provide one or more vertical and/or horizontal curves, undulations, or direction changes that alter the course or pathway of the channel 2802 and thereby changes the course and direction of the electrical conductor 1812 as it follows the channel 2802. In the illustrated embodiment, for example, the channel 2802 includes a horizontal direction change 2806, where the course of the channel 2802 assumes an in-plane angular turn (e.g., 180°) in a generally horizontal plane and back toward the proximal end 2804a, and a vertical direction change 2808 (FIG. 28A), where the course of the channel assumes another in-plane angular turn (e.g., 180°) in a generally vertical plane and back toward the distal end 2804b. As best seen in FIG. 28B, the channel 2802 may also include a second vertical direction change 2810 leading into the horizontal direction change 2806. Accordingly, the channel 2802 may be defined in the distal wedge 2112 to allow the electrical conductor 1812 to partially wrap around a portion of the distal wedge 2112.

The electrical conductor 1812 is depicted in FIGS. 28A-28B as exiting the channel 2802 straight (solid lines) and at a downward angle (dashed lines). This is representative of pitch movement and opening and closing of the bifurcating jaws 1610, 1612 (FIG. 27) that might occur during operation of the end effector 1604 (FIG. 27) and which the electrical conductor 1812 will simultaneously have to assume. To help relieve potential strain in the electrical conductor 1812 and avoid premature fatigue during operation, the opening to the channel 2802 at the distal end 2804b may be enlarged and otherwise flared outward to allow the electrical conductor 1812 to move within the channel 2802 along with movement of the jaws 1610, 1612 and without binding the electrical conductor 1812 against adjacent structures.

The distal wedge 2112 may also help with slack management of the electrical conductor 1812 during operation. The enlarged opening at the distal end 1804b may help somewhat in this regard, but the channel 2802 may also provide a gap 2812 (FIG. 28A) for the electrical conductor 1812 to move back and forth (reciprocate) within during operation. In the illustrated embodiment, the gap 2812 is provided in the vertical direction change 2808, but could alternatively be provided in other locations of the channel 2802, without departing from the scope of the disclosure. Since the electrical conductor 1812 is loosely received within the channel 2802, the gap 2812 allows the electrical conductor 1812 to move back and forth during operation to manage slack. The channel 2802 further acts to establish the minimum bend radius of the electrical conductor 1812 by preventing too sharp a bend, often referred to as a kink, as the electrical conductor 1812 traverses the channel 2802 to reach the electrode 1814 (FIG. 27). Limiting the minimum bend radius is critical in preventing fatigue failure of conductor strands housed inside the insulative jacket of the electrical conductor 1812.

Hybrid Concept to Drive End Effector Closure and Pitch

Figure 29:
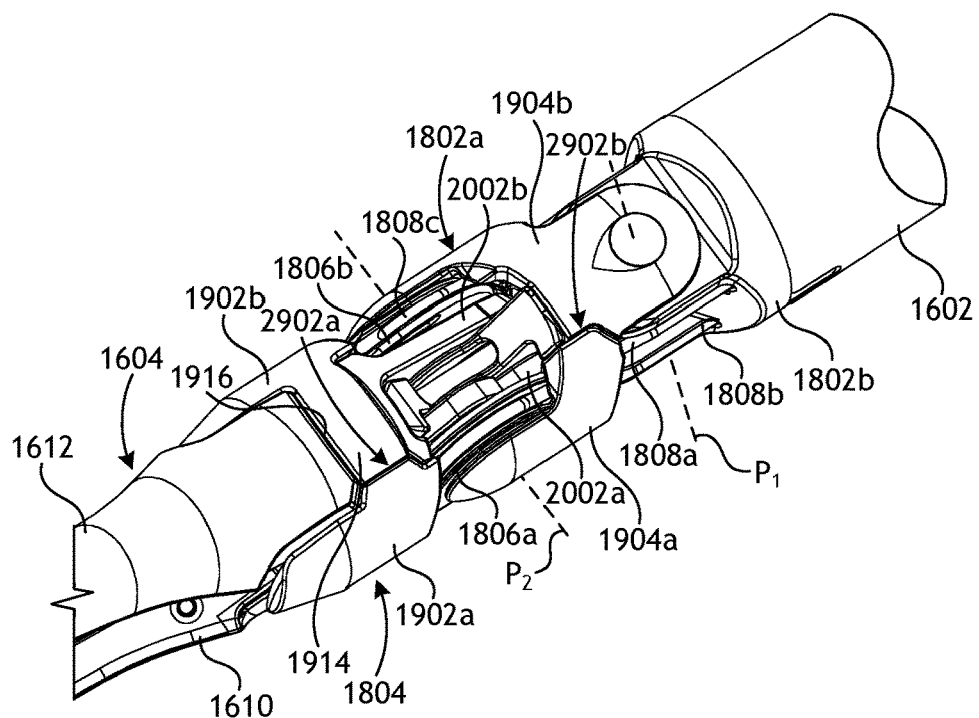
FIG. 29 is an isometric top view of the end effector and the wrist of FIG. 18, according to one or more embodiments.

FIG. 29 is an isometric top view of the end effector 1604 and the wrist 1606 of FIG. 18, according to one or more embodiments. As discussed above, the wrist 1606 interposes the shaft 1602 and the end effector 1604 and helps facilitate articulation of the end effector 1604 relative to the shaft 1602. The wrist 1606 can include the linkage 1804, the distal articulation joint 1802a, and the proximal articulation joint 1802b, where the proximal articulation joint 1802b may form an integral part or extension of the shaft 1602 (or a shaft adapter), or may alternatively comprise a separate or discrete portion of the wrist 1602 coupled to the shaft 1602 (or a shaft adapter).

The proximal end of the distal articulation joint 1802a may be rotatably coupled to the shaft 106 (e.g., at the proximal articulation joint 1802b) at the first pivot axis $P_1$, and the first and second pulleys 1806a and 1806b may be rotatably mounted to the distal end of the distal articulation joint 1802a at the second pivot axis $P_2$. Moreover, the linkage 1804 may be arranged distal to the second pivot axis $P_2$ and operatively mounted to the jaws 1610, 1612, as generally described above. Movement of the end effector 1604 about the first pivot axis $P_1$ provides "yaw" articulation of the end effector 1604, and movement about the second pivot axis $P_2$ provides "pitch" articulation of the end effector 1604.

Furthermore, the first and second jaw extensions 2002a,b extend from the first and second jaws 1610, 1612 and may be rotatably coupled (e.g., pinned) to the first and second pulleys 1806a,b, respectively, as also discussed above. Consequently, movement (rotation) of the pulleys 1806a,b may cause the jaws 1610, 1612 to pivot about the jaw pivot point where the lateral arms 1914 (one visible) of the linkage 1804 are received within corresponding grooves 1916 (one visible) defined by the jaws 1610, 1612.

As discussed above, in some embodiments, one or both of the distal articulation joint 1802a or the linkage 1804 may comprise two or more component parts that are joined to help form and secure the wrist 1606. The linkage 1804 can include, for example, the opposing first and second linkage portions 1902a,b, and the distal articulation joint 1802a can include the opposing first and second distal articulation joint portions 1904a,b. The linkage portions 1902a,b may be joined at one or more linkage interfaces 2902a (one visible), and the distal articulation joint portions 1904a,b may be joined at one or more distal joint interfaces 2902b (one visible). Joining the linkage and articulation joint portions 1902a,b, 1904a,b at their respective joint interfaces 2902a,b may be accomplished by welding, soldering, brazing, an adhesive, an interference fit, or by using one or more mechanical fasteners, such as pins, rivets, bolts, or any combination of the foregoing.

Joining the linkage and articulation joint portions 1902a, b, 1904a,b helps build and secure the wrist 1606 for operation. Joining the linkage portions 1902a,b, for example, may rotatably secure the jaws 1610, 1612 to the wrist 1606, and joining the distal articulation joint portions 1904a,b may help secure the pulleys 1806a,b and other component parts within the wrist 1606. In the illustrated embodiment, the pulleys 1806a,b interpose portions of the jaws 1610, 1612 and the distal articulation joint 1802a. More specifically, the first pulley 1806a may interpose the first jaw extension 2002a and the first distal articulation portion 1904a, and the second pulley 1806b may interpose the second jaw extension 2002b and the second distal articulation portion 1904b. Consequently, the first pulley 1806a may engage an outer side (lateral) surface of the first jaw extension 2002a and/or an inner side surface of the first distal articulation portion 1904a, and the second pulley 1806b may engage an outer side (lateral) surface of the second jaw extension 2002b and/or an inner side surface of the second distal articulation portion 1904b. Joining the distal articulation joint portions 1904a,b at the distal joint interfaces 2902b may help secure the pulleys 1806a,b between the jaw extensions 2002a,b and opposing distal articulation portions 1904a,b, respectively, and thereby orient the pulleys 1806a,b in a parallel, planar orientation for consistent operation of the end effector 1604 and the wrist 1606.

The drive members 1808a-d (the fourth drive member 1808d occluded in FIG. 29) extend longitudinally through the proximal articulation joint 1802b and the distal articulation joint 1802a and terminate at the pulleys 1806a,b. As discussed herein, the distal ends of the first and second drive members 1808a,b may be coupled to each other and terminate at the first pulley 1806a, and the distal ends of the third and fourth drive members 1808c,d may be coupled to each other and terminate at the second pulley 1806b. As generally described above, antagonistic operation of the drive members 1808a-d may cause the jaws 1610, 1612 to open or close, or may alternatively cause the end effector 1604 to articulate at the wrist 1606 about one or both of the pivot axes $P_1$, $P_2$. More specifically, selectively actuating the drive members 1808a-d such that the pulleys 1806a,b rotate in opposite angular directions may result in the jaws 1610, 1612 opening or closing. Moreover, selectively actuating the drive members 1808a-d such that the pulleys 1806a,b rotate in the same angular direction may result in the jaws 1610, 1612 pivoting about the second pivot axis $P_2$ and thereby moving the end effector 1604 up or down in pitch. Furthermore, selective actuation of a first connected pair of drive members 1808a-d while relaxing a second pair of connected drive members 1808a-d may cause the end effector 1604 to pivot about the first pivot axis $P_1$ and thereby move in yaw.

Figure 30:
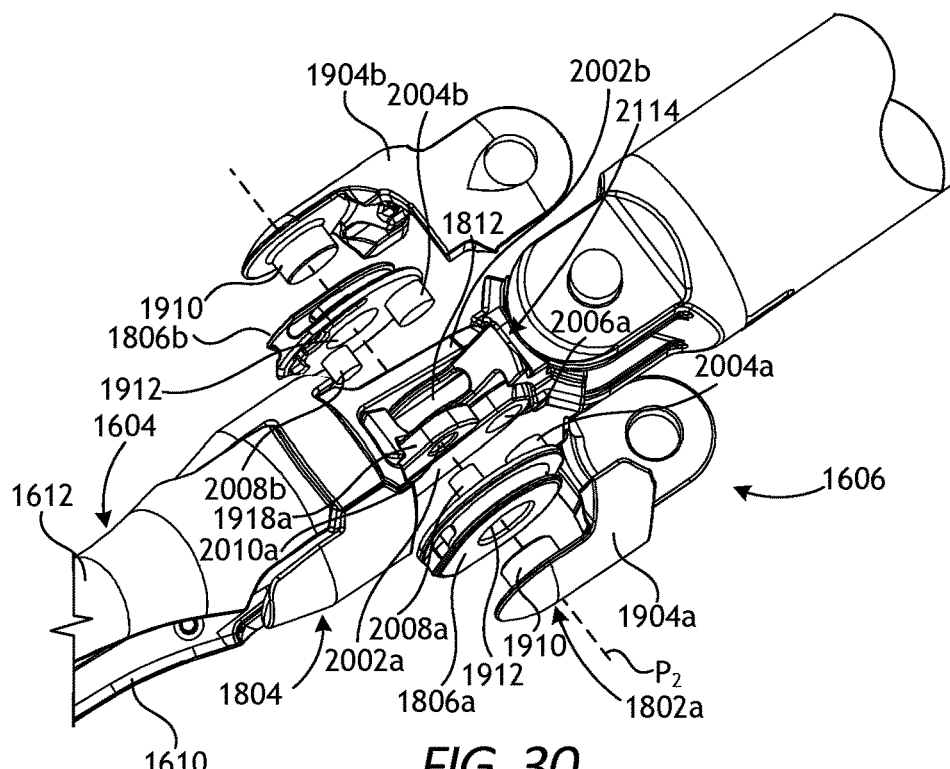
FIG. 30 is an isometric top view of the end effector and wrist of FIG. 29, with the wrist partially exploded, according to one or more embodiments.

FIG. 30 is an isometric top view of the end effector 1604 and the wrist 1606 of FIG. 29, with the wrist 1606 partially exploded, according to one or more embodiments. More specifically, the distal articulation joint 1802a and the pulleys 1806a,b are shown in FIG. 30 exploded laterally outward, and the drive members 1801a-d (FIG. 29) are omitted for simplicity.

The pulleys 1806a,b may be rotatably mounted to the distal articulation joint 1802a such that a rotational axis is established that extends through the second pivot axis $P_2$. More specifically, the distal articulation joint 1802a may define the opposing pins 1910 receivable within or otherwise matable with the apertures 1912 defined in the pulleys 1806a,b. The pins 1910 and the apertures 1912 may be coaxially aligned with the second pivot axis $P_2$, thereby fixing the rotational axis of the pulleys 1806a,b along the second pivot axis $P_2$. The pins 1910 support the pulleys 1806a,b in the wrist 1606 such that the pulleys 1806a,b need not be fixed or supported by any other portion of the wrist 1606. Rather, as mentioned above, the pulleys 1806a,b interpose the jaw extensions 2002a,b and the distal articulation joint 1802a and may be engageable with adjacent surfaces of one or both. Once the distal articulation joint portions 1904a,b are joined, as described above, the pulleys 1806a,b will be secured within the wrist 1606 and unable to be removed without disassembling (breaching) the wrist 1606.

The pins 1910 may alternatively comprise bosses or cam features, without departing from the scope of the disclosure. Moreover, in alternative embodiments, the pins 1910 (or bosses or cam features) may be provided by the pulleys 1806a,b, and the apertures 1912 may instead be provided by the distal articulation joint 1802a, without departing from the scope of the disclosure. Moreover, in some embodiments, the apertures 1912 need not be through-holes, as depicted, but could alternatively comprise recesses defined in the pulleys 1806a,b (or the distal articulation joint 1802a) and sized and otherwise configured to receive (mate with) the pins 1910.

As described herein, the pulleys 1806a,b may provide or otherwise define one or more pins that are eccentric to the second pivot axis $P_2$. The first and second jaw pins 2004a,b, for example, may be defined on or otherwise provided by the pulleys 1806a,b and configured to mate with the first and second jaw apertures 2006a,b (only the first jaw aperture 1006a visible) defined on the first and second jaw extensions 2002a,b, respectively. Coupling the jaw pins 2004a,b to the jaw apertures 2006a,b allows rotation of the pulleys 1806a,b to pivot the jaws 1610, 1612 between the open and closed positions and move the end effector 1604 in pitch about the second pivot axis $P_2$. In other embodiments, the jaw pins 2004a,b may instead be provided on the jaw extensions 2002a,b, and the jaw apertures 2006a,b may be provided on the pulleys 1806a,b, or any combination thereof. Moreover, the jaw apertures 2006a,b need not be through-holes, but could alternatively comprise recesses defined in the jaw extensions 2002a,b (or the pulleys 1806a,b) and sized and otherwise configured to receive the jaw pins 2004a,b.

The pulleys 1806a,b may also be rotatably coupled (e.g., pinned) to the alignment arms 1918a,b (only the first alignment arm 1918a visible) such that movement (rotation) of the pulleys 1806a,b correspondingly moves the alignment arms 1918a,b. As illustrated, the arm pins 2008a,b defined on the pulleys 1806a,b may be matable with the arm apertures 2010a,b (only the first arm aperture 2010a visible) defined by the alignment arms 1918a,b. Similar to the jaw pins 2004a,b, the arm pins 2008a,b are eccentric to the second pivot axis $P_2$, and the arm pins 2008a,b are also angularly offset from the first and second jaw pins 2004a,b. Consequently, as the pulleys 1806a,b rotate about the second pivot axis $P_2$, the alignment arms 1918a,b are correspondingly moved and the distal ends of the alignment arms 1918a,b are urged to slide within (traverse) the slots 1920a,b (FIGS. 19A-19B) of the linkage 1804. In other embodiments, the arm pins 2008a,b may be provided on the alignment arms 1918a,b, and the arm apertures 2010a,b may be provided on the pulleys 1806a,b, or any combination thereof. Moreover, the arm apertures 2010a,b need not be through-holes, as depicted, but could alternatively comprise recesses defined in the alignment arms 1918a,b (or the pulleys 1806a,b) and sized and otherwise configured to receive the arm pins 2008a,b.

As discussed above, the mid-articulation insert 2114 may be arranged within the central portion or middle of the wrist 1606 to help guide the electrical conductor 1812 and the knife 1816 (FIG. 18) through the center of the wrist 1606.

The mid-articulation insert 2114 may be generally arranged within the distal clevis 1802a and positioned between (interposing) the opposing jaw extensions 2102a,b and the opposing alignment arms 1918a,b. Accordingly, the mid-articulation insert 2114 may help maintain proper lateral spacing of the jaw extensions 2102a,b and the alignment arms 1918a,b as pinned to the pulleys 1806a,b. Upon joining the distal articulation joint portions 1904a,b, as described above, the pulleys 1806a,b, the jaws 1610, 1612 (e.g., jaw extensions 2002a,b), the alignment arms 1918a,b, and the mid-articulation insert 2114 will all be secured within the wrist 1606 and unable to be removed without disassembling (breaching) the wrist 1606.

RF Tool with Split Clevis

Referring again to FIGS. 19A-19B, as described above, the linkage 1804 may be mounted to or otherwise encircle the jaws 1610, 1612 to help the jaws 1610, 1612 pivot between the open and closed positions. More specifically, the linkage 1804 may provide one or more lateral arms 1914, which are receivable within a corresponding one or more grooves 1916 defined on the jaws 1610, 1612. One lateral arm 1914, for example, may be received within a groove 1916 defined by the first jaw 1610, and the other lateral arm 1914 may be received within a groove 1916 defined by the second jaw 1612. As the jaws 1610, 1612 pivot between the open and closed positions, the lateral arms 1914 interact with the corresponding grooves 1916 and help prevent the jaws 1610, 1612 from separating from each other. Accordingly, receiving the lateral arms 1914 in the grooves 1916 creates a jaw pivot point or location where the jaws 1610, 1612 are able to pivot. In some embodiments, the lateral arms 1914 slidably engage the grooves 1916 as the jaws 1610, 1612 open and close at the jaw pivot, thus the grooves 1916 may operate or be characterized as cam surfaces. In other embodiments, however, the, the lateral arms 1914 may move back and forth (i.e., distally and proximally) within the grooves 1916 as the jaws 1610, 1612 open and close at the jaw pivot, or a combination of both sliding and non-sliding movement, without departing from the scope of the disclosure.

The linkage 1804 can also include the opposing first and second linkage portions 1902a,b, which are essentially mirror images of each other. The linkage portions 1902a,b may be joined when assembling the wrist 1606 to secure the jaws 1610, 1612 in a pivoting relationship. As mentioned above, the linkage portions 1902a,b may be joined by welding (e.g., laser welding), soldering, brazing, an adhesive, an interference fit, or by using one or more mechanical fasteners, such as pins, rivets, bolts, or any combination of the foregoing.

According to embodiments of the present disclosure, the process of joining the linkage portions 1902a,b may also help set a proper jaw gap between the jaws 1610, 1612 when the jaws 1610, 1612 are fully closed. Jaw gap is critical to effective operation of the end effector 1604 and, in particular, to tissue graspers and vessel sealers in creating proper tissue seals. For example, the jaws 1610, 1612 operate to bring tissue together so that it can be properly sealed (cauterized), and the jaw gap should be set such that vessels are flattened upon closing the jaws 1610, 1612, or pinched together tightly, but not too tightly that the tissue fractures. If the jaw gap exceeds predetermined manufacturing tolerances by just a few thousands of an inch, the jaws 1610, 1612 may be incapable of proper tissue apposition and sealing. In such cases, the end effector 1604 may be scrapped as unfit for its intended purpose.

Figure 31:
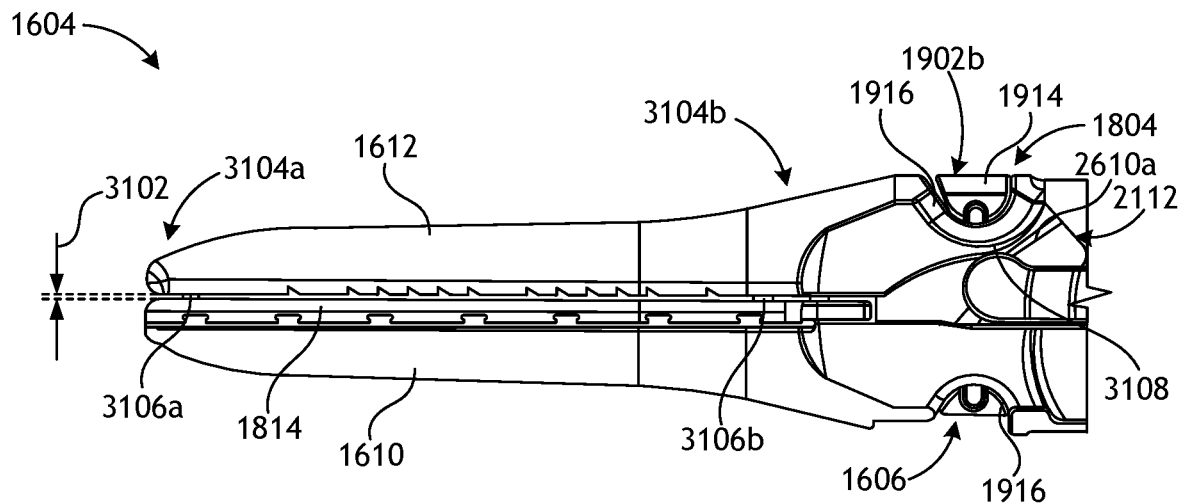
FIG. 31 is an enlarged side view of the end effector of FIG. 18, according to one or more embodiments.

FIG. 31 is an enlarged side view of the end effector 1604 of FIGS. 18 and 19A-19B, according to one or more embodiments. Only a portion of the wrist 1606 is depicted in FIG. 31, and the first linkage portion 1902a (FIGS. 19A-19B) of the linkage 1804 is omitted to enable viewing of certain parts for description purposes. As illustrated, the lateral arm 1914 of the second linkage portion 1902b is received within the groove 1916 defined by the second jaw 1612. The groove 1916 defined by the first jaw 1610 is also visible and located on the underside and would receive the lateral arm 1914 of the first linkage portion 1902a if present. The grooves 1916 provide arcuate cam surfaces that allow interaction between the lateral arms 1914 and the jaws 1610, 1612 during operation.

The jaws 1610, 1612 are depicted in FIG. 31 in the closed position and slightly offset from each other such that a jaw gap 3102 is defined between the inner (opposing) surfaces of each jaw 1610, 1612. As mentioned above, the jaw gap 3102 is critical to effective operation of the end effector 1604 in creating proper tissue seals. For instance, the magnitude of the jaw gap 3102 can be tied to a predetermined manufacturing specification, such as 0.005 inches, and if the jaw gap 3102 exceeds the predetermined value by just a few thousands of an inch (in either direction), the jaws 1610, 1612 may be incapable of properly sealing cut tissue and, thus, unfit for its intended purpose.

In some embodiments, the jaw gap 3102 may be generally uniform along the proximal-to-distal (longitudinal) length of the jaws 1610, 1612 such that the inner surfaces of each jaw 1610, 1612 are parallel to one another when closed. In other embodiments, however, the jaw gap 3102 may be non-uniform (non-parallel) to enhance sealing performance by creating different gap zones across the opposing surfaces that can accommodate different tissue types or thicknesses. Such gap zones, however, may remain within the overall specified range of the jaw gap 3102.

The jaw gap 3102 may be set during assembly of the end effector 1604 and the wrist 1606. More specifically, the jaw gap 3102 may be set by first moving the jaws 1610, 1612 to the closed position until a distal end 3104a of the jaws 1610, 1612 engages or comes into close contact with one another. In some embodiments, one or more distal spacers 3106a may be provided at or near the distal end 3104a to ensure the inner surfaces of the jaws 1610, 1612 at the distal end 3104a do not touch during operation. In the illustrated embodiment, the distal spacer(s) 3106a may extend through the electrode 1814 provided on the first jaw 1610 to engage the inner surface of the second jaw 1612. The jaws 1610, 1612 may then be progressively closed toward a proximal end 3104b, which may include one or proximal more spacers 3106b that ensure the inner surfaces of the jaws 1610, 1612 do not touch at the proximal end 3104b during operation. The spacers 3106a,b may be made of ceramic or another non-conductive material.

Sliding interaction between the lateral arms 1914 of the linkage 1804 and the grooves 1916 allows the jaw gap 3102 to be adjusted at the proximal end 3104b of the jaws 1610, 1612. More specifically, the lateral arms 1914 may be able to slide (rotate) within the corresponding grooves 1916 as the proper jaw gap 3102 magnitude is achieved between the distal and proximal ends 3104a,b. Sliding interaction between the linkage 1804 and the jaws 1610, 1612 may be advantageous in allowing necessary adjustments to the jaw gap 3102 at or near the proximal end 3104b so that the proper clamp force applied is matched with the stiffness of the jaws 1610, 1612 to deliver distal clamp force and good clamping pressure uniformly between the distal and proximal ends 3104a,b. Once the desired the jaw gap 3102 is achieved, the linkage portions 1902a,b may be joined (e.g., laser welded) at the linkage interfaces 2902a (FIGS. 29 and 32), and thereby permanently set the jaw gap 3102 for operation.

Once the linkage portions 1902a,b are joined and the jaw gap 3102 is set, if a hard contact between the jaw grooves 1916 and the lateral arms 1914 is located closer to a distal side of the grooves 1916 (i.e., surface of the groove 1916 closer to the distal end 3104a of the jaws 1610, 1612), that may provide a mechanical advantage for the jaws 1610, 1612 while closing because of the larger distance from the pulleys 1806a,b (FIGS. 18A-18B) and, more particularly, from the jaw pins 2004a.b (FIGS. 20A-20B) mated with the jaw apertures 2006a,b (FIGS. 20A-20B). In contrast, if there is hard contact between the jaw grooves 1916 and the lateral arms 1914 closer to a proximal side of the grooves 1916 (i.e., surface of the groove 1916 further from the distal end 3104a of the jaws 1610, 1612), that may provide a mechanical advantage for opening the jaws 1610, 1612, which may be advantageous in blunt dissection and touch and spread applications. Accordingly, the mechanical advantage of the jaws 1610, 1612 may be adjusted during assembly by dictating where the lateral arms 1914 will engage the corresponding grooves 1916.

Figure 32:
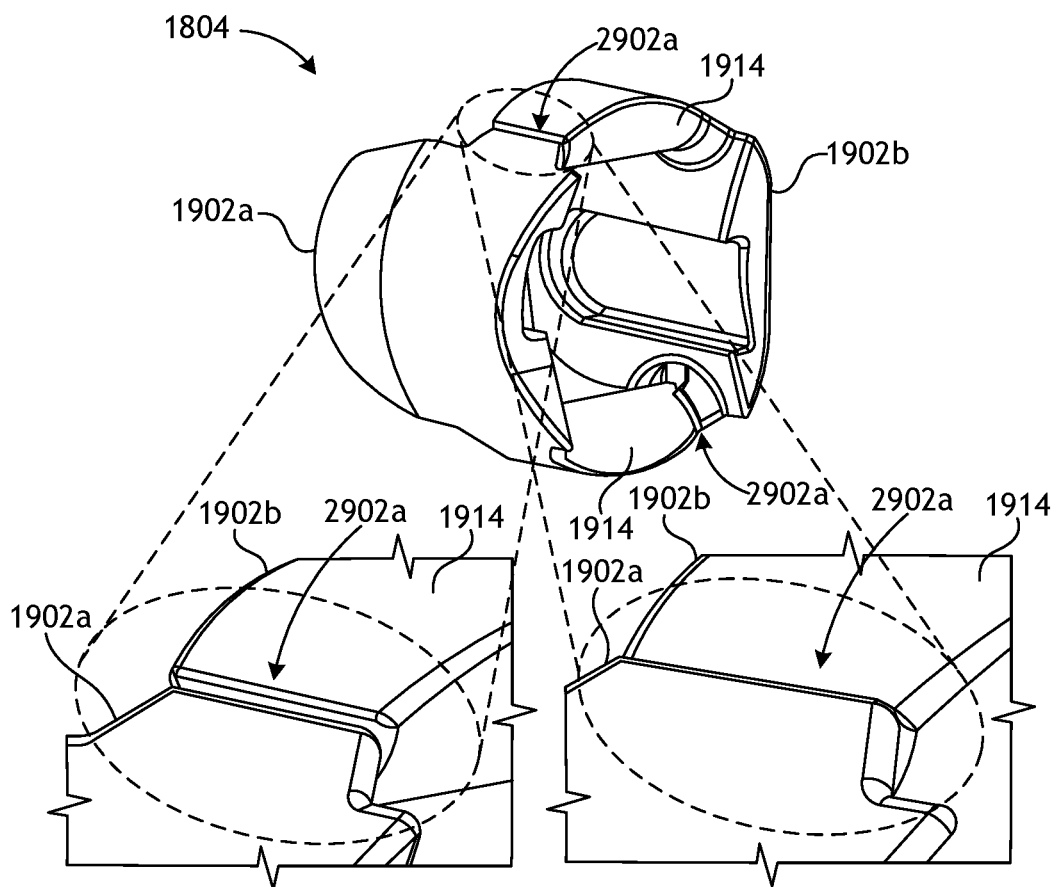
FIG. 32 is an isometric view of the distal clevis and accompanying enlarged views of the distal joint interface, according to one or more embodiments.

FIG. 32 is an isometric view of the linkage 1804 and accompanying enlarged views of the linkage interface 2902a, according to one or more embodiments. As discussed above, in some embodiments, the linkage portions 1902a,b may be joined at one or more linkage interfaces 2902a (two visible) where the lateral arm 1914 of one linkage portion 1902a,b is coupled to the opposing linkage portion 1902a,b, and thereby joining the two halves to form the linkage 1804.

As the jaw gap 3102 (FIG. 31) is adjusted to the desired magnitude, the linkage portions 1902a,b may be able to be pushed together and adjusted up and down relative to each other to help achieve the proper jaw gap 3102. The enlarged image on the left of FIG. 32 shows the lateral arm 1914 of the second linkage portion 1902b being moved up relative to the first linkage portion 1902a, and the enlarged image on the right of FIG. 32 shows the lateral arm 1914 of the second linkage portion 1902b being moved down relative to the first linkage portion 1902a. Once the proper magnitude for the jaw gap 3102 is achieved, the linkage portions 1902a,b may be joined at the linkage interfaces 2902a. This adjustability of the linkage portions 1902a,b may be advantageous in achieving precise jaw gap during manufacturing due to component tolerances. Components comprising the jaws 1610, 1612 and the distal end of the end effector 1604 (FIG. 31) will vary over time from part to part and batch to batch within the limits established on the component drawings through geometric dimensioning and tolerancing. Adjustability may prove useful in removing this source of jaw gap variation.

Referring again to FIG. 31, the design of the distal wedge 2112 may also help in the process of setting the jaw gap 2103. More particularly, receiving a curved portion 3108 (one shown) of each jaw 1610, 1612 within a corresponding one of the arcuate surfaces 2610a,b (only the first arcuate surface 2610a visible) may help set the minimal spacing between the jaws 1610, 1612. The distal wedge may be sized and have tolerances such that it will not interfere with the jaws 1610, 1612 coming together and establishing the correct jaw gap 2103. Sizing and tolerances must again account for the variation of distal components of the end effector 1604.

RF Tool with Split Articulation Joint and Knife Guide

Figure 33:
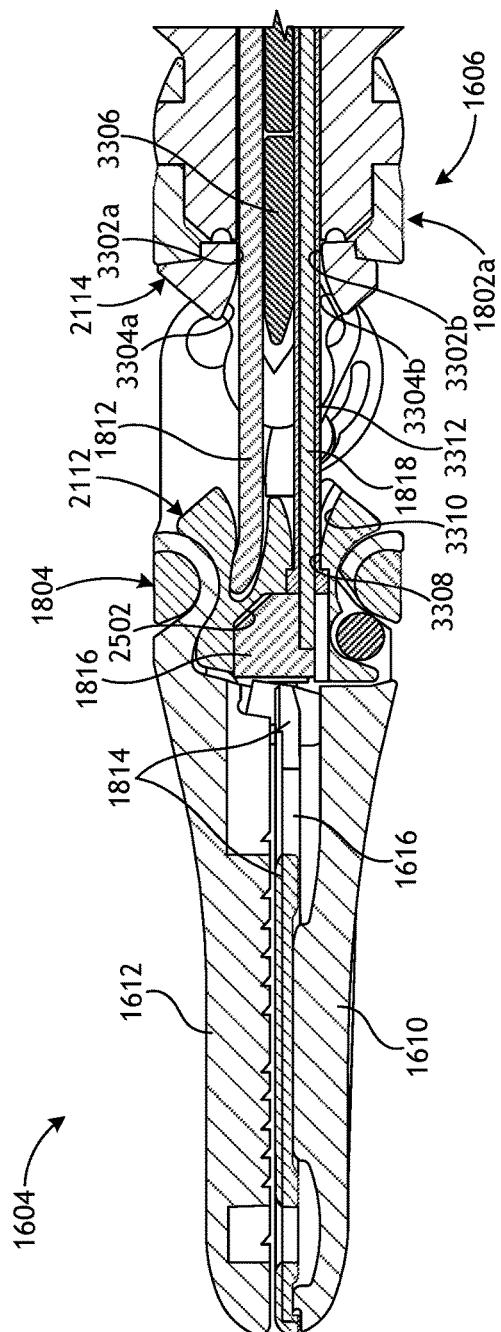
FIG. 33 is a cross-sectional side view of the end effector and the wrist of FIG. 18, according to one or more embodiments of the disclosure.

FIG. 33 is a cross-sectional side view of the end effector 1604 and the wrist 1606 of FIG. 18, according to one or more embodiments of the disclosure. As illustrated, one or more guiding components may be included in the wrist 1606 and arranged in the central portion or middle of the wrist 1606 to help guide one or both of the electrical conductor 1812 and the knife 1816 to the jaws 1610, 1612. More specifically, the distal wedge 2112 and the mid-articulation insert 2114 may comprise guiding components that are arranged axially in series in the middle of the wrist 1606. As described herein, the distal wedge 2112 may be generally arranged within the linkage 1804 and otherwise positioned between the electrode 1814 and the distal articulation joint 1802a, and the mid-articulation insert 2114 may be generally arranged within the distal articulation joint 1802a.

The electrical conductor 1812 may extend longitudinally through the wrist 1606 and terminate at the electrode 1814 to supply electrical energy to the end effector 1604. The mid-articulation insert 2114 may provide or otherwise define a first or "upper" passageway 3302a sized to receive and support the electrical conductor 1812 as it extends through the distal articulation joint 1802a. In at least one embodiment, as illustrated, an exit opening 3304a of the first passageway 3302a may be enlarged and otherwise flared outward. This may prove advantageous in providing strain relief for the electrical conductor 1812 while the end effector 1604 articulates, thus helping to avoid premature fatigue of the electrical conductor 1812. After exiting the first passageway 3302a, the electrical conductor 1812 may then extend to and be received by the distal wedge 2112. More specifically, the channel 2602 defined by the distal wedge 2112 may receive the electrical conductor 1812 and may guide the electrical conductor 1812 to the electrode 1814, as generally described above.

The knife 1816 is coupled to the distal end of the drive rod 1818 and configured to be stowed in the knife housing 2502 of the distal wedge 2112 when not in use. As discussed above, longitudinal movement (translation) of the drive rod 1818 correspondingly moves the knife 1816 out of the knife housing 2502 and back and forth within the guide track(s) 1616 defined in the jaws 1610, 1612. Once the knife 1816 is no longer needed, the drive rod 1818 is retracted and the knife 1816 is correspondingly moved back into the knife housing 2502 for safe storage.

The drive rod 1818 extends longitudinally through the wrist 1606 to connect to the knife 1816. The mid-articulation insert 2114 may provide or otherwise define a second or "lower" passageway 3302b sized to receive and support the drive rod 1818 through the distal articulation joint 1802a. The first and second passageways 3302a,b may be separated by a central member 3306. Similar to the first passageway 3302a, in at least one embodiment, an exit opening 3304b to the second passageway 3302b may be enlarged and otherwise flared outward. This may prove advantageous in providing strain relief for the drive rod 1818 while the end effector 1604 articulates, thus helping to avoid premature fatigue of the drive rod 1818.

After exiting the second passageway 3302b, the drive rod 1818 may extend to and be received by the distal wedge 2112. More specifically, the drive rod 1818 may be received within a drive rod channel 3308 defined by the distal wedge 2112. The drive rod channel 3308 may extend to and be contiguous with the knife housing 2502. In at least one embodiment, an opening 3310 to the drive rod channel 3308 may be enlarged and otherwise flared outward. This may prove advantageous in providing strain relief for the drive rod 1818 while the end effector 1604 articulates, thus helping to avoid premature fatigue of the drive rod 1818.

In some embodiments, the drive rod 1818 may comprise a solid shaft, but may alternatively comprise a tube or tubular structure. Moreover, the drive rod 1818 may be made of a variety of flexible materials including, but not limited to, a metal or metal alloy (e.g., a nickel-titanium alloy or "nitinol"), a plastic or thermoplastic material, a composite material, or any combination thereof. The drive rod 1818 may also comprise a braided cable construction of any of the aforementioned materials, and such braided cable may be designed and radially constrained to support axial loads. In some embodiments, as illustrated, a flexible tube 3312 (e.g., a hypotube) may cover all or a portion of the drive rod 1818. The flexible tube 3312 may support and help prevent buckling of the drive rod 1818 upon assuming compressive loads during articulation of the wrist 1606 and opening and closure of the jaws 1610, 1612. Similar to the drive rod 1818, the flexible tube 3312 may be made of a variety of flexible materials including, but not limited to, a metal or metal alloy (e.g., a nickel-titanium alloy or "nitinol"), a metallic coil, a plastic or thermoplastic material, a composite material, or any combination thereof.

The distal wedge 2112 and the mid-articulation insert 2114 (i.e., the "guiding components") may prove advantageous in increasing the bend radius of the drive rod 1818 during articulation and actuation of the end effector 1604. More specifically, the second passageway 3302*b* and the drive rod channel 3308 may help control the proportion of supported length to unsupported length of the drive rod 1818 (and the flexible tube 3312), and thus increase the bend radius of the drive rod 1818 as it extends through the wrist 1606. Consequently, frictional forces assumed by the drive rod 1818 and the flexible tube 3312 when the jaws 1610, 1612 are in an articulated pose may be reduced, which can reduce fatigue of the drive rod 1818 and the flexible tube 3312. Increasing the bend radius also decreases the loading on articulation cables required to achieve given poses of the end effector 1604. Decreased cable loads can lead to reduced stress, less cable stretch, and better controllability of the robotic instrument.

In some embodiments, one or both of the distal wedge 2112 and the mid-articulation insert 2114 may be separate component parts included in the assembly of the wrist 1606. In such embodiments, the distal wedge 2112 and the mid-articulation insert 2114 may not be coupled or fixed to any portion of the end effector 1604 or the wrist 1606, but may instead be arranged between adjacent portions of the linkage 1804 and the distal articulation joint 1802*a*, respectively, and secured within the wrist 1606 as the wrist 1606 is assembled. In other embodiments, however, the distal wedge 2112 may form an integral part of the linkage 1804, and/or the mid-articulation insert 2114 may form an integral part of the distal articulation joint 1802*a*, without departing from the scope of the disclosure.

Figure 34B:
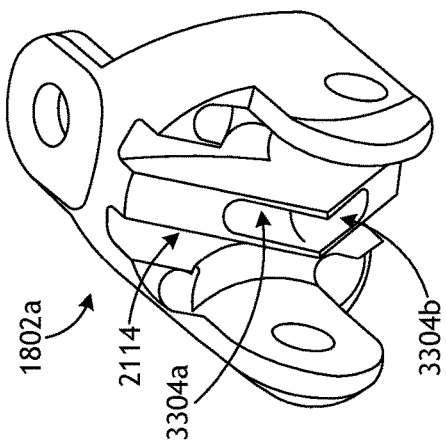
FIG. 34B is an isometric view of the proximal clevis and the mid-articulation insert, according to one or more additional embodiments.
Figure 34A:
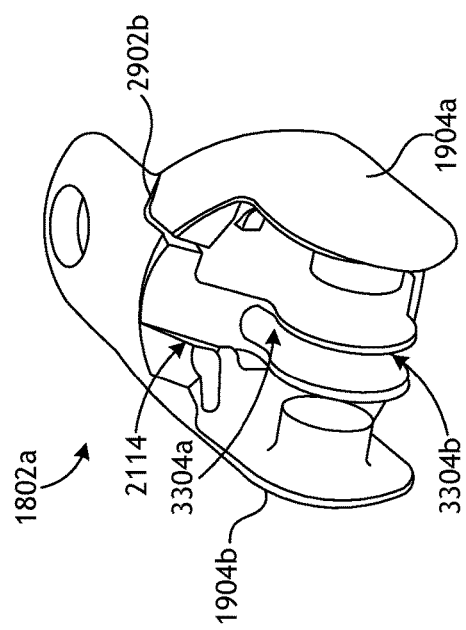
FIG. 34A is an isometric view of the proximal clevis and the mid-articulation insert, according to one or more embodiments.

FIG. 34A is an isometric view of the distal articulation joint 1802*a* and the mid-articulation insert 2114, according to one or more embodiments. As illustrated, the exit openings 3304*a,b* to the first and second passageways 3302*a,b* (FIG. 33), respectively, are depicted for accommodating the electrical conductor 1812 (FIG. 33) and the drive rod 1818 (FIG. 33), as described above.

In the illustrated embodiment, the mid-articulation insert 2114 comprises a separate component part from the distal articulation joint 1802*a*. Moreover, the distal articulation joint 1802*a* includes the opposing first and second distal articulation joint portions 1904*a,b*, and joining the distal articulation joint portions 1904*a,b* at the distal joint interface (s) 2902*b* (one shown) secures the mid-articulation insert 2114 within the wrist 1606. Accordingly, the mid-articulation insert 2114 may be detached from any portion of the distal articulation joint 1802*a*, and is instead secured within the wrist 1606 as the distal articulation joint portions 1904*a,b* are joined and the wrist 1606 (FIG. 33) is assembled.

FIG. 34B is an isometric view of the distal articulation joint 1802*a* and the mid-articulation insert 2114, according to one or more additional embodiments. The exit openings 3304*a,b* to the first and second passageways 3302*a,b* (FIG. 33), respectively, are again depicted for accommodating the electrical conductor 1812 (FIG. 33) and the drive rod 1818 (FIG. 33), as described above. In the illustrated embodiment, the mid-articulation insert 2114 forms an integral part of the distal articulation joint 1802*a*. Accordingly, the distal articulation joint 1802*a* may comprise a monolithic structure that does not require jointing by any means during manufacturing; e.g., no welding, soldering, braising, adhesives, or mechanical fasteners are required.

Figure 35A:
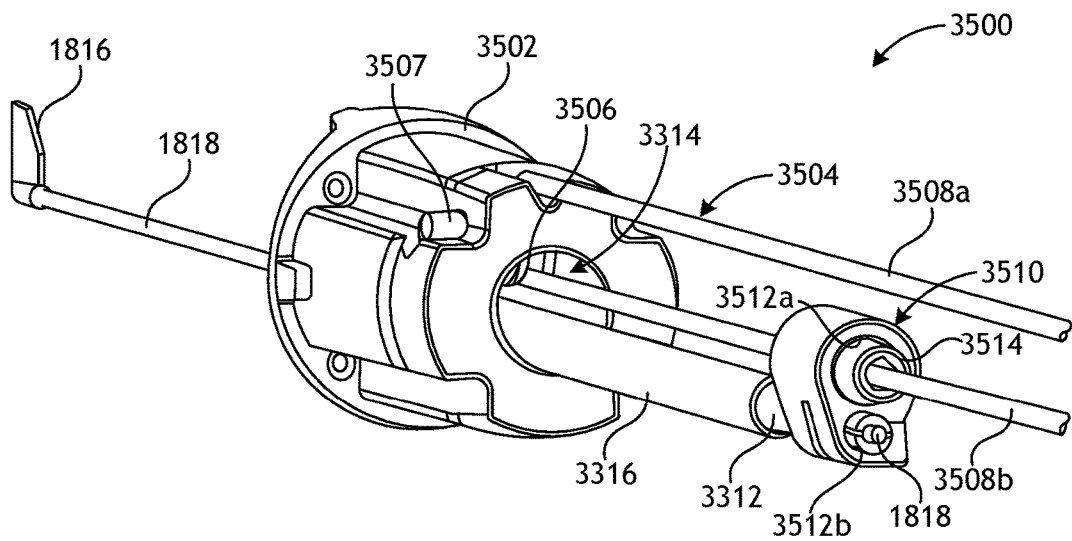
FIGS. 35A and 35B are back and front isometric views, respectively of an example knife drive system, according to one or more embodiments.
Figure 35B:
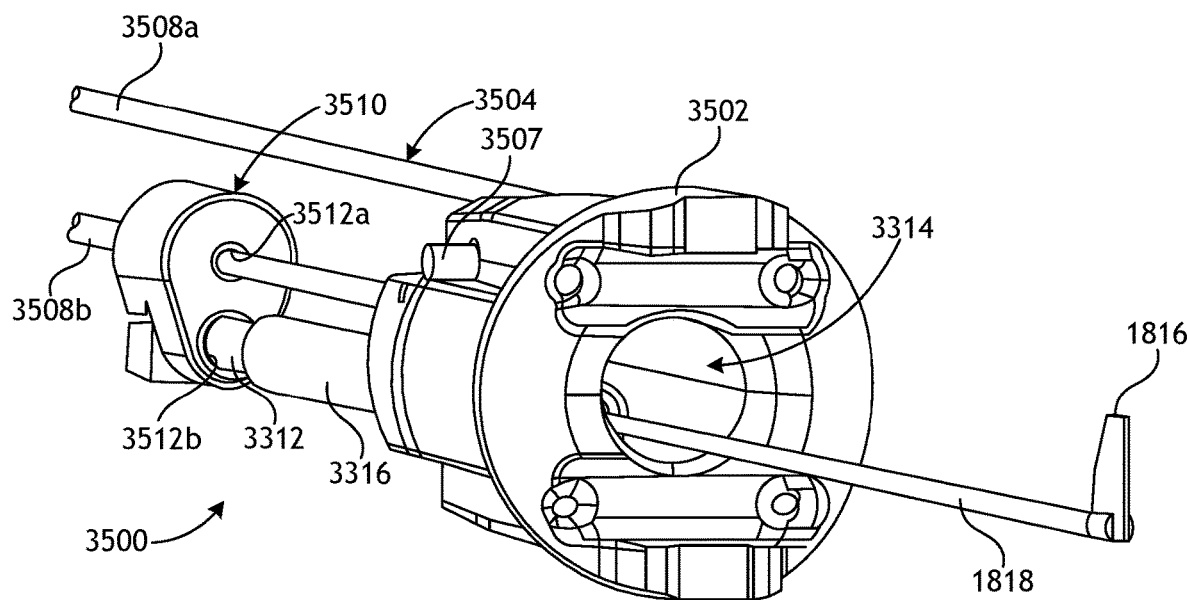

FIGS. 35A and 35B are back and front isometric views, respectively of an example knife drive system 3500, according to one or more embodiments. The knife drive system 3500 may be incorporated into the surgical tool 1600 of FIG. 16 to advance and retract the knife 1816 during operation. As illustrated, the knife drive system 3500 may be mounted to a shaft adapter 3502 at or near the wrist 1606 (FIG. 16). In some embodiments, the shaft adapter 3502 may comprise the proximal articulation joint 1802*b* (FIG. 18) or may form an integral part or extension of the shaft 1602 (FIG. 16). In other embodiments, the shaft adapter 3502 may comprise the distal articulation joint 1802*a* of the wrist 1602, and in yet other embodiments the shaft adapter 3502 may be pivotably coupled to the distal articulation joint 1802*a*, without departing from the scope of the disclosure.

The knife drive system 3500 may comprise a cable-based architecture that uses a drive member 3504 to advance or retract the knife 1816. Similar to the drive members 1808*a-d* (FIG. 18), the drive member 3504 may form part of the actuation systems housed within the handle 1614 (FIGS. 16 and 17), and may comprise a cable, a band, a line, a cord, a wire, a woven wire, a rope, a string, a twisted string, an elongate member, a belt, a flexible shaft, or any combination thereof. Moreover the drive member 3504 can be made from a variety of materials including, but not limited to, a metal (e.g., tungsten, stainless steel, nitinol, etc.), a metallic braided cable, a polymer (e.g., ultra-high molecular weight polyethylene or Dyneema®), a polymer braided cable, a synthetic fiber (e.g., KEVLAR®, VECTRAN®, etc.), an elastomer, or any combination thereof.

As illustrated, the drive member 3504 loops around a pulley 3506 (FIG. 35A) rotatably mounted to the shaft adapter 3502 at a pin 3507, thus forming a first drive member portion 3508*a* and a second drive member portion 3508*b*. The drive member portions 3508*a,b* each extend proximally from the pulley 3506 toward the handle 1614 (FIGS. 16 and 17) where they are operatively coupled to one or more actuation mechanisms or device that facilitate antagonistic longitudinal movement (translation) of the drive member 3504. Selective actuation of one of the drive member portions 3508*a,b* applies tension (i.e., pull force) to the given drive member portion 3508*a,b* in the proximal direction, which urges the given drive member portion 3508*a,b* to move and the drive member portion 3508*a,b* naturally follows as connected thereto. Antagonistic operation of the drive member portions 3508*a,b* of the drive members 1808*a-d* advances or retracts the knife 1816, depending on the pull direction.

More specifically, the knife drive system 3500 may further include a collar 3510 that may be fixed to the drive member 3504 and the drive rod 1818 such that movement of the drive member 3504 correspondingly moves the drive rod 1818 in the same longitudinal direction and thereby advances or retracts the knife 1816. As illustrated, the drive member 3504 (e.g., the second drive member portion 3508b) extends through a first aperture 3512a defined through the collar 3510, and the drive member 3504 may be secured to the collar 3510 at the first aperture 3512a. In some embodiments, the drive member 3504 may be crimped or knotted and the crimp or knot may be trapped between the collar 3510 and a stop member 3514 arranged within the first aperture 3512a. In one or more embodiments, the stop member 3514 may comprise hypodermic tubing.

A proximal end of the drive rod 1818 may extend at least partially through a second aperture 3512b defined through the collar 3510, and the drive rod 1818 may be secured to the collar 3510 at the second aperture 3512b. In some embodiments, as illustrated, the drive rod 1818 may be received within the flexible tube 3312, as generally described above. In such embodiments, the flexible tube 3312 may be slotted at the second aperture 3512b to allow effective compression force around the proximal end of the drive rod 1818. The collar 3510 may also be slotted in various locations to ensure a tight compression fit about the drive rod 1818. In some embodiments, the collar 3510 may be compressible around the drive rod 1818 and the flexible tube 3312 with a screw and may then be welded in the compressed state to maintain clamp pressure against the drive rod 1818 and the flexible tube 3312.

The drive rod 1818 may extend through a central aperture 3314 defined longitudinally through the shaft adapter 3502. In some embodiments, a hypotube 3316 may surround the drive rod 1818 and the flexible member 3312 (or only the drive rod 1818) as extending through the central aperture 3314. During operation, the drive rod 1818 and the flexible member 3312 (or only the drive rod 1818) slide longitudinally through the hypotube 3316, and the hypotube 3316 may help to prevent buckling of the drive rod 1818.

In example operation, once the collar 3510 is properly secured to the drive member 3504 and the drive rod 1818, actuating the first drive member portion 3502a in the proximal direction will correspondingly cause the drive rod 1818 and the knife 1816 to move distally. In contrast, actuating the second drive member portion 3502b in the proximal direction will correspondingly cause the drive rod 1818 and the knife 1816 to move proximally.

Figure 36:
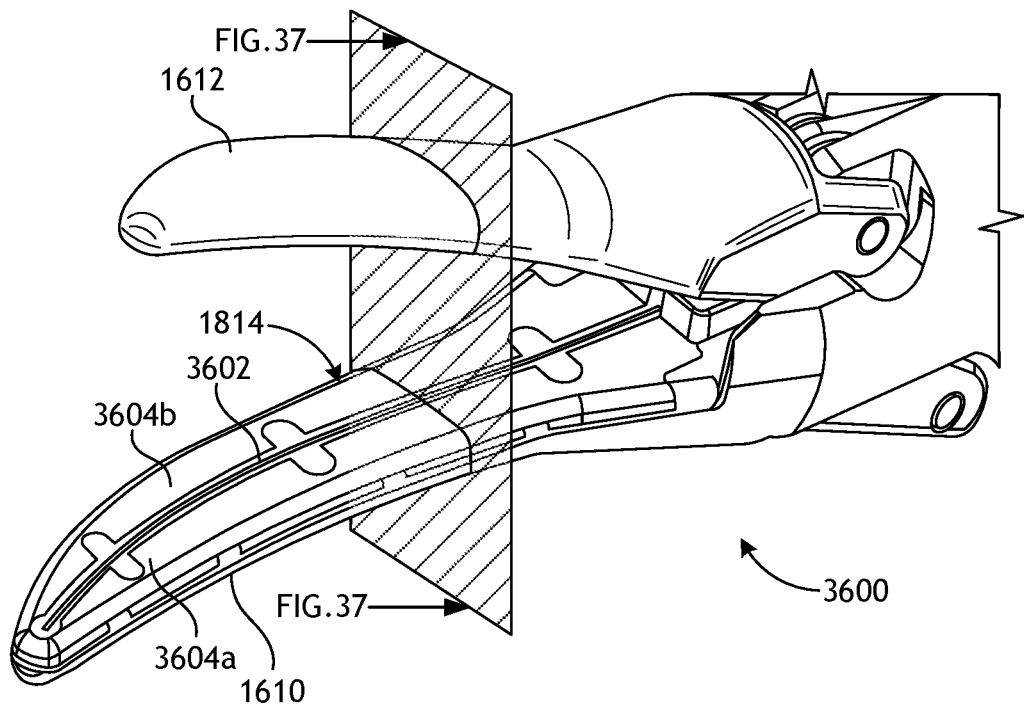
FIG. 36 is an isometric view of an example end effector, according to one or more additional embodiments of the disclosure.

FIG. 36 is an isometric view of another example end effector 3600, according to one or more embodiments. The end effector 3600 may be similar in some respects to the end effector 1604 of FIG. 18 and, therefore, may be best understood with reference thereto, where like reference numerals refer to like components not described again. Similar to the end effector 1604 of FIG. 18, for example, the end effector 3600 may be used with the surgical tool 1600 of FIG. 16. Moreover, the end effector 3600 may comprise a vessel sealer that has the first and second jaws 1610, 1612 that move simultaneously to actuate the end effector 3600 between open and closed positions; i.e., bifurcating jaws. Accordingly, the end effector 3600 may be configured to compress and cut tissue grasped between the jaws 1610, 1612.

Unlike the end effector 1604 of FIG. 18, however, the end effector 3600 does not use a knife (or cutting element) to cut tissue. Instead, the end effector 3600 may include a cutting electrode 3602 that extends longitudinally along at least a portion of the first or second jaw 1610, 1612 and is configured for electrical cutting (or heating) versus mechanical cutting. In the illustrated embodiment, the cutting electrode 3602 is depicted as forming part of the first jaw 1610, but could alternatively form part of the second jaw 1612, or both jaws 1610, 1612, without departing from the scope of the disclosure. Moreover, the cutting electrode 3602 is depicted extending longitudinally through (along) the middle of the electrode 1814, alternately referred to herein as the "sealing electrode 1814". Accordingly, the cutting electrode 3602 may bifurcate the sealing electrode 1814 and interpose first and second sealing electrode sections 3604a and 3604b.

Similar to the sealing electrode 1814, the cutting electrode 3602 may be configured for high current density monopolar or bipolar radio frequency (RF) operation. In at least one embodiment, the cutting electrode 3602 may comprise a simple wire configured for electrical heating and/or cutting. Moreover, in addition to the electrical conductor 1812 (FIG. 18), the end effector 3600 may include a second electrical conductor (not shown) provides electrical power to the cutting electrode 3602. In some embodiments, the second electrical conductor may communicate with the same electrical circuit as the sealing electrode 1814, thus making the end effector 3600 a bipolar operating device. In such embodiments, the sealing and cutting electrodes 1814, 3602 may share the same electrical return circuit (e.g., a common ground). In some embodiments, selective operation of the sealing and cutting electrodes 1814, 3502 may be based on a control algorithm that commands vessel sealing, cutting, or both vessel sealing and cutting simultaneously as directed by the operator.

The cutting electrode 3602 may prove advantageous for a variety of reasons. For example, the cutting electrode 3602 may be capable of replacing the entire mechanical knife system described herein, which eliminates the complexity of driving a knife in and through the system. This also results in reduced parts and frees up at least one drive input 1620a-f (FIGS. 16-17) at the handle 1614 (FIGS. 16-17). Moreover, the cutting electrode 3602 may simplify assembly of the end effector 3600 and allow drive members that open and close the jaws 1610, 1612 to be routed through the central axis of the wrist 1606 (FIG. 16) and the articulation joints (devises) 1802a,b (FIG. 18). This may prove advantageous in reducing or eliminating tip dive of the jaws 1610, 1612 and allowing a general rearrangement of lumen ports and configurations of the wrist 1606.

Figure 37:
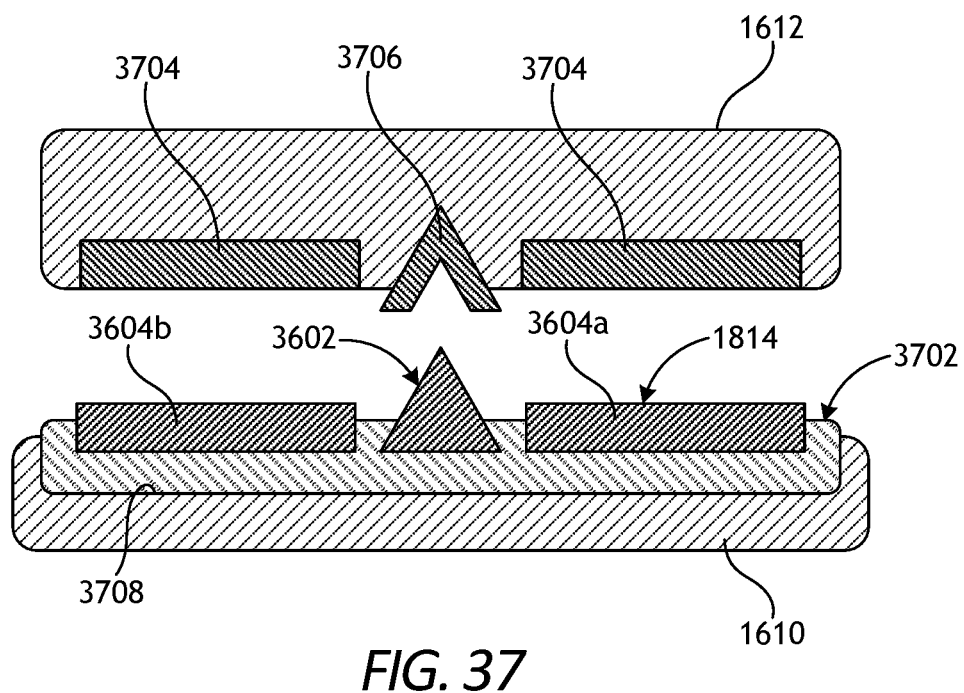
FIG. 37 is a cross-sectional end view of the jaws of FIG. 36 taken along the plane indicated in FIG. 36, according to one or more embodiments.

FIG. 37 is a cross-sectional end view of the jaws 1610, 1612 as taken along the plane indicated in FIG. 36, according to one or more embodiments. In some embodiments, the sealing and cutting electrodes 1814, 3602 may be mounted to or otherwise form part of a removable cartridge 3702, thus providing discrete cutting and sealing electrical paths. In the illustrated embodiment, the removable cartridge 3702 is able to be mounted or secured to the first jaw 1610, but could alternatively be mounted or secured to the second jaw 1612, without departing from the scope of the disclosure. The removable cartridge 3702 may be replaced, for example, after each use or otherwise prior to use on the next patient.

In some embodiments, the second jaw 1612 may include or otherwise have mounted thereto one or more non-conductive spacers 3704 (two shown) configured to oppose the sealing electrode sections 3604a,b. Moreover, another non-conductive spacer 3706 may be included in the second jaw 1612 to oppose the cutting electrode 3602. The spacers 3704, 3706 may be dispersed on corresponding electrically active or passive electrodes. In at least one embodiment, the second jaw 1612 may also have a replaceable cartridge that carries and secures the non-conductive spacers 3704, 3706.

The removable cartridge 3702 may be received within a pocket 3708 (alternately referred to as a "shelf") defined in the first jaw 1610. The removable cartridge 3702 may be secured within the pocket 3708 via a variety of attachment means including, but not limited to, a snap fit engagement, an interference fit, one or more mechanical fasteners, or any combination thereof.

In some embodiments, the cutting electrode 3602 may exhibit a current-density focusing shape. In the illustrated embodiment, for example, the cutting electrode 3602 exhibits a generally triangular cross-sectional shape, thus resulting in current density focused at the exposed tip of the triangular shape. As will be appreciated, other polygonal cross-sectional shapes may be employed and provide current-density focusing properties, without departing from the scope of the disclosure. In one or more embodiments, the cutting electrode 3602 may exhibit flat cross-sectional shape, such as square or rectangle, which may be advantageous for ease of manufacturing.

Figure 38:
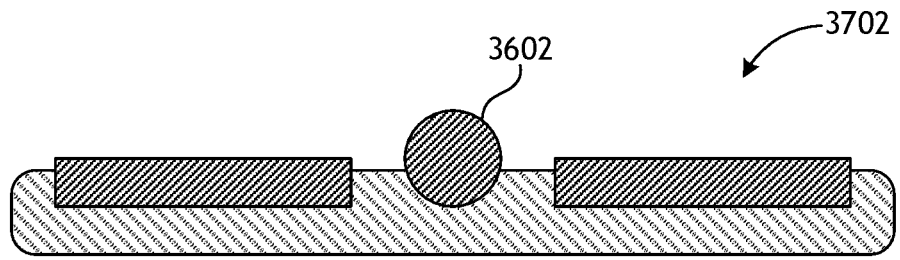
FIG. 38 depicts an alternative embodiment of the removable cartridge of FIG. 37.

FIG. 38 depicts an alternative embodiment of the removable cartridge 3702 where the cutting electrode 3602 exhibits a generally circular shape. In other embodiments, the cutting electrode 3602 may exhibit other curved shapes, such as oval or ovoid, without departing from the scope of the disclosure.

Figure 39:
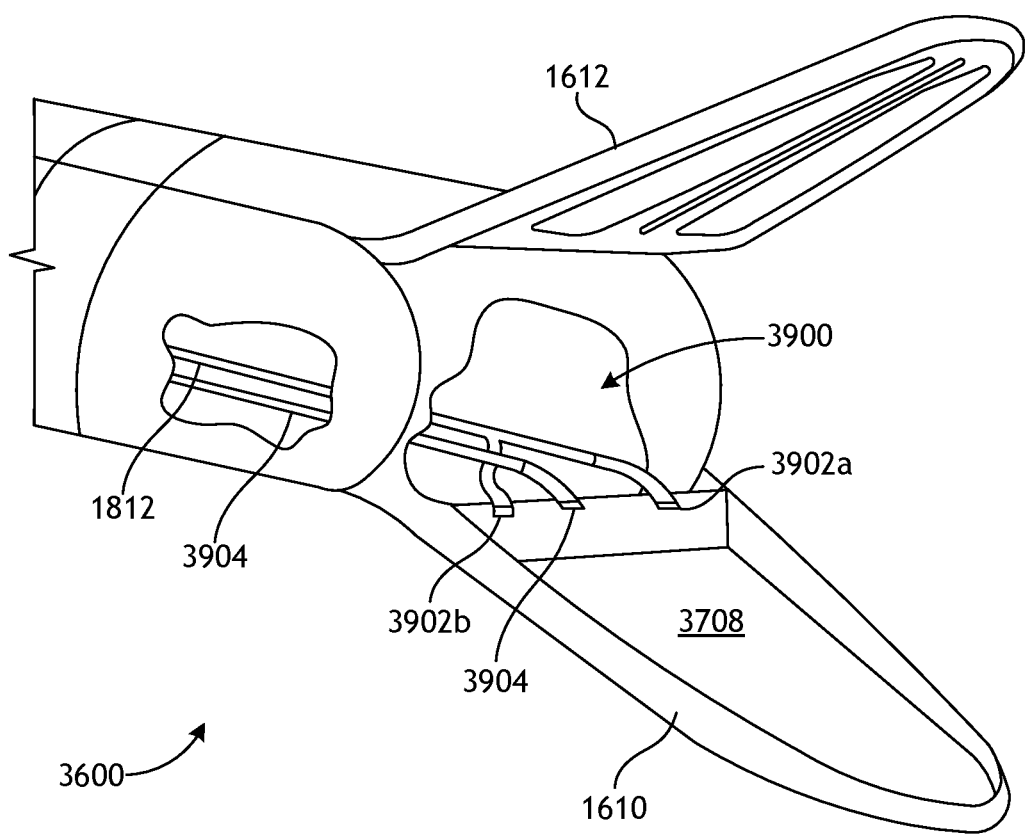
FIG. 39 is an isometric view of the end effector of FIG. 36 with an exposed electrical system, according to one or more embodiments.

FIG. 39 is an isometric view of the end effector 3600 of FIG. 36 depicting an exposed electrical system 3900, according to one or more embodiments. FIG. 39 also depicts one embodiment of the pocket 3708 provided in the first jaw 1610 and sized to receive the removable cartridge 3702 (FIGS. 37-38). As illustrated, the pocket 3708 may comprise a shelf or recess defined by the first jaw 1610, but could alternatively be provided in the second jaw 1612.

In the illustrated embodiment, the electrical system 3900 includes the electrical conductor 1812 that extends to and terminates at the end effector 3600 to supply electrical energy to the sealing electrode 1814 (FIGS. 36-37) and, more particularly, to the sealing electrode sections 3604a,b (FIGS. 36-37). In some embodiments, as illustrated, the electrical conductor 1812 may split into first and second conductor portions 3902a and 3902b to simultaneously provide electrical energy to the sealing electrode sections 3604a,b, respectively.

The electrical system 3900 may also include a second electrical conductor 3904 configured to supply electrical energy to the cutting electrode 3602 (FIGS. 36-37). Similar to the first electrical conductor 1812, the second electrical conductor 3904 may comprise a wire, but may alternatively comprise a rigid or semi-rigid shaft, rod, or strip (ribbon) made of a conductive material. Moreover, the electrical conductor 1812 may be partially covered with an insulative covering (overmold) made of a non-conductive material.

The electrical conductors 1812 (i.e., the conductor portions 3902a,b), 3904 may terminate at the jaws 1610, 1612 such that receiving the removable cartridge 3702 (FIGS. 37-38) into the pocket 3708 may facilitate electrical connection between the conductor portions 3902a,b and the sealing electrode sections 3604a,b (FIGS. 36-37), and between the second electrical conductor 3904 and the cutting electrode 3602 (FIGS. 36-37), thus providing electrical power to the sealing and cutting electrodes 1814, 3602. In at least one embodiment, the terminal ends of the electrical conductors 1812, 3904 may comprise spring contact electrodes that help facilitate proper electrical coupling and connection upon mounting the cartridge 3702 in the pocket 3708.

Accordingly, in one or more embodiments, the electrical system 3900 may provide two electrically isolated signals from the two electrically isolated electrical conductors 1812, 3904. The first conductor 1812 (i.e., the conductor portions 3902a,b of FIGS. 36-37) may provide a first signal to the sealing electrode sections 3604a,b (FIGS. 36-37) for sealing, and the second conductor 3904 provides a second signal to the cutting electrode 3602 (FIGS. 36-37) for cutting. In some embodiments, the electrical system 3900 may be configured for bipolar operation and the return path for the current may be through the second jaw 1612. In other embodiments, however, the electrical system 3900 may be configured for monopolar operation and the return path may be through a patient grounding pad, with electrical isolation zones mating with the cutting electrode 3602.

3. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
    an elongate shaft;
    an end effector arranged at a distal end of the shaft and including opposing first and second jaws; and
    an articulable wrist that interposes the end effector and the distal end, the wrist including a linkage providing one or more lateral arms receivable within a corresponding one or more grooves defined in the first and second jaws,
    wherein the one or more lateral arms and the one or more grooves extend perpendicular to a longitudinal axis of the end effector, and
    wherein mounting the linkage to the first and second jaws at the corresponding one or more groove generates a jaw pivot where the first and second jaws pivot between open and closed positions.

2. The robotic surgical tool of claim 1, wherein the one or more lateral arms slidably engage the corresponding one or more grooves as the first and second jaws pivot between the open and closed positions.

3. The robotic surgical tool of claim 1, wherein the linkage comprises first and second linkage portions matable at one or more linkage interfaces, and wherein each linkage portion provides a lateral arm of the one or more lateral arms.

4. The robotic surgical tool of claim 3, wherein the first and second linkage portions are joined via at least one of welding, soldering, brazing, an adhesive, an interference fit, one or more mechanical fasteners, and any combination thereof.

5. The robotic surgical tool of claim 1, further comprising a distal wedge positioned within a central portion of the wrist, the distal wedge defining one or more arcuate surfaces engageable with one or more corresponding curved portions of the first and second jaws.

6. A method of assembling an end effector, comprising:
    arranging a linkage about opposing first and second jaws of the end effector, the linkage including first and second linkage portions and each linkage portion providing a lateral arm;
    receiving the lateral arm of the first linkage portion in a first groove defined in the first jaw, and receiving the lateral arm of the second linkage portion in a second groove defined in the second jaw, wherein the first and second lateral arm and the first and second groove extend perpendicular to a longitudinal axis of the end effector;
    pivoting the first and second jaws toward a closed position;
    adjusting the first and second linkage portions until a desired jaw gap is provided between opposing inner surfaces of the first and second jaws; and
    joining the first and second linkage portions at one or more linkage interfaces, and thereby setting the desired jaw gap for operation.

7. The method of claim 6, wherein pivoting the first and second jaws toward the closed position comprises moving the first and second jaws toward the closed position until a distal end of the first and second jaws engage each other.

8. The method of claim 6, wherein adjusting the first and second linkage portions comprises adjusting a position of the lateral arms in the first and second grooves.

9. The method of claim 6, wherein adjusting the first and second linkage portions comprises:
    pushing the first and second linkage portions together; and
    adjusting the first and second linkage portions up or down until the desired jaw gap is achieved.

10. The method of claim 6, further comprising adjusting the first and second linkage portions until the opposing inner surfaces of the first and second jaws are parallel.

11. The method of claim 6, further comprising adjusting the first and second linkage portions until the opposing inner surfaces of the first and second jaws are non-parallel.

12. The method of claim 6, wherein arranging the linkage about the opposing first and second jaws is preceded by:
    positioning a distal wedge between the first and second jaws, the distal wedge defining one or more arcuate surfaces; and
    receiving one or more corresponding curved portions of the first and second jaws within the one or more arcuate surfaces.

13. The method of claim 6, wherein the first and second grooves each provide distal and proximal sides, the method further comprising increasing a mechanical advantage of the first and second jaws for closure by joining the first and second linkage portions with the lateral arms engageable against the distal side of the first and second grooves.

14. The method of claim 6, wherein the first and second grooves each provide distal and proximal sides, the method further comprising increasing a mechanical advantage of the first and second jaws for opening by joining the first and second linkage portions with the lateral arms engageable against the proximal side of the first and second grooves.

15. An end effector for a robotic surgical tool, comprising:
    a first jaw providing a first groove;
    a second jaw providing a second groove; and
    a linkage mountable to the first and second jaws and including a first linkage portion having a first lateral arm receivable within the first groove and a second linkage portion having a second lateral arm receivable within the second groove,
    wherein the first and second lateral arms and the first and second grooves extend perpendicular to a longitudinal axis of the end effector, and
    wherein joining the first and second linkage portions at one or more joint interfaces sets a jaw gap for the first and second jaws.

16. The end effector of claim 15, wherein the first and second linkage portions are joined via at least one of welding, soldering, brazing, an adhesive, an interference fit, one or more mechanical fasteners, and any combination thereof.

17. The end effector of claim 15, wherein the one or more lateral arms slidably engage the corresponding one or more grooves as the first and second jaws pivot between open and closed positions.

18. The end effector of claim 15, wherein the first and second jaws provide first and second jaw extensions, and wherein the end effector further comprises a distal wedge positioned between the first and second jaw extensions and defining one or more arcuate surfaces engageable with one or more corresponding curved portions of the first and second jaws.

19. The surgical tool of claim 1, wherein the linkage comprises:
   a first linkage portion providing a first lateral arm of the one or more lateral arms; and
   a second linkage portion providing a second lateral arm of the one or more lateral arms,
   wherein the first lateral arm is mated to the second linkage portion at a first linkage interface, and the second lateral arm is mated to the first linkage portion at a second linkage interface.

20. The surgical tool of claim 1, wherein the linkage comprises:
   a first linkage portion providing a first lateral arm of the one or more lateral arms; and
   a second linkage portion providing a second lateral arm of the one or more lateral arms,
   wherein the first and second linkage portions extend about the first and second jaws and thereby secure the first and second jaws to the wrist.

* * * * *